US008846006B2

(12) United States Patent
Frank et al.

(10) Patent No.: US 8,846,006 B2
(45) Date of Patent: Sep. 30, 2014

(54) MRI MARKERS, DELIVERY AND EXTRACTION SYSTEMS, AND METHODS OF MANUFACTURE AND USE THEREOF

(75) Inventors: Steven J. Frank, Bellaire, TX (US); Karen Martirosyan, Houston, TX (US)

(73) Assignees: Board of Regents, The University of Texas System, Austin, TX (US); The University of Houston System, Houston, TX (US)

( * ) Notice: Subject to any disclaimer, the term of this patent is extended or adjusted under 35 U.S.C. 154(b) by 1 day.

(21) Appl. No.: 13/355,229

(22) Filed: Jan. 20, 2012

(65) Prior Publication Data

US 2012/0189551 A1 Jul. 26, 2012

Related U.S. Application Data

(60) Provisional application No. 61/434,719, filed on Jan. 20, 2011.

(51) Int. Cl.
*A61B 5/055* (2006.01)
*A61K 49/10* (2006.01)
*A61K 49/00* (2006.01)

(52) U.S. Cl.
CPC ..................................... *A61K 49/10* (2013.01)
USPC .......................................... 424/9.1; 424/9.3

(58) Field of Classification Search
USPC ......................................................... 424/9.3
See application file for complete search history.

(56) References Cited

U.S. PATENT DOCUMENTS

| | | | |
|---|---|---|---|
| 5,628,982 | A | 5/1997 | Lauffer et al. |
| 6,333,971 | B2 | 12/2001 | McCrory et al. |
| 6,521,773 | B1 | 2/2003 | Hainfeld |
| 6,534,039 | B2 | 3/2003 | Hainfeld |
| 7,418,289 | B2 | 8/2008 | Hyde et al. |
| 2001/0021397 | A1 * | 9/2001 | Mirsky et al. ................. 424/725 |
| 2002/0028993 | A1 | 3/2002 | Hainfeld |
| 2003/0228255 | A1 | 12/2003 | Park et al. |
| 2004/0109823 | A1 | 6/2004 | Kaplan |
| 2004/0225231 | A1 | 11/2004 | Ehr |
| 2005/0107870 | A1 | 5/2005 | Wang et al. |

FOREIGN PATENT DOCUMENTS

| | | |
|---|---|---|
| WO | 94/17733 | 8/1994 |
| WO | 2000038738 | 7/2000 |
| WO | 2002007846 | 1/2002 |
| WO | 2005/089664 | 9/2005 |
| WO | 2009009760 | 1/2009 |

OTHER PUBLICATIONS

Patel, Daksha, et al.; Poly(D,L-lactide-co-glycolide) coated superparamagnetic iron oxide nanoparticles: Synthesis, characterization and in vivo study as MRI contrast agent; Colloids and Surfaces A: Physicochem. Eng. Aspects; 313-314 (2008) 91-94.
Clegg, W., Lacy, O.I., and Straughan, B., "Structures of Three Glycine-Bridged Polymeric Complexes: [Mn (glycine)(H2O)2Cl2], [Co(glycine)(H2O)2Cl2] and [Co(glycine)(H2o)4](NO3)2," Acta Crystallographica, 1987, Section C43, pp. 794-797, copyright 1987 International Union of Crystallography.
Stenzel, K. and Fleck, M., "Poly[[[diaquacobalt(ll)]-di-μ-glycine] dichloride]," Metal-Organic Papers, Acta Crystallographica, Sep. 25, 2004, Structure Reports Online, Section E60, pp. m1470-1472, copyright 2004 International Union of Crystallography.
Frank, S.J., et al., "A Novel MRI Marker for Prostate Brachytherapy," Rapid Communication, accepted for publication Jan. 23, 2008, International Journal of Radiation Oncology Biology Physics, vol. 71, No. 1, pp. 5-8, copyright 2008 Elseveir Inc.
Nicolle, G.M., et al., "The Impact of Rigidity and Water Exchange on the Relaxivity of a Dendritic MRI Contrast Agent," Chemistry—A European Journal, 2002, vol. 8, No. 5, pp. 1040-1048, copyright 2002 Wiley-VCH.
Shastri, V.P., "Non-Degradable Biocompatible Polymers in Medicine: Past, Present and Future," Current Pharmaceutical Biotechnology, 2003, vol. 4, pp. 331-337, copyright 2003 Bentham Science Publishers Ltd.
Perez-Mayoral, E., et al., "Chemistry of paramagnetic and diamagnetic contrast agents for Magnetic Resonance Imaging and Spectroscopy pH responsive contrast agents," European Journal of Radiology, 2008, vol. 67, pp. 453-458, copyright 2008 Elsevier Ireland Ltd.
Sitharaman, B. and Wilson, L.J., "Gadonanotubes as new high-performance MRI contrast agents," International Journal of Nanomedicine 2006, vol. 1, No. 3, pp. 291-295, copyright 2006 Dove Medical Press Limited.
Donahue, K.M., Weisskoff, R.M., and Burstein, D., "Water Diffusion and Exchange as They Influence Contrast Enhancement," Journal of Magnetic Resonance Imaging, Jan./Feb. 1997, pp. 102-110, copyright 1997 ISMRM.
Toth, E., et al., "Water-Soluble Gadofullerenes: Toward High-Relaxivity, pH-Responsive MRI Contrast Agents," Journal of the American Chemical Society, vol. 127, No. 2, 2005, pp. 799-805, published Dec. 17, 2004, American Chemical Society.
Bloembergen, N. and Morgan, L.O., "Proton Relaxation Times in Paramagnetic Solutions. Effects of Spin Relaxation," The Journal of Chemical Physics, vol. 34, No. 3, pp. 842-850, Mar. 1961.
Crook, J., "Interobserver Variation in Postimplant Computed Tomography Contouring Affects Quality Assessment of Prostate Brachytherapy," Brachytherapy, 2002, vol. 1, No. 2, pp. 66-73, copyright 2002 Elseveir Inc.
Bloch, B.N. et al., "Prostate Cancer: Accurate Determination of Extracapsular Extension with High-Spatial-Resolution Dynamic Contrast-enhanced and T2-weighted MR Imaging—Initial Results", Radiology, Genitourinary Imaging, vol. 245, No. 1, pp. 176-185, Oct. 2007, copyright 2007 RSNA.
McLaughlin, P.W., et al., "Functional Anatomy of the Prostate: Implications for Treatment Planning," International Journal of Radiation Oncology Biology Physics, 2005, vol. 63, No. 2, pp. 479-491, copyright 2005 Elseveir Inc.

(Continued)

*Primary Examiner* — Michael G Hartley
*Assistant Examiner* — Melissa Perreira
(74) *Attorney, Agent, or Firm* — Locke Lord LLP

(57) ABSTRACT

Novel, non-toxic cobalt-based contrast and imaging agents for use in enhanced medical imaging modalities and processes are described, as well the manufacture of markers containing such contrast agents is described, and uses for such imaging markers and contrast agents in a variety of therapeutic applications and devices.

18 Claims, 22 Drawing Sheets

(56) References Cited

OTHER PUBLICATIONS

Lauffer, R.B., et al., "Hepatobiliary MR Contrast Agents: 5-Substituted Iron-EHPG Derivatives", Magnetic Resonance in Medicine, vol. 4, pp. 582-590, 1987, copyright 1987 Academic Press Inc.
Caravan, P., et al., "Gadolinium(III) Chelates as MRI Contrast Agents: Structure, Dynamics, and Applications", Chemical Reviews, vol. 99, pp. 2293-2352, 1999, copyright 1999 American Chemical Society.
Borel, A., Helm, L., and Merbach, A.E., "Molecular Dynamics Simulations of MRI-Relevant GdIII Chelates: Direct Access to Outer-Sphere Relaxivity", Chemistry—A European Journal, vol. 7, No. 3, pp. 600-610, 2001, copyright 2001 Wiley-VCH Verlag GmbH.
Krause, W., et al., "Contrast Agents: Magnetic Resonance Imaging—Relaxivity of MRI Contrast Agents", Topics in Current Chemistry, 2002, copyright 2002 Springer-Verlag Berlin Heidelberg, Germany.
"Toxicological Profile for Cobalt", U.S. Department of Health and Human Services, Public Health Service, Agency for Toxic Substances and Disease Registry, Apr. 2004.
Woo, R.K., et al., "Chapter 1—Biomaterials: Historical Overview and Current Directions", Nanoscale Technology in Biological Systems, CRC Press, copyright 2005 by Taylor & Francis.
Lee, H.B., et al., "Polymeric Biomaterials", The Biomedical Engineering Handbook: Second Edition, CRC Press LLC, 2000, Boca Raton.
Bolskar, R.D., et al., "Water-Soluble Gadofullerenes: Toward High-Relaxivity, pH-Responsive MRI Contrast Agents", Journal of the American Chemical Society, 2005, vol. 127, No. 2, pp. 799-805, American Chemical Society.
Solomon, I., "Relaxation Processes in a System of Two Spins," Physical Review, Jul. 1955, vol. 99, No. 2, pp. 559-565.
Butler, W.M. and Merrick, G.S., "Introduction to Prostate Brachytherapy," In: B.R. Thomadsen MJR, ed. Brachytherapy Physics 2nd edition, 2005, pp. 521-557.
Frank, S.J., et al., "An Assessment of Quality of Life Following Radical Prostatectomy, High-Dose External Beam Radiation Therapy, and Brachytherapy Iodine Implantation as Monotherapies for Localized Prostate Cancer," The Journal of Urology, 2007, vol. 177, No. 6, pp. 2151-2156, copyright 2007 American Urological Association.
Zelefsky, M.J., et al., "Multi-Institutional Analysis of Long-Term Outcome for Stages T1-T2 Prostate Cancer Treated With Permanent Seed Implantation," International Journal of Radiation Oncology, Biology, Physics, 2007, vol. 67, No. 2, pp. 327-333, copyright 2007 Elsevier Inc.
Merrick, G.S., et al., "Variability of Prostate Brachytherapy Pre-implant Dosimetry: A Multi-Instutional Analysis," Brachytherapy, 2005, vol. 4, No. 4, pp. 241-251, copyright 2005 American Brachytherapy Society.
Shah, J.N., et al., "Improved Biochemical Control and Clinical Disease-free Survival with Intraoperative Versus Preoperative Preplanning for Transperineal Interstitial Permanent Prostate Brachytherapy," Cancer Journal, 2006, vol. 12, No. 4, pp. 289-297.
Matzkin, H., et al., "Comparison Between Two Iodine-125 Brachytherapy Implant Techniques: Pre-planning and Intra-Operative by Various Dosimetry Quality Indicators," Radiotherapy and Oncology, 2003, vol. 68, No. 3, pp. 289-294, copyright 2003 Elsevier Ireland Ltd.
Han, B.H., et al., "The Effect of Interobserver Differences in Post-Implant Prostate CT Image Interpretation on Dosimetric Parameters," Medical Physics, 2003, vol. 30, No. 6, pp. 1096-1102, copyright 2003 The American Association of Physicists in Medicine.
Frank, S.J., et al., "Interstitial Implant Alone or in Combination with External Beam Radiation Therapy for Intermediate-Risk Prostate Cancer: A Survey of Practice Patterns in the United States," Brachytherapy, 2007, vol. 6, No. 1, pp. 2-8.
Merrick, G.S., et al., "Initial Analysis of Pro-Qura: A Multi-institutional Database of Prostate Brachytherapy Dosimetry," Brachytherapy, 2007, vol. 6, No. 1, pp. 9-15.

Sanda, M.G., et al., "Quality of Life and Satisfaction With Outcome Among Prostate-Cancer Survivors," New England Journal of Medicine, 2008, vol. 358, No. 12, pp. 1250-1261.
Bretonniere, Y., et al., "Solid-State and Solution Properties of the Lanthanide Complexes of a New Heptadentate Tripodal Ligand: A Route to Gadolinium Complexes with an Improved Relaxation Efficiency," Inorganic Chemistry, 2001, vol. 40, pp. 6737-6745, copyright 2001 American Chemical Society.
Tempany, C.M., et al., "MR-Guided Prostate Interventions," Journal of Magnetic Resonance Imaging, 2008, vol. 27, pp. 356-367, copyright 2008 Wiley-Liss, Inc.
D'Amico, A.V., et al., "Comparing PSA Outcome After Radical Prostatectomy or Magnetic Resonance Imaging Guided Partial Prostatic Irradiation in Select Patients With Clinically Localized Adenocarcinoma of the Prostate," Urology, 2003, vol. 62, pp. 1063-1067, copyright 2003 Elsevier Inc.
Roberson, P.L., et al., "Use and Uncertainties of Mutual Information for Computed Tomography/Magnetic Resonance (CT/MR) Registration Post Permanent Implant of the Prostate," Medical Physics, Feb. 2005, vol. 32, No. 2, pp. 473-482, copyright 2005 The American Association of Physicists in Medicine.
De Bazelaire, C.M.J., et al., "MR Imaging Relaxation Times of Abdominal and Pelvic Tissues Measured in Vivo at 3.0 T: Preliminary Results", Relaxation Times of Abdominal and Pelvic Tissues, Mar. 2004, vol. 230, No. 3, pp. 652-659, copyright 2004 RSNA.
Unger, E.C.S.D., et al., "Gadolinium-Containing Copolymeric Chelates—A New Potential MR Contrast Agent," MAGMA, 1999, vol. 8, No. 3, pp. 154-162, copyright 1999 Elsevier Science B.V.
Wen, X., et al., "Synthesis and Characterization of Poly(L-Glutamic Acid) Gadolinium Chelate: A New Biodegradable MRI Contrast Agent," Bioconjugate Chemistry, 2004, vol. 15, No. 6, pp. 1408-1415, copyright 2004 American Chemical Society.
Rivera, B., et al., "Canine Transmissible Venereal Tumor: A Large-Animal Transplantable Tumor Model," Comparative Medicine, Aug. 2005, vol. 55, No. 4, pp. 335-343, copyright 2005 American Association for Laboratory for Animal Science.
McNichols, R.J., et al., "Percutaneous MRI Guided Laser Thermal Therapy in Canine Prostate," SPIE, 2005, vol. 5686, pp. 214.
Kangasniemi, M., et al., "Dynamic Gadolinium Uptake in Thermally Treated Canine Brain Tissue and Experimental Cerebral Tumors," Investigative Radiology, 2003, vol. 38, No. 2, pp. 102-107, copyright 2003 Lippincott Williams & Wilkins, Inc.
Hazle, J.D., et al., "MI-Guided Thermal Therapy of Transplanted Tumors in the Canine Prostate Using a Directional Transurethral Ultrasound Applicator," JMRI, 2002, vol. 15, No. 4, pp. 409-17, copyright 2002 Wiley-Liss Inc.
Diederich, C.J., et al., "Transurethral Ultrasound Applicators with Directional Heating Patterns for Prostate Thermal Therapy: In Vivo Evaluation Using Magnetic Resonance Thermometry", Medical Physics, Feb. 2004, vol. 31, No. 2, pp. 405-413, copyright 2004 The American Association of Physicists in Medicine.
Kangasniemi, M., et al., "Multiplanar MR Temperature-Sensitive Imaging of Cerebral Thermal Treatment Using Interstitial Ultrasound Applicators in a Canine Model", Journal of Magnetic Resonance Imaging, 2002, vol. 16, pp. 522-531, copyright 2002 Wiley-Liss Inc.
Young, L., International Search Report for International Patent Application No. PCT/US08/69861, dated Sep. 26, 2008.
Young, L., Written Opinion for International Patent Application No. PCT/US08/69861, dated Sep. 26, 2008.
Kupelian, P., et al., "Prostate Cancer: Image Guidance and Adaptive Therapy", Abstract, Advances in the Treatment Planning and Delivery of Radiotherapy, copyright 2007 S. Karger AG, Basel, vol. 40, pp. 289.
"Visicoil—Linear Fiducial Marker", Core Oncology, copyright Jan. 2008.
Sam Nordic, "Seeds", [retrieved from the Internet on Jun. 18, 2012 using <URL: http://www.samedical.se/radioterapi/engradiomain.htm>].
Ma, J., "Breath-Hold Water and Fat Imaging Using a Dual-Echo Two-Point Dixon Technique With an Efficient and Robust Phase-Correction Algorithm", Magnetic Resonance in Medicine, pp. 415-419, accepted Mar. 4, 2004, copyright 2004 Wiley-Liss, Inc.

(56) References Cited

OTHER PUBLICATIONS

Ma, J., "Multislice and Multicoil Phase-Sensitive Inversion-Recovery Imaging", Magnetic Resonance in Medicine, pp. 904-910, accepted Nov. 10, 2004, copyright 2005 Wiley-Liss, Inc.

Ma, J., et al., "Fat-Suppressed Three-Dimensional Dual Echo Dixon Technique for Contrast Agent Enhanced MRI", Journal of Magnetic Resonance Imaging, accepted Oct. 3, 2005, copyright 2006 Wiley-Liss, Inc.

Ma, J., et al., "Contrast agent enhanced breast imaging with a combined 3D dual echo Dixon and parallel imaging technique", Proc. Intl. Soc. Mag. Reson. Med. 14, 2006.

Ma, J., et al., "A fast spin echo two-point Dixon technique and its combination with sensitivity encoding for efficient T2-weighted imaging", Magnetic Resonance Imaging, accepted Oct. 16, 2005, copyright 2005 Elsevier Inc.

Son, J., et al., "Three-dimensional T1-weighted MR Imaging using a One-point Dixon Technique with Arbitrary Echo Time", Proc. Intl. Soc. Mag. Reson. Med. 13, 2005.

Ma, J., et al., "Silicone-Specific Imaging Using an Inversion-Recovery-Prepared Fast Three-Point Dixon Technique", Journal of Magnetic Resonance Imaging, pp. 298-302, accepted Oct. 30, 2003, copyright 2004 Wiley-Liss, Inc.

Ma, J., "Phase correction in two-point Dixon water and fat imaging using a three-dimensional region-growing algorithm", presented at the 12th annual scientific meeting of the International Society of Magnetic Resonance in Medicine, May 15-24, 2004, Japan.

Fuller, C.D., et al., "Fiducial Markers in Image-guided Radiotherapy of the Prostate", Reference Section, US Oncological Disease 2006, [retrieved from the Internet on Jun. 18, 2012 using <URL: http://www.touchbriefings.com/pdf/2460/ACF201.pdf>].

Lee, R., et al., "A Magnetic Resonance-based Seed Localization Method for I-125 Prostate Implants", Journal of Korean Medical Science 2007, vol. 22, pp. S129-S133, copyright the Korean Academy of Medical Sciences.

Brigham and Women's Hospital, "Prostate Cancer Radiation Oncology Service", [retrieved from the Internet on Mar. 3, 2009 using <URL: http://www.brighamandwomens.org/patient/prostatecancer-radiation.aspx>].

Susil, R., et al., "System for MR Image-guided Prostate Interventions: Canine Study", Radiology, Sep. 2003, vol. 228, No. 3, pp. 886-894.

Schueler, B., et al., "MRI Compatibility and Visibility Assessment of Implantable Medical Devices", Journal of Magnetic Resonance Imaging, vol. 9, pp. 596-603, copyright 1999 Wiley-Liss, Inc.

Giebeler, A., et al., "Dose perturbations from implanted helical gold markers in proton therapy of prostate cancer", Journal of Applied Clinical Medical Physics, vol. 10, No. 1, Winter 2009.

Kry, S., et al., "Investigation into the use of a MOSFET dosimeter as an implantable fiducial marker", Journal of Applied Clinical Medical Physics, vol. 10, No. 1, Winter 2009, [retrieved from the Internet on Mar. 3, 2009 using <URL: http://www.jacmp.org/index.php/jacmp/rt/printerFriendly/2893/1515>].

Patel, D., et al., Poly(D, L-lactide-co-flycolide) coated superparamagnetic iron oxide nanoparticles: Synthesis, characterization and in vivo study as MRI contrast agent; Colloids and Surfaces A: Physicochem. Eng. Aspects; 313-314 (2008) 91-94.

Baharlou, S., International Preliminary Report on Patentability for International Patent Application No. PCT/US2008/069861, The International Bureau of WIPO, dated Jan. 12, 2010.

Hubner, W., Annex to the Invitation to Pay Additional Fees—Communication Relating to the Results of the Partial International Search for International Patent Application No. PCT/US2012/022092, European Patent Office, dated Apr. 11, 2012.

Frank, S., "A Toxicokinetic Evaluation of Intraprostatically Administered Cobalt Dichloride—N-Acetyl Cysteine (CoCl2-NAC) Conjugate In a Rat Model of Systemic Exposure", International Journal of Radiation Oncology Biology Physics, vol. 81, No. 2, pp. 2464, dated Oct. 2, 2011, abstract.

Hubner, W., International Search Report for International Patent Application No. PCT/US2012/022092, dated Jul. 6, 2012.

Hubner, W., Written Opinion for International Patent Application No. PCT/US2012/022092, dated Jul. 6, 2012.

\* cited by examiner

Top: Daughter MS scan of $[Co(NAC)_2]^+$
Bottom: Daughter MS scan of $[Co(NAC)]^+$

MRI MARKERS, DELIVERY AND EXTRACTION SYSTEMS, AND METHODS OF MANUFACTURE AND USE THEREOF

CROSS REFERENCE TO RELATED APPLICATIONS

This application claims priority, under 35 U.S.C. Section 119, to U.S. Provisional Patent Application Ser. No. 61/434,719, filed Jan. 20, 2011, the content of which is incorporated herein in its entirety.

STATEMENT REGARDING FEDERALLY SPONSORED RESEARCH OR DEVELOPMENT

Not applicable.

REFERENCE TO APPENDIX

Not applicable.

BACKGROUND OF THE INVENTION

1. Field of the Invention

The inventions disclosed and taught herein relate generally to contrast agents and contrast agent markers for use in magnetic resonance imaging applications. More specifically, the inventions disclosed herein are related to novel contrast agents for use in MRI and related therapeutic imaging applications, as well as their manufacture and use in therapeutic devices and applications.

2. Description of the Related Art

Magnetic resonance imaging ("MRI") is a powerful imaging modality having a number of applications, ranging from molecular diagnostics, imaging, and therapeutics. For example, molecular magnetic resonance imaging (MRI) offers the potential to image some events at the cellular and subcellular level and many significant advances have recently been witnessed in this field. The introduction of targeted MR contrast agents has enabled the imaging of sparsely expressed biological targets in vivo.

While MRI is perhaps best known as the optimal imaging modality for the prostate and surrounding critical organ structures, it's application, and the application of the contrast agents necessary in order to effectively track and utilize this and related techniques, are not limited to cancer therapy. For example, MRI imaging, and its related imaging modalities, are being used in a variety of applications, including therapeutic applications (both treatment and monitoring), in angiography applications, for monitoring patient intravascular blood flow, in following drug delivery, and for in vivo MRI tracking techniques, such as the tracking of mesenchymal stem cells in peripheral nerve injuries using paramagnetic contrast agents.

Even though the intrinsic magnetic resonance imaging (MRI) contrast is much more flexible than in other clinical imaging techniques, the diagnosis of several pathologies requires the involvement of contrast agents (CAs) that can enhance the difference between normal and diseased tissues by modifying their intrinsic parameters. Imaging modalities which also require the use of contrast agents to be most effective in their therapeutic applications include in vivo near-infrared fluorescence (NIRF) imaging, magnetic resonance imaging (MRI), positron emission tomography (PET), computed tomography (CT), ultrasound (US), and photoacoustic imaging (PAI). In general, clinical and preclinical applications of contrast agents, particularly indirect contrast agents, have been identified for a broad spectrum of imaging applications. MRI CAs and related contrast agents are indirect agents because they do not become visible by themselves as opposed to other imaging modalities.

Nanoparticle-based contrast agents are also a developing approach, and are quickly becoming valuable and potentially transformative tools for enhancing medical diagnostics for a wide range of in vivo imaging modalities. Compared with conventional molecular-scale contrast agents, nanoparticles (NPs) promise improved abilities for in vivo detection and potentially enhanced targeting efficiencies through longer engineered circulation times, designed clearance pathways, and multimeric binding capacities.

MRI-CT fusion has been shown to improve postimplant quality assessment over CT alone, but this combined imaging approach has not been translatable to the community setting owing to inadequacies of fusing caused by imaging with different bladder and rectal filling, prostate volumetric differences between imaging modalities, and difficulties fusing the negative contrast of the seeds, strands of seeds, and needle tracks with the seeds visualized on CT scan. See, Crook, J., et al., "Interobserver Variation Inpostimplant Computed Tomography Contouring Affects Quality Assessment of Prostate Brachy therapy," *Brachytherapy,* 2002, Vol. 1(2), pp. 66-73 (2002).

The consequence of the current inadequate ultrasound and CT imaging is subjective dosimetric evaluation and poor quality assurance during and after brachytherapy. Poor-quality implants are of critical clinical importance because they lead to decreased cure rates and increased side effects after treatment. Therefore, there is a critical need for national standardization of prostate brachytherapy dosimetry. This effort may be achieved through the design of seed implants of improved design that incorporate high contrast imaging capabilities.

The inventions disclosed and taught herein are directed to new and improved contrast and imaging agents for use in a variety of medical imaging modalities, as well as seeds and strands containing such contrast agents, and the methods for manufacture and therapeutic use thereof.

BRIEF SUMMARY OF THE INVENTION

An imaging marker that includes a casing and a novel contrast agent comprising transition metal complexes, disposed within the casing is provided. The imaging markers may be placed in a strand, with or without a therapy seed, to produce a seeded strand useful for imaging and in connection with brachytherapy. Also provided is novel methodology to determine the appropriate range of concentration of the contrast agent so as to modulate the signal intensity as it relates to the activity of the therapy seed.

Methods of making the novel contrast agent, imaging marker, a therapy seed and the seeded strand, as well as delivery and extraction systems, are also provided. To make the seeded strand, at least one therapy seed and/or contrast marker is positioned in the bore of the strand. An optional spacer may be included in the seeded strand between markers or therapy seeds or between a marker and a therapy seed. The seeds, strands and imaging markers may also be used in connection with radioactive tracers.

In other aspects of the disclosure, methods of using the seeded strand by administering to a patient in need thereof the imaging marker, therapy seed, and/or seeded strand and imaging the patient to determine the position of the therapy seed and facilitating optimized radiation treatment are provided. Further, methodology for using MRI imaging agents as contrast markers and, more generally, as contrast agents/ markers of biocompatible devices (both therapeutic and non-therapeutic) is taught herein in order to identify the precise location of an implanted device in vivo to maximize the therapeutic ratio. Both known and novel contrast agents are taught for use in such novel methodologies.

Methods of using magnetic resonance imaging ("MRI") in the planning, treatment, and post-implant evaluation for brachytherapy for disease in various organs within a subject, including the prostate, head and neck, breast, lung, brain, GI malignancies, sarcomas and the like are also provided herein. These methods can utilize real-time MRI-guided procedures, including prostate brachytherapy.

In accordance with one embodiment of the present disclosure, a substantially non-toxic medical imaging contrast enhancing agent is described, the imaging agent comprising a complex of a metal ion having at least one unpaired electron and one or more of a ligand selected from the group consisting of halides, amino acids, amino acid derivatives, N-acyl-amino acids, chelating agents, polymers, or a combination thereof. In further accordance with this aspect, the metal ion is selected from the group consisting of chromium, manganese, iron, cobalt, and technetium. In accordance with one aspect, the metal ion is preferably cobalt, the halide ligands (if present) are chlorine, bromine, iodine, fluorine, or a combination thereof, and the amino acids (when present) are natural or unnatural amino acids selected from the group consisting of alpha-amino acids, beta-amino acids, gamma-amino acids, amino acid derivatives, N-alkylated amino acids, and combinations thereof. In further accordance with this embodiment, the composition of matter may comprise both a chelating agent and an excipient for administration to a patient for magnetic resonance imaging.

In accordance with yet another embodiment of the present disclosure, an imaging or contrast agent suitable for use in medical imaging modalities is described, the contrast agent comprising an octahedral cobalt compound wherein there contrast agent is water soluble and reduces a longitudinal relaxation time (T1) and a transverse relaxation time (T2) of water sufficient to produce a detectable contrast agent in medical imaging.

In accordance with a further embodiment of the present disclosure, a method of enhancing magnetic resonance contrast in a living subject is described, the method comprising administering internally to the subject an effective amount of a contrast agent which comprises a composition of the present disclosure, wherein the metal ion is selected from the group consisting of chromium, manganese, iron, cobalt, and technetium and the ligand is an amino acid. In further accordance with aspects of this embodiment, the contrast agent of this method comprises a compound of formula (I),

[CoCl$_2$(NAC)$_n$]    (I)

wherein n is the integer 1 or 2, and/or the concentration of cobalt chloride in water ranges from about 0.1 wt. % to about 10 wt. %, and the concentration of NAC in water ranges from about 0.1 wt. % to about 20 wt. %. In further aspects of the disclosure, the contrast or imaging agent is water soluble.

In accordance with a further embodiment of the present disclosure, methods for using the imaging agent compositions of the present disclosure for imaging a patient are described, the method comprising the steps of administering the magnetic resonance contrast enhancing agent compound to a patient; and taking images of the patient.

In yet another embodiment of the present disclosure, an imaging seed for implantation into a subject is described, wherein the seed is a combination product comprising a) a biocompatible and/or biodegradable encapsulating outer structure; b) one or more therapeutic components; c) a contrast, imaging, radiopaque, and/or other diagnostic material or marker suitable for use with one or more medical imaging modalities; and d) one or more structures to maintain location or orientation of the seed selected from the group consisting of one or more biodegradable structures effective to prevent migration upon implantation of the seed in tissue, and one or more biodegradable structures effective to maintain orientation in tissue, wherein the seed has a size and shape suitable for passing through the bore of a needle or catheter having an interior diameter ranging from less than about 2.7 mm (10 gauge) to about 0.16 mm (30 gauge). In further accordance with this aspect of the disclosure, the one or more therapeutic components is selected from the group consisting of hormone therapy drugs, immune modulators, cytotoxic agents, PSA-activated biotoxins, radiation sensitizers, and anti-inflammatory agents, or combinations thereof. In further accordance with this embodiment, the seed contains a contrast or imaging agent of such as a cobalt-based imaging agent (e.g., a cobalt-NAC compound) within the encapsulating structure. In yet another aspect of this embodiment, the seed further comprises an imaging, radiopaque, or other diagnostic agents or combinations thereof within the encapsulating structure, wherein the imaging agent is a radioisotope which is a low energy photon emitting radionuclide selected from the group consisting $^{131}$CS, $^{135}$I, $^{125}$I, $^{103}$Pd, $^{99}$Tc, $^{133}$Xe, and $^{169}$Yt. In still another aspect of this embodiment, the seed includes a radiopaque material selected from the group consisting of zirconium oxide, aluminum oxide, barium sulphate, sodium amidotrizoate and meglumine amidotrizoate, sodium diatrizoate, sodium calciumedetate, Iodixanol, and/or triphenyl bismuth, alone or in combination, as CT and/or fluoroscopic agents. In yet another aspect of the present disclosure, the seed provides substantially uniform dosimetry.

In accordance with further embodiments of the present disclosure, a method of manufacturing an imaging marker seed for use in association with medical imaging modalities upon implantation into a subject is described, the method comprising the steps of obtaining a hollow tube having a first proximal end and a second distal end; hermetically sealing the first proximal end of the tube to form an interior cavity; cutting the tube near the second distal end of the tube to adjust the overall marker seed length; injecting a contrast agent, a therapeutic agent, an imaging agent, a radioisotope, radiopaque material, or combination thereof into the interior cavity of the tube; and hermetically sealing the second, distal end of the tube. In accordance with aspects of this embodiment, the hollow tube is made of a biodegradable material, such as a biodegradable material selected from the group consisting of sodium polyacrylate, poly lactate, poly (D,L-lactide), poly (D/L-lactic acid), polyactide (PLA), polyglycolide, polyglycolic-lactic acid, and poly(L-lactide-co-glycolide). In further accordance with aspects of this embodiment, the tube has an inner diameter (ID) ranging from about 0.4 mm to about 6 mm, inclusive. In yet another aspect of this embodiment, the method further comprises forming one or more interior walls within the tube which are oriented substantially perpendicular to the longitudinal axis of the tube, and which separate the contrast agent from the therapeutic agent, radioisotope, and/or radiopaque material. In further aspects of the embodiment, the process is an automated process.

In yet another embodiment of the present disclosure, a contrast imaging system for use with one or more medical imaging modalities is described, the system comprising an elongated catheter sheath; an imager fixed to or received within the catheter sheath, wherein the imager acquires medical imaging modality images by emitting and receiving reflected imaging waves; a contrast lumen having a proximal end and a distal end, wherein the contrast lumen extends along the catheter sheath, has an exit port at its distal end, and contains one or more contrast agents within its body; an imaging system coupled to the imager for driving and receiving signals from the imager; and a controller coupled to the imaging system for synchronizing injection of a contrast agent and/or therapeutic agent from the exit port, with the acquisition of images by the imager thereafter. In further accordance with this aspect of the disclosure, the contrast agent is $CoCl_2$—NAC, $[CoCl_2(NAC)_1]^+$, $[CoCl_2(NAC)_2]$, or $CoCl_2$-glycine. In yet another aspect of this embodiment, the medical imaging modalities used with the system are selected from the group consisting of magnetic resonance imaging (MRI), nuclear imaging, computer tomography (CT), positron emission tomography (PET), single photon emission tomography (SPECT), and fluorescence imaging, as well as combinations thereof.

In accordance with a further embodiment of the present disclosure, a device for performing a biopsy on a patient in need thereof is described, the device comprising a needle sleeve, wherein the needle sleeve is adapted to allow a needle to pass therethrough, wherein the needle sleeve is visible under magnetic resonance imaging, wherein the needle sleeve is shaped for penetration of a patient during biopsy such that a distal end of the needle sleeve is capable of being guided; and a needle sleeve holder, wherein the needle sleeve holder allows an operator to position the needle sleeve in three dimensions. In further accordance with aspects of this embodiment, the needle sleeve is shaped for penetration of a patient during the biopsy such that a distal end of the needle sleeve is capable of being guided through the patient's perineum or rectum and into the patient's prostate. In yet another aspect of this embodiment, the needle sleeve comprises an outer tube and an inner tube penetrating through the entire length of the needle sleeve, wherein the hollow space between the outer tube and the inner tube contains a contrast agent, wherein the contrast agent allows the needle sleeve to be located under magnetic resonance imaging or other medical imaging modalities, and wherein the inner tube allows the biopsy needle to be inserted through the needle sleeve. In a further aspect of this embodiment, the device further comprises a positioning device, wherein the positioning device allows positioning of the patient with respect to the needle sleeve holder.

In another embodiment of the present disclosure, a catheter which is visible during the magnetic resonance imaging of body tissue of a patient is described, the catheter comprising a body having a proximal end, a distal end and at least one lumen extending therethrough, the body having a circumference and a longitudinal axis running between the distal and proximal ends, the body having a number of coaxial layers wherein at least one layer is formed of a biocompatible or biodegradable material and at least one layer comprises an amount of an imaging or contrast agent of the present disclosure to render at least a predetermined portion of the catheter visible during the magnetic resonance imaging of the patient's body tissue.

In a further embodiment of the present disclosure, a biocompatible polymer needle system for delivering a therapeutically useful material to the body of a subject and marking an intracorporeal site on or within the patient is described, the needle system comprising an elongated hollow shaft having a circumference and a longitudinal axis running therethrough; a proximal end; an opposite distal end; and an MRI detectable distal shaft portion which does not interfere with magnetic resonance imaging of tissue which is proximate thereto, wherein the distal shaft portion contains an MRI imaging or contrast agent according to the present disclosure. In further aspects of this embodiment, the needle system further includes a distal shaft portion having an effective amount of MRI detectable contrast agent so as to provide a clear, T1-weighted image within an outline of the distal shaft portion upon magnetic resonance imaging thereof. In further aspects of this embodiment, the needle system's MRI detectable contrast agent is selected from the group consisting of substantially non-toxic MRI detectable contrast agents containing cobalt, particularly an imaging or contrast agent selected from the group consisting of $CoCl_2$—NAC, $CoCl_2$-glycine, $CoCl_2$-EDTA, $CoCl_2$-DDTA, and combinations thereof. In further aspects of this embodiment, the distal shaft portion has an inner lumen and an MRI detectable mass within the inner lumen containing MRI detectable agent. In certain aspects, the mass within the inner lumen of the needle system is a gelled mass, such as a gelled mass is formed of an aqueous solution of a MRI contrast agent mixed with a hydrogel. In further aspects of this embodiment, the aqueous solution has an imaging or contrast agent selected from the group consisting of $[CoCl_2(NAC)_1]^+$, $[CoCl_2(NAC)_2]$, and $CoCl_2$-glycine, in a concentration of at least 0.00002 molar.

In accordance with further embodiments of the present disclosure, an imaging marker for implantation into a subject is described, wherein the marker is a combination product comprising a biocompatible and/or biodegradable encapsulating outer structure; a contrast, imaging, radiopaque, and/or other diagnostic material or marker suitable for use with one or more medical imaging modalities; and one or more structures to maintain location or orientation of the seed selected from the group consisting of one or more biodegradable structures effective to prevent migration upon implantation of the seed in tissue, and one or more biodegradable structures effective to maintain orientation in tissue. In further association with this aspect, the medical imaging modalities, upon implantation into a subject, include a MRI contrast agent and a CT marker or similar modality marker within a biodegradable or non-biodegradable, biocompatible casing or capsule. In further aspects of this embodiment, the imaging marker further comprises a radiopaque material selected from the group consisting of zirconium oxide, aluminum oxide, barium sulphate, sodium amidotrizoate and meglumine amidotrizoate, sodium diatrizoate, sodium calciumedetate, Iodixanol, and/or triphenyl bismuth, alone or in combination, as CT and/or fluoroscopic agents.

The foregoing has outlined rather broadly the features of the invention in order that the detailed description of the invention that follows may be better understood. Additional features and advantages of the invention will be described hereinafter, which form the subject of the claims of the invention.

BRIEF DESCRIPTION OF THE SEVERAL VIEWS OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1A:
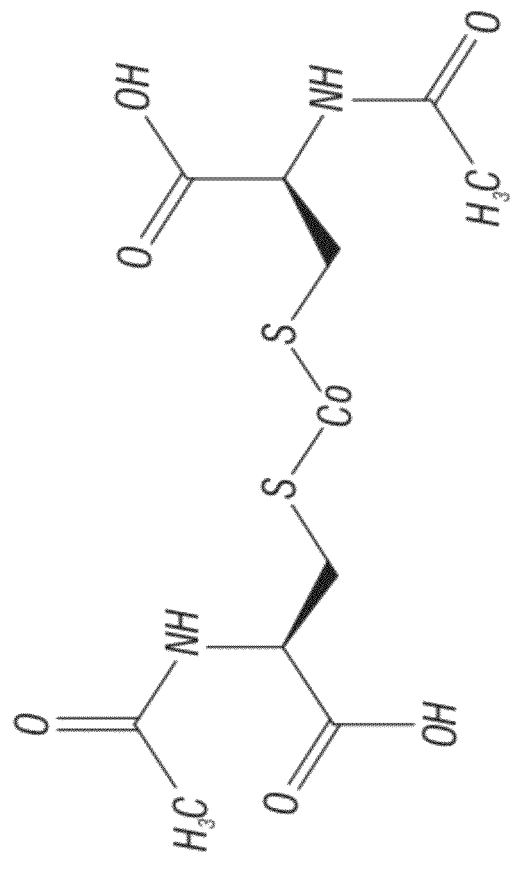
FIG. 1A illustrates putative structural representations of exemplary cobalt-based contrast agents, including a cobalt-NAC complex, in accordance with aspects of the present disclosure. The left image is that of $CoCl_2$—NAC (molecular formula: $C_5H_7CoNO_3S$; F.W. 220.11); the right image is that of $CoCl_2$—$NAC_2$ (molecular formula: $C_{10}H_{16}CoN_2O_6S_2$; F.W. 383.307).
Figure 1A:
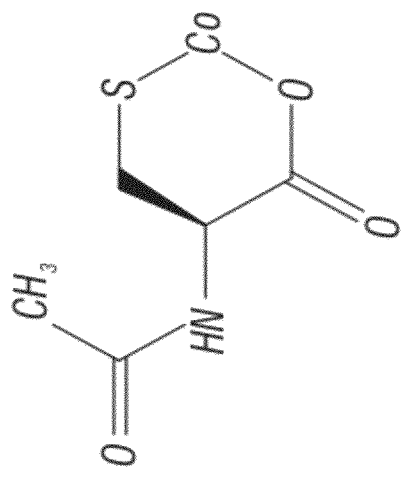

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

DEFINITIONS

The following definitions are provided in order to aid those skilled in the art in understanding the detailed description of the present invention. Units, prefixes, and symbols may be denoted in their SI accepted form. Unless otherwise indicated, nucleic acids are written left to right in 5' to 3' orientation, and amino acid sequences are written left to right in amino to carboxy orientation, respectively. Numeric ranges are inclusive of the numbers defining the range and include each integer within the defined range. Amino acids may be referred to herein by either their commonly known three letter symbols (e.g., Pro for proline), or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

"Non-naturally occurring amino acid", as used herein, refers to any amino acid that is not found in nature. Non-natural amino acids include any D-amino acids (described below), amino acids with side chains that are not found in nature, and peptidomimetics. Examples of peptidomimetics include, but are not limited to, β-peptides, γ-peptides, and δ-peptides; oligomers having backbones which can adopt helical or sheet conformations, such as compounds having backbones utilizing bipyridine segments, compounds having backbones utilizing solvophobic interactions, compounds having backbones utilizing side chain interactions, compounds having backbones utilizing hydrogen bonding interactions, and compounds having backbones utilizing metal coordination. All of the amino acids in the human body, except glycine, are either right-hand or left-hand versions of the same molecule, meaning that in some amino acids the positions of the carboxyl group and the R-group are switched. Nearly all of the amino acids occurring in nature are the left-hand versions of the molecules, or the L-forms. Right-hand versions (D-forms) are not found in the proteins of higher organisms, but they are present in some lower forms of life, such as in the cell walls of bacteria. They also are found in some antibiotics, among them, streptomycin, actinomycin, bacitracin, and tetracycline. These antibiotics can kill bacterial cells by interfering with the formation of proteins necessary for viability and reproduction.

"Polypeptide", "peptide", and "oligopeptide" refers generally to peptides and proteins having more than about ten amino acids, preferably more than 9 and less than 150, more preferably less than 100, most preferably between 9 and 51 amino acids. The polypeptides can be "exogenous," meaning that they are "heterologous," i.e., foreign to the host cell being utilized, such as human polypeptide produced by a bacterial cell. Exogenous also refers to substances that are added from outside of the cells, not endogenous (produced by the cells). A peptide encompasses organic compounds composed of amino acids, whether natural or synthetic, and linked together chemically by peptide bonds. The peptide bond involves a single covalent link between the carboxyl (oxygen-bearing carbon) of one amino acid and the amino nitrogen of a second amino acid. Small peptides with fewer than about ten constituent amino acids are typically called oligopeptides, and peptides with more than ten amino acids are termed polypeptides. Compounds with molecular weights of more than 10,000 Daltons (50-100 amino acids) are usually termed proteins.

As used herein, the term "CT" or "CT scan" refers to computer-assisted tomographic scanning. Typical CT scanning involves the injection of a contrast agent or dye into a subject, followed by the use of X-rays to produce detailed pictures of the target anatomy, from which diagnosis and monitoring of therapy implants may be done.

"Ultrasound", "ultrasonic radiation", or "US" as used herein refers to mechanical (including acoustic or other terms of pressure) waves in a medium in the general frequency range from about 20 kHz to about 4 GHz or greater.

The term "marker", as used herein, includes fiducial markers, and refers to a composition, material, feature, image structure, or subobject present in images that is imageable by an appropriate imaging modality, including MRI, CT, US, and combinations thereof, for use in image analysis, matching, coordinate interreferencing or registration of the images and creation of a composite image.

The term "subject", as used herein, refers to any animal (i.e., vertebrates and invertebrates) including, but not limited to humans and other primates, rodents (e.g., mice, rats, and guinea pigs), lagamorphs (e.g., rabbits), bovines (e.g. cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc. It is not intended that the term be limited to a particular age or sex. Thus, adult and newborn subjects, as well as fetuses, whether male or female, are encompassed by the term.

"Biodegradable", as used herein, means, with respect to a material, that the material is capable of undergoing and/or does undergo physical, chemical, thermal and/or biological degradation within a biological system as measured according to standard decomposition rate testing standards.

The term "biocompatible", as used herein, refers to an object, material, or composition that is substantially non-toxic and non-immunogenic. More broadly, biocompatibility is the ability of a material to perform with an appropriate host response in a specific situation. Therefore, biocompatibility represents a global statement on how well body tissues interact with a material and how this interaction meets the designed expectation for a certain implantation purpose and site [See, Von Recum, A. F., et al., "Introduction: Biomaterials and Biocompatibility.", in: *Handbook of Biomaterials Evaluation Scientific, Technical and Clinical Testing of Implant Materials*. von Recum, A. F., Ed.; Taylor & Francis, 1999: pp. 1-8]. Hence, biocompatibility is a relative rather than an absolute concept, which depends to a large degree on the ultimate expectation of the material.

The term "substantially non-toxic", as used herein, means a surface or material this is substantially non-hemolytic and substantially, meaning that the surface, material or composition does not leach a sufficient amount of the imaging agent or other compositions as described herein to generate a toxic reaction in a host from the released material.

"Substantially non-toxic", as used herein, means a surface, material or composition that is substantially non-hemolytic and substantially non-cytotoxic.

The term "therapeutically effective amount", as used herein, refers to an amount of an antibody, polypeptide, or other drug effective to "treat" a disease or disorder in a subject or mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic.

The term "NAC", as used herein, refers to N-acetyl-cysteine, in either the L-or D-form, as represented by the structure I shown below, as well as rotomers, conformers, solvates, hydrates, and derivatives thereof, or a pharmaceutically acceptable salt, solvate, or ester thereof,

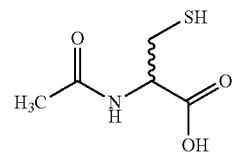

wherein the wavy line used as a bond "〜", denotes a bond which can be either the E-or Z-geometric isomer. When not used as a bond, the wavy line indicates the point of attachment of the particular substituent, as appropriate.

The term "CT", as used herein, refers to computed tomography imaging using a radioactive beam, such as the type that is typically carried out to investigate the size and position of a focus. In such imaging, a marker is used so that changes in position of the marker and the focus displayed on laminagram images are read and reconfigured to specify the position, size, topography, and the like, of a concerned focus.

The term "MRI" is used herein as an abbreviation for "magnetic resonance imaging". The terms "MRI" and "magnetic resonance imaging" are used interchangeably in the following disclosure. The terms "MRI magnetic environment" and "MRI environment" are used to refer to the powerful magnetic field created by MRI magnets which are a component of MRI systems. The MRI magnetic environment typically contains all or part of a patient's body when that body undergoes MRI imaging. Further, it is expected that during the life of this patent many relevant techniques for magnetic resonance imaging will be developed, and the scopes of the terms "MRI" and "magnetic resonance imaging" are intended to include all such new technologies a priori.

As used herein, the term "about" refers to +/−10%.

The term "chelating agent" as used herein refers to any organic or inorganic compound that will bind to a metal ion having a valence greater than one. "Chelating agents" include, but are not limited to, organic chelating agents such as ethylenediamenetetracetic acid (EDTA), triethylene tetramine dihydrochloride (TRIEN), ethylene glycol-bis(β-aminoethyl)ether-N,N,N',N'-tetracetic acid (EGTA), diethylenetriamin-pentaacetic acid (DPTA), and triethylenetetramine hexaacetic acid (TTG), deferoxamine, Dimercaprol, edetate calcium disodium, zinc citrate, penicillamine succimer and Editronate, or any other chelating agent that will chelate divalent ions such as $Co^{2+}$ and which are biologically acceptable to mammals.

The term "pendant linker group", as used herein, relates to moieties which are attached to the chelating group, and which have at least one functional group which is capable of covalently binding to targeting molecules. Where pendant linkers or chelating agents have a plurality of such functional groups, they may be the same or different. When the chelating moiety is macrocyclic, the pendant moiety may be attached to any annular atom. For example, when the chelating moiety is a polyazamacrocycle, the pendant group may be attached to an annular carbon atom or an annular nitrogen atom. When the pendant group is attached to an annular nitrogen atom, the compound may be referred to as an N-substituted polyazamacrocycle.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts Properties, Selection, and Use" (Wiley VCH, Zunch, Switzerland: 2002). The salts can be prepared in situ during the final isolation and purification of the compounds of the present invention or separately by reacting a free base function with a suitable organic acid. Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, flimarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid.

The phrase "pharmaceutical composition" refers to a formulation of a compound and a medium generally accepted in the art for the delivery of the biologically active compound to mammals, e.g., humans. Such a medium includes all pharmaceutically acceptable carriers, diluents or excipients therefore.

The phrase "pharmaceutically acceptable carrier, diluent or excipient" as used herein includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

The terms "treating" or "treatment" as used herein cover the treatment of the disease or condition of interest, e.g., tissue injury, in a mammal, preferably a human, having the disease or condition of interest, and includes: (i) preventing the disease or condition from occurring in a mammal, in particular, when such mammal is predisposed to the condition but has not yet been diagnosed as having it; (ii) inhibiting the disease or condition, i.e., arresting its development; (iii) relieving the disease or condition, i.e., causing regression of the disease or condition; or (iv) relieving the symptoms resulting from the disease or condition.

As used herein, the terms "disease," "disorder," and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The term "water-insoluble" encompasses the terms sparingly water-soluble, slightly or very slightly water-soluble, as well as practically or totally water-insoluble compounds [see, Remington: The Science and Practice of Pharmacy, vol. I, pp. 194-195 (Gennaro, ed., 1995)]. As used herein, a compound is water-insoluble for the purposes of this invention if it requires at least 30 parts solvent (e.g., water or saline) to dissolve one part solute (Id.). In accordance with the present disclosure, the term "water-insoluble" also encompasses oil- or lipid-soluble, as well as substantially oil- or lipid soluble.

As used herein, the term "%" when used without qualification (as with w/v, v/v, or w/w) means % weight-in-volume for solutions of solids in liquids (w/v), % weight-in-volume for solutions of gases in liquids (w/v), % volume-in-volume for solutions of liquids in liquids (v/v) and weight-in-weight for mixtures of solids and semisolids (w/w), such as described in Remington's Pharmaceutical Sciences [Troy, David B., Ed.; Lippincott, Williams and Wilkins; 21st Edition, (2005)].

The term "drug" as used in conjunction with the present disclosure means any compound which is biologically active, e.g., exhibits or is capable of exhibiting a therapeutic or prophylactic effect in vivo, or a biological effect in vitro.

As used herein, the term "androgen inhibition activity" means the ability to inhibit the activity of an androgen, which can be achieved by, for example, activities directed towards the androgen, the androgen receptor, or a combination of the androgen and androgen receptor. Such activities include, for example, decreasing androgen synthesis or concentration (e.g., decreasing transcription, translation or decreasing the half-life of a transcript or post-translational product), AR downregulation and/or AR modulation, and preventing the binding of an androgen to an androgen receptor or competing with an androgen and its binding to an androgen receptor. Activities also include anti-cancer activities, as influenced by known androgen receptor down-regulating agents (ARDAs).

In discussion of the various figures described hereinbelow, like numbers refer to like parts.

DETAILED DESCRIPTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created novel contrast and imaging markers and seeds for use in MRI imaging, CT imaging, and similar biological imaging modalities, as well as in directed drug delivery applications, and the associated methods of manufacturing and therapeutically using such markers.

These novel MRI imaging agents as described herein exhibit several advantages over the presently used imaging and contrast agents, many of which are gadolinium-based, one of the most notable of which is enhanced patient safety. Safety is a primary concern with contrast agents used for MRI. For example, contrast agents based on gadolinium (e.g., gadoterate meglumine (Gd-DOTA) [Magnescope® in Japan, Dotarem® in other countries]) have been linked to nephrogenic systemic fibrosis, wherein some patients with kidney disease have had gadolinium-based reactions when such Gd-based contrast agents are used, the reactions leading to a potentially fatal condition termed "nephrogenic systemic fibrosis" (NSF), also known as nephrogenic fibrosing dermopathy (NFD), which can lead to gadolinium renal failure (see, Martin, D. R., Eur. J. Radiol., Vol. 66(2), pp. 220-224 (2008)). Other health concerns which have been reported in association with the use of standard MRI contrast agents include contrast-agent-induced nephrotoxicity, cardiotoxicity, adverse drug reactions, and the like. The low incidence of adverse reactions (<1%) and the absence of serious adverse reactions associated with the use of the new contrast agents described herein suggest that these cobalt-based MRI contrast agents are very well tolerated in patients, and the use of cobalt-based MRI-enhancing contrast mediums in the clinical practice setting appears to be safe and effective.

Contrast Agents

A. Composition.

MRI is superior to ultrasound and CT scans (Computerized Axial Tomography, also referred to as "CAT scans") in prostate gland delineation and surrounding critical organs like the rectum, urethra, and neurovascular structures. However, to date, individual therapy seeds and other medical devices are difficult to locate and/or identify using MRI, because the needle tracks, spacers, and seeds (particularly titanium seeds) appear as negative contrast images. See, for example, Frank, S. J., et al., "A Novel MRI Marker For Prostate Brachytherapy," *International Journal of Radiation Oncology Biology Physics*, 2008, 71(1):5-8.

Figure 1B:
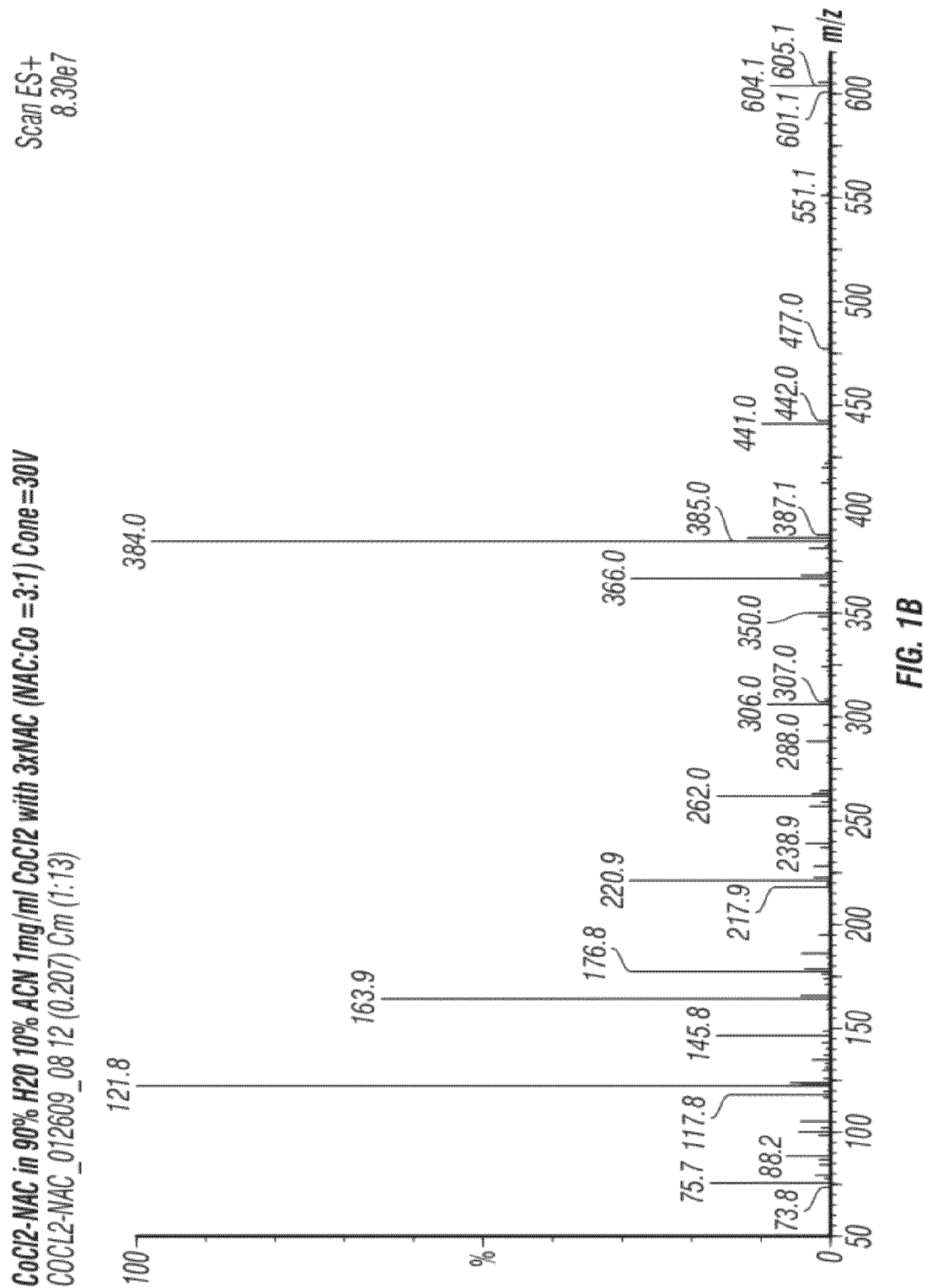
FIG. 1B illustrates a full scan MS spectrum of a 1% $CoCl_2$—NAC contrast agent composition in accordance with aspects of the present disclosure.
Figure 1C:
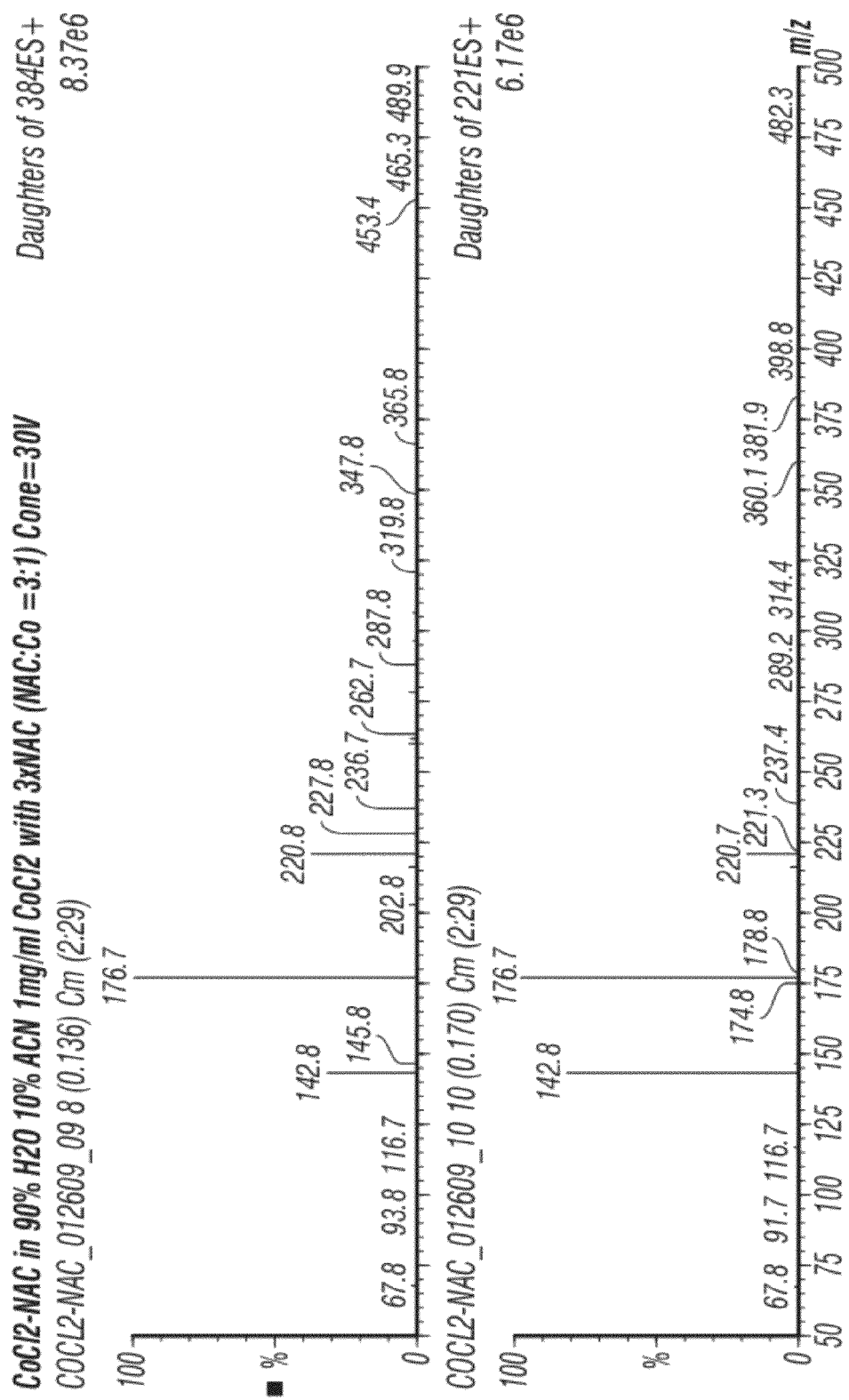
FIG. 1C illustrates daughter CID fragmentation mass spectral ion scans of the 1% $CoCl_2$—NAC solution of FIG. 1B.
Figure 1D:
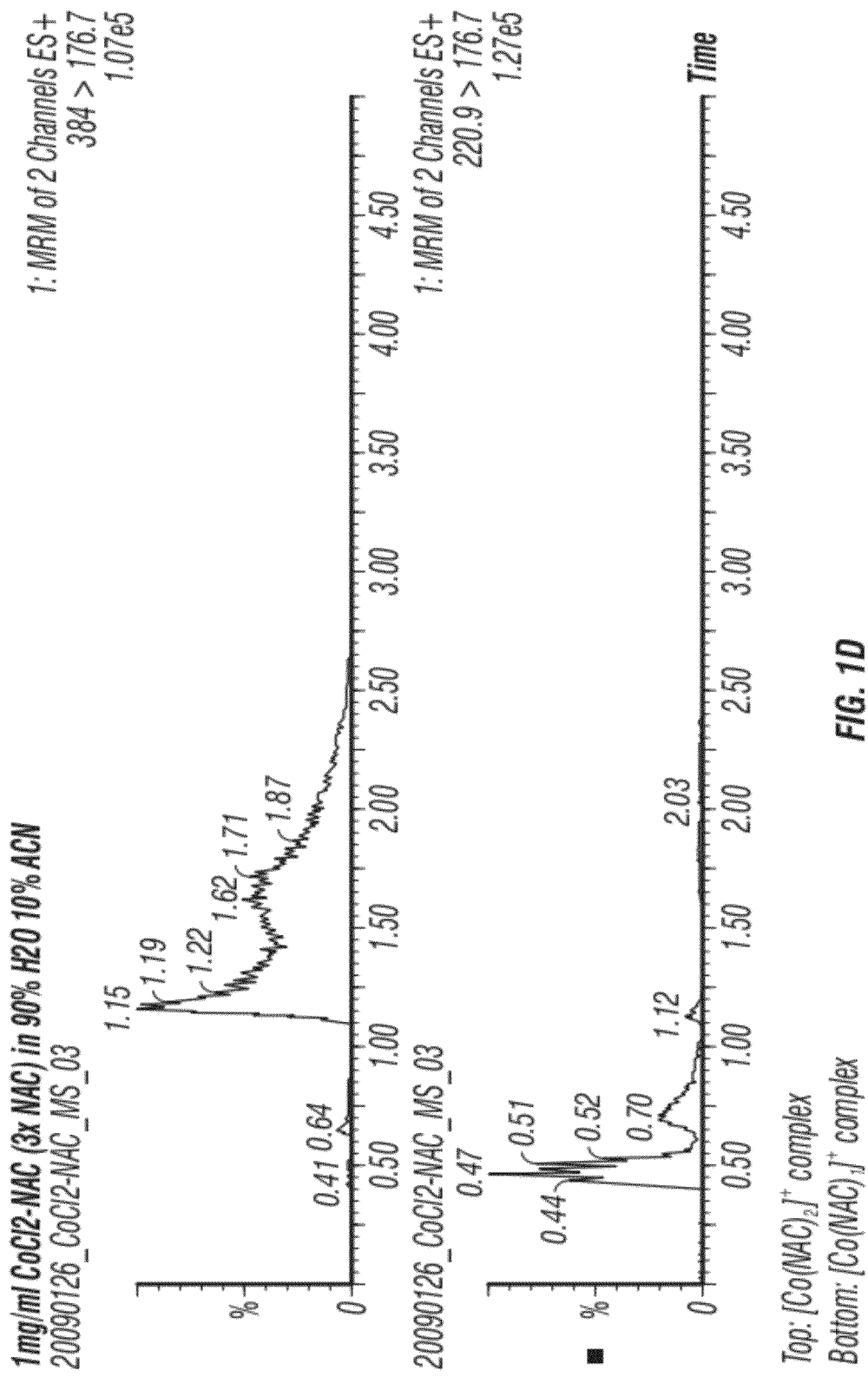
FIG. 1D illustrates an exemplary LC/MS/MS chromatogram of an exemplary $CoCl_2$—NAC complex in accordance with the present disclosure.
Figure 1E:
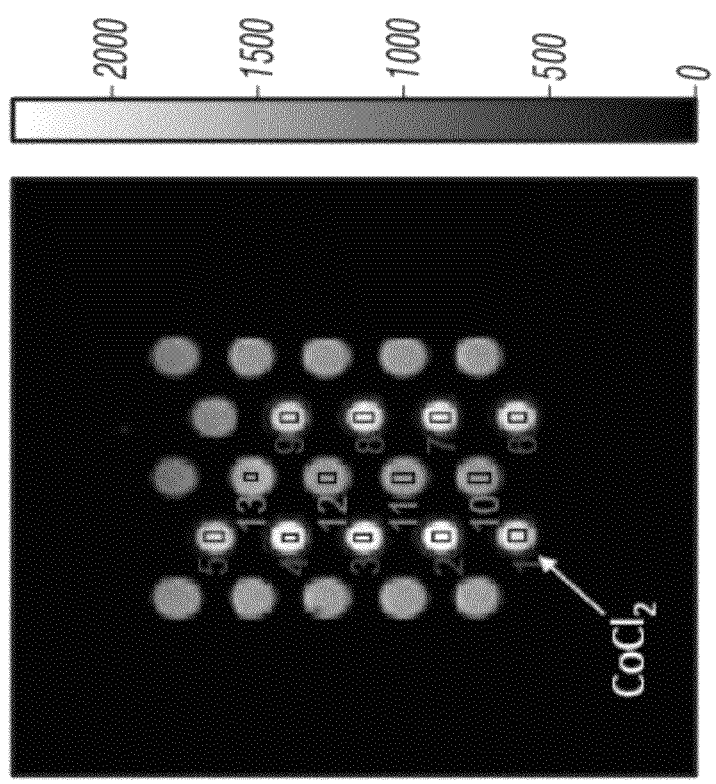
FIG. 1E illustrates exemplary magnetic resonance images of $CoCl_2$ and $CoCl_2$—NAC solutions with different concentrations (in wt. %).
Figure 2B:
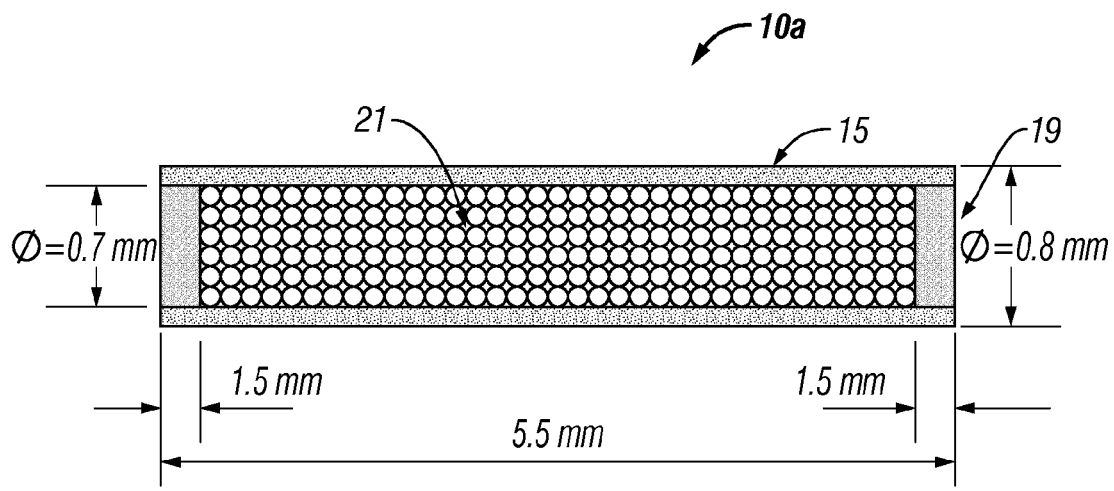
FIG. 2B illustrates an exemplary schematic diagram of an imaging marker in accordance with the present disclosure, fabricated by using $CoCl_2$—NAC encapsulated within microsphere.
Figure 2A:
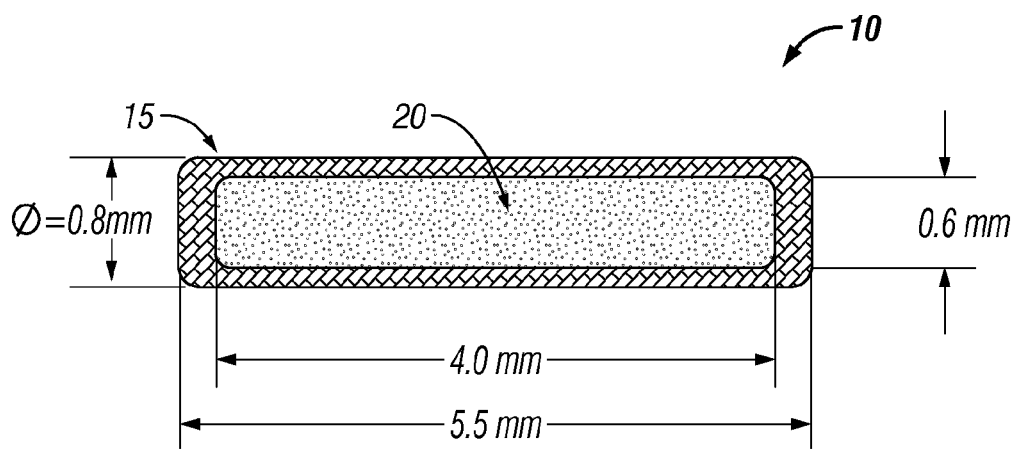
FIG. 2A illustrates a schematic representation of an exemplary imaging marker of the present disclosure within a casing.

In the present disclosure, and in reference to FIGS. 1-7, an imaging marker 10 (or 10a, etc.) is provided that can be simply a contrast agent 20 (in solid or hydrogel form), or, with reference to FIGS. 2A and 2B, the imaging marker 10 can be a medical device that has a casing 15 with the contrast agent 20 disposed within the casing 15 in a variety of configurations, as shown in FIGS. 2-7. The contrast agent 20, also a type of medical device, is sometimes referred herein to as an "MR contrast agent" or "MRI contrast agent" and is useful alone as an imaging marker 10, for example in intravenous applications. The contrast agent 20 importantly renders a contrast marker or similar marker MRI-visible. The imaging marker 10 is useful for a variety of multi-functional applications, including the accurate identification of an implanted radioactive therapy seed and other medical devices in vivo, and facilitates the establishment of, for example, MRI-based brachytherapy dosimetry for prostate brachytherapy and other brachytherapies and related therapeutic methods as will be discussed in more detail herein.

In accordance with the present disclosure, the contrast agent 20 is a cobalt-based compound, preferably a cobalt(II) chloride based compound, although cobalt(II) chloride by itself may be used as well. For example, the contrast agent 20 may be cobalt(II) chloride, or a complex of cobalt(II) chloride and one or more amino acids, or a complex of cobalt (II) chloride and one or more chelating agents, or combination thereof (e.g, cobalt (II) chloride, at least one amino acid such as a cysteine-based amino acid (aa), and at least one chelating agent, such as an N,N'-bidentate ethylenediamine (en) ligand), having a general structure $[Co(en)_2(aa)]^{2+}$). In accordance with other aspects of the present disclosure, the contrast agent 20 may be a cobalt complex of cobalt (II) chloride and one or more polymers, or a cobalt complex of cobalt (II) chloride, one or more polymers, and an amino acid or chelating agent. The cobalt (II) chloride complexes useful as contrast agents in accordance with the present disclosure preferably exhibit reduced toxicity and maximize fecal and urinary excretion, as detailed, for example, by Llobet (*Arch. Toxicol.* Vol. 58(2), pp. 278-281 (1986)) and in "Toxicological Profile for Cobalt", from the US. Department of Health and Human Services, April 2004. Typically, in accordance with one aspect of the present disclosure, the contrast agents of the present invention comprise cobalt (II) chloride in a concentration ranging from about 0.1 to about 10 wt. % of $CoCl_2$, and from about 0.1 to about 20 wt. % of the associated complexing agent, e.g., from about 0.1 wt. % to about 20 wt. % of one or more amino acids (such as N-acyl cysteine, NAC), chelating agents, polymers, and the like.

Amino acids suitable for use in forming cobalt (II) chloride contrast agent compositions 20 in accordance with the present disclosure include natural amino acids, un-natural amino acids, and amino acid derivatives, in either the L or D configuration, as well as mixtures of rotamers as appropriate. Exemplary natural amino acids suitable for use in the instant compositions include alanine, arganine, asparagines, cysteine, glycine, glutamine, leucine, isoleucine, methionine, proline, phenylalanine, serine, tyrosine, and valine. Exemplary un-natural amino acids suitable for use in forming cobalt (II) chloride complexes include beta amino acids, gamma amino acids, N-methyl amino acids, N-alkyl amino acids, and other amino acids which are not considered to be "natural", including ornithine, homo-cysteine, norvaline, and the like. In accordance with a preferred embodiment of the present disclosure, the contrast agent is a complex of cobalt (II) chloride ($CoCl_2$) and N-acetyl-(L)-cysteine (NAC) dissolved in water, as illustrated generally having the structures and spectrographic features shown in FIGS. 1A-1E, and referred to herein as the $CoCl_2$—NAC contrast agent. Exemplary cobalt-amino acid compositions suitable for use herein include, but are not limited to, compositions of formula (1) below,

$$[CoCl_m(NAC)_n] \quad (1)$$

where m=0, 1, or 2, and n=1-2, and the concentration of cobalt chloride in NAC in water can be varied as $CoCl_2$, from about 0.1 wt % to about 10 wt. % (inclusive), and NAC in a concentration in water from about 0.1 wt. % to about 20 wt. % (inclusive).

Chelating agents suitable for use in forming cobalt (II) chloride contrast agent compositions 20 in accordance with the present disclosure include macrocycles, linear, or branched moieties. Examples of macrocyclic chelating moieties include but are not limited to polyaza- and polyoxamacrocycles. Examples of polyazamacrocyclic moieties include those derived from compounds such at 1,4,7,10-tetraazacyclododecane-N,N',N'',N'''-tetraacetic acid (herein abbreviated as DOTA); 1,4,7,10-tetraazacyclotridecane-N,N',N'',N'''-tetraacetic acid (herein abbreviated as TRITA); 1,4,8,11-tetraazacyclotetradecane-N,N',N'',N'''-tetraacetic acid (herein abbreviated as TETA); and 1,5,9,13-tetraazacyclohexadecane-N,N',N'',N'''-tetraacetic acid (hereinafter abbreviated as HETA). Examples of linear or branched chelating moieties include but are not limited to those derived from compounds such as ethylenediaminetetraacetic acid (herein abbreviated as EDTA), ethyleneglycol-bis-(beta-aminoethylether)-N,N-tetracetic acid (hereinafter abbreviated EGTA), ethylenediamine-N,N'-bis(2hydroxy-phenyl)acetic acid (hereinafter abbreviated EDDHA), hydroxyethyl ethylenediamine triacetic acid (hereinafter abbreviated HEDTA), diethylenetriaminepentaacetic acid (herein abbreviated as DTPA), 2,3-dimercapto-1-propanol (hereinafter abbreviated BAL), 2,3-dimercaptopropane-1-sulphonic acid (hereinafter abbreviated DMPS), 2,3-dimercaptosuccinic acid (hereinafter abbreviated DMSA), meso-DMSA, rac-DMSA (racemic DMSA), esters of DMSA such as diisopropyl DMSA, N-acetyl-D-penicillamine (hereinafter abbreviated NAPA), DFO (deferoxamine), LI (deferiprone, 1,2-dimethyl-3-hydroxyprid-4-one), LINAII (1-allyl-2-methyl-3-hydroxypyrid-4-one), Trientine (triethylenetetraamine), mi-ADMS (monoisoamyl meso-2,3-dimercaptosuccinic acid), sodium N-benzyl-D-glucamine-N-carbodithioate (hereinafter abbreviated BGDTC), N-methyl-N-dithiocarboxy-D-glucamine (hereinafter abbreviated MGDTC), N-(4-methoxybenzyl)-D-glucamine carbodithioate monohydrate (hereinafter abbreviated MeOBGDTC), carbodithioates such as disodium N,N'-diglucosyl-1,9-nonane-diamine-N,N'-biscarbodithioate (hereinafter abbreviated C9G2DTC) and sodium diethylcarbodithioate (hereinafter abbreviated DDTC), (hereinafter abbreviated DPA), CDTA, CP502, and dexrazoxane, the structures and details of the chemistry of which are described by Blanusa, et al. [*Current Medicinal Chemistry*, Vol. 12 (23), pp. 2771-2794 (2005)].

The cobalt (II) chloride complexes of the present disclosure may also be a complex of cobalt (II) chloride and one or more polymers. Exemplary polymers suitable for use in forming such complexes include but are not limited to one or more water-soluble polymers and/or water-swelling polymers. Examples of the water-soluble or water-swelling polymer include plant polymers such as gum Arabic, tragacanth gum, arabinogalactan, locust bean gum (carob gum), guar gum, karaya gum, carrageenan, pectin, agar, quince seed (i.e., marmelo), starch from rice, corn, potato or wheat, algae colloid, trant gum and locust bean gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, and carboxyvinyl polymer; polyoxyethylene polymers; polyoxyethylene/polyoxypropylene copolymers; acrylic polymers such as sodium polyacrylate, polyethyl acrylate, and polyacrylamide; synthetic water-soluble polymers such as polyethyleneimine and other kind of cationic polymers; semi-synthetic water-soluble polymers such as silicone-modified pulllanIn accordance with one preferred aspect of the present disclosure, the contrast agent 20 is a complex of $CoCl_2$ and sodium polyacrylate ($[-CH_2-CH(CO_2Na)-]_n$), in an amount ranging from about 1 wt. % to about 10 wt. %, inclusive, based on total weight of the contrast agent.

In further accordance with the present disclosure, the contrast agent 20 may be in liquid form, as described above, or may optionally and equally acceptably be in gel (e.g., hydrogel) or solid form within a polymer casing 15. This is illustrated generally in FIG. 2A, while FIGS. 2B-7 illustrate various alternative embodiments and arrangements of the contrast agent within polymer casing 15 in combination with various moieties. As shown in FIG. 2A, marker 10 may comprise a polymer coating 15 with a contrast agent 20, such as a $CoCl_2$—NAC contrast agent, contained therein. Marker 10 may have varied dimensions, as controlled primarily by the application of the marker. For example, the marker may have an outer diameter ranging from about 0.3 mm to about 1 mm, an inner diameter ranging from about 0.1 mm to about 0.8 mm, and an overall length ranging from about 3 mm to about 10 mm. As example marker dimensions, the outside diameter can be about 0.8 mm, the inside diameter can be about 0.6, the outside length of the marker 10 can be about 5.5 mm, and inside length can be about 4.0 mm. Other suitable dimensions for the markers and strands made from such markers are described, for example, in International Patent Publication No. WO 2009/009760 A1.

The casing 15 for the markers may be made of any number of suitable materials, including biocompatible and non-biodegradable materials, particularly biocompatible or non-biocompatible polymers. The non-biodegradable/-biocompatible materials suitable for use in forming casing 15 include polymers selected from the group consisting of polyether ether ketone (PEEK), polyether ketone (PEK), polyaryl ether ketones, polymethyl methacrylate (PMMA), polynorbornene, polycaprolactone, a polyenes, nylons, polycyclooctene (PCO), blends of PCO and styrene-butadiene rubber, polyvinyl acetate/polyvinylidinefluoride (PVAc/PVDF), blends of PVAc/PVDF/polymethylmethacrylate (PMMA), polyurethanes, styrene-butadiene copolymers, polyethylene, trans-isoprene, blends of polycaprolactone and n-butylacrylate, POSS (polyhedral oligomeric silsesquioxane diol) polyurethane polymers, PVC, plasticized PVC, and polystyrene, as well as blends thereof (e.g., a PEK/PEEK mixture).

Alternatively, and in accordance with aspects of the present disclosure, the casing 15 for encapsulating the imaging marker 10 is both biocompatible and biodegradable. As used herein, reference to "biologically degradable," "biologically erodable," "biologically resorbable," and "biologically absorbable" casings 15 and/or polymers forming such contrast agent casings, is understood that after the process of degradation, erosion, absorption, or resorption has been completed, no coating will remain on the stent. In some embodiments, traces or residues may remain. The terms "degradable," "biodegradable," or "biologically degradable" are intended to broadly include biologically degradable, biologically erodable, biologically absorbable, and biologically resorbable coatings, casings and/or polymers. In accordance with selected aspects of the present disclosure, the term biodegradable can indicate that the casing 15 has a half-life which is time-dependant on the isotope that is used, e.g., the half-life of Cs-131 (when an isotope is used). Suitable compounds for use as biodegradable, biocompatible casings 15 include but are not limited to synthetic polymers such as polycaprolactone, polyhydroxyacids such as poly(lactic acid), which includes poly(D,L-lactic acid) (DLPLA), poly (D-lactic acid) (DPLA) and poly(L-lactic acid) (LPLA); poly (D,L-lactide); poly(L-lactide); polyglycolide; polyglycolic-lactic acid; poly(dioxanone); poly(L-lactide-co-glycolide); poly(D, L-lactide-co-glycolide); and poly(L-lactide-co-D, L-lactide).

Additional biodegradable polymers that can be used in accordance with the present disclosure include synthetic polymers such as polycaprolactone, poly(hydroxy butyrate), polyglycolide, poly(diaxanone), poly(hydroxy valerate), polyorthoester; copolymers such as poly (lactide-co-glycolide), polyhydroxy (butyrate-co-valerate), polyglycolide-co-trimethylene carbonate; polyanhydrides; polyphosphoester; polyphosphoester-urethane; polyamino acids; polycyanoacrylates; polyanhydrides such as (poly(bis(p-carboxyphenoxy) propane anhydride, poly(bis(p-carboxy) methane anhydride), copolymer of poly-carboxyphenox-ypropane and sebacic acid); polyorthoesters; polyhydroxyalkanoates (polyhydroxybutyric acid); poly (isobutylcyanoacrylate). biomolecules such as fibrin, fibrinogen, cellulose, starch, collagen and hyaluronic acid; and mixtures of the foregoing. Biostable materials that are suitable for use in this invention include polymers such as polyurethane, silicones, polyesters, polyolefins, polyamides, polycaprolactam, polyimide, polyvinyl chloride, polyvinyl methyl ether, polyvinyl alcohol, acrylic polymers and copolymers, polyacrylonitrile, polystyrene copolymers of vinyl monomers with olefins (such as styrene acrylonitrile copolymers, ethylene methyl methacrylate copolymers; ethylene vinyl acetate), polyethers, rayons, cellulosics (such as cellulose acetate, cellulose nitrate, cellulose propionate, etc.), parylene and derivatives thereof; and mixtures and copolymers of the foregoing.

Other examples of suitable biodegradable materials for making the casing 15 include open cell polylactic acid; co-polymers of a fatty acid dinner and sebacic acid; poly(carboxyphenoxy) hexane; poly-1,4-phenylene dipropionic acid; polyisophthalic acid; polydodecanedioic acid; poly(glycol-sebacate) (PGS); or other polymers described below. See, e.g., BIOMATERIALS ENGINEERING AND DEVICES: HUMAN APPLICATIONS: FUNDAMENTALS AND VASCULAR AND CARRIER APPLICATIONS, Donald L. Wise et al. (eds), Humana Press, 2000; and, BIOMATERIALS AND BIOENGINEERING HANDBOOK, Donald L. Wise, Marcel Dekker, 2000.

These polymers can be obtained from a variety of commercial sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or they can be synthesized from monomers obtained from these or other suppliers using standard techniques.

In addition to synthetic polymers, natural polymers may also be used in forming the casing 15. In one preferred embodiment, the natural polymers are biodegradable. For example, tissue such as connective tissue from the walls of blood vessels or extracellular matrix may be used as a biodegradable carrier for delivery of contrast agents, radiation or another therapeutic substance. Such tissue may be autologous, heterologous, engineered, or otherwise modified so long as it is biocompatible with the target tissue. A patient may donate his own tissue to serve as a carrier for the therapeutic substance and/or radionuclide. Other tissues or natural polymers may serve as the degradable carrier matrices, such as, polysaccharides such as starch and dextran, proteins such as collagen, fibrin (see, for example, Perka, et al., Tissue Eng., Vol. 7, pp. 359-361 (2001) and Senderoff, et al., J. Parenteral Sci., Vol. 45, pp. 2-6 (1991)), and albumin (see, for example, U.S. Pat. No. 5,707,644), elastin-like peptides, lipids, and combinations thereof. These materials can be derived from any of the sources known to those skilled in the art, including the patient's own tissues or blood.

In accordance with further aspects of the present disclosure, the casing or encapsulating means 15 may be in the form of microspheres. In accordance with the present invention, an attempt was made to prepare polymeric microspheres of $CoCl_2$—NAC in aqueous solution for formation of MRI markers for imaging. The different biocompatible and bioabsorbable polymers are the preferred choice for such encapsulation. For example, poly(D,L-lactide-co-glycolide) (PLGA) is a biocompatible, bio-absorbable, and biodegradable polymer that can be used to formulate many types of implantable and injectable drug delivery systems for clinical and veterinary applications. PLGA microspheres have been reported as carriers for site-specific delivery of various drugs like adapalene and tetracycline (see, Rolland A, et al., "Site specific delivery to pilosebaceous structures using polymeric microspheres," Pharm. Res., Vol. 10, pp. 1738-1774 (1993)).

The imaging and contrast agents of the present disclosure with PLGA can be encapsulated in microspheres in order to prolong its residence time within a subject, and thereby its action, as illustrated generally in FIG. 2B. As shown therein, imaging marker 10a comprising a casing or encapsulating means 15, having plugs 19 at both end made of an appropriate material, such as PEEK or the like. Within the marker 10a are microspheres 21 that encapsulate one or more compositions, such as the cobalt-NAC based compositions described herein, as well as similar compositions. Several technologies are available for encapsulation of hydrophilic drugs into PLGA microspheres by a water-in-oil-in-water (w/o/w) emulsification solvent evaporation technique, such as described by Ogawa, et al. ["A new technique to efficiently entrap leuprolide acetate into microparticles of polylactic acid or copoly (lactic/glycolic) acid," *Chem. Pharm. Bull.*, Vol. 36, pp. 1095-1103 (1988)]; and by Conway, et al. ["Double emulsion microencapsulation of proteins as model antigens using polylactide polymers: effect of emulsifiers on microsphere characteristics and release kinetics," *Eur. J. Pharm. Biopharm.* Vol. 42, pp. 42-48 (1996)]. The microspheres 21 containing $CoCl_2$—NAC can be used for labeling of implantable targets for imaging. PLGA/$CoCl_2$/NAC micro- and nano-spheres can be prepared by the double emulsion-solvent evaporation technique as previously reported by Ungaro, et al., ["Cyclodextrins in the production of large porous particles: development of dry powders for the sustained release of insulin to the lungs," *Eur. J. Pharm. Sci.*, Vol. 28, pp. 423-432 (2006)].

This approach of encapsulation of contrast agents within microspheres is illustrated generally in FIG. 2B, illustrating a marker fabricated by using a contrast agents such as $CoCl_2$—NAC encapsulated within microspheres. The marker can be fabricated by using any appropriate polymer casing, such as PEEK or the like as described herein, which is filled with contrast agent encapsulated microspheres. The dimensions of the marker shown in the schematic illustration of FIG. 2B (e.g., length of about 5.5 mm, outer diameter (O.D.) of about 0.8 mm, and an inner diameter (I.D.) of about 0.7 mm are for illustrative purposes only, and are not meant to be limiting in any manner.

B. Design of Seed(s)/Strands

Figure 3:
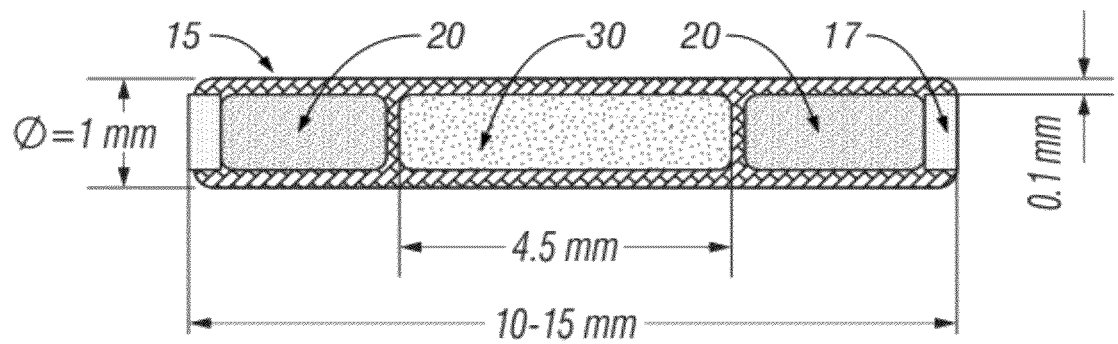
FIG. 3 illustrates a schematic representation of an exemplary imaging marker of the present disclosure in association with a marker seed, within a casing.
Figure 4:
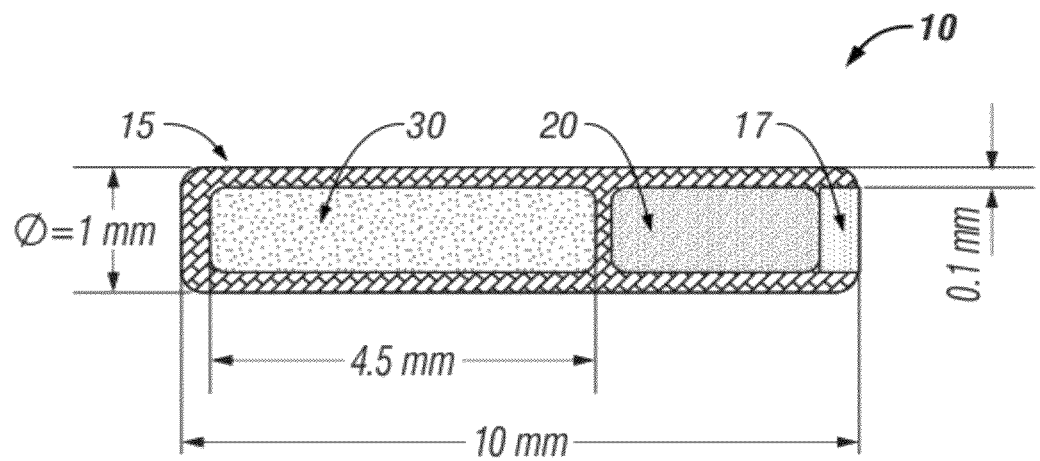
FIG. 4 illustrates a schematic representation of a further embodiment of the present disclosure of an exemplary arrangement of a contrast agent of the present disclosure in association with a marker seed, both within a casing.

FIGS. 3 and 4 illustrate alternative embodiments of the present disclosure, showing a marker configuration wherein the contrast agent 20 is disposed within the casing 15, and wherein the marker 10' further includes one or more individual therapeutic seeds or diagnostic compounds 30. In the marker arrangement illustrated in FIG. 3, the contrast agent 20 is spaced apart at each end of the marker 10', with an individual therapeutic seed or diagnostic compound 30 located intermediate between the contrast agent 20, with the seed 30 and the contrast agents 20 being spaced apart by spacers, preferably made of the same material as the marker casing 15. As further shown in the figure, at each end of the marker 10' is a polymer tap 17, made of the same type (e.g., biodegradable or non-biodegradable) of material as the rest of the marker casing 15. Polymer taps 17 allow for the manufacture of a marker with the described arrangement, as the marker can be initially formed as will be described further herein, and thereafter the chambers for the contrast agent 20 can be filled with the desired contrast agent (e.g., $CoCl_2$—NAC) and then the ends hermetically sealed off by inserting polymer tap 17 into the opening of the contrast agent chamber. In FIG. 4, an alternative arrangement is shown wherein the marker 10' includes a single individual therapeutic seed 30 and a single contrast agent 20 contained within casing 15 and separated by a spacer. In this embodiment of the present disclosure, the marker 10' uses only a single polymer tap 17 to retain the contrast agent 20 within its chamber within the marker casing. In both FIG. 3 and FIG. 4, illustrative marker dimensions are shown, such as the therapeutic seed 30 may be about 4.5 m in length, the diameter of the marker may be in the range from about 0.3 mm to about 1 mm, and the overall length of marker 10' may be in the range of from about 10 to about 15 mm, with a casing wall thickness of about 0.1 mm.

For example, and without limitation, the encapsulated contrast agent marker 10' in FIG. 4 may be made from an extruded polycarbonate, PMMA, or PEEK microtubing (outer diameter (θ)=0.8-1.0 mm, inner diameter=0.6-0.8 mm), the latter of which has a good ability to prevent material diffusion, or similar biodegradable (e.g., glycolide/L-lactide) or non-biodegradable material, as appropriate and as will be described in more detail below. The microtubing is cut to a desired length (here, l=10 mm), and an end formed. A therapeutic seed 30, with an external diameter about 0.6 mm, is passed into the tubing, a tubing material spacer is inserted, and then the contrast agent (e.g., $CoCl_2$—NAC) is injected into the tube using a high-pressure stainless steel syringe or the equivalent. A small polymer plug, tap 17, is then fastened to the open end of the tube 10' and secured in place by local heating, so as to prevent any leakage of the contrast agent. The marker 10' may then be used as a temporary or permanent implant for the treatment of localized prostate cancer, or for other applications as described herein.

The therapeutic seeds 30 are preferably radioactive seeds incorporating low energy photon emitting radionuclides, which are useful in the treatment, diagnosis, and/or localization of a variety of cancers, including eye, prostate, and brain cancers. Preferably, the seeds 30 have an activity range of from about 18 MBq (about 0.5 mCi) to about 111 MBq (3.0 mCi), inclusive, such as ranges from about 18 MBq to about 37 MBq (about 1.0 mCi), inclusive. The radionucleotides or radioisotopes suitable for use in accordance with the present disclosure are preferably those which emit low energy X-rays and which have relatively short half-lives. Once implanted at a treatment site, these isotopes preferably will provide sufficient radiotherapy without posing a radiation danger to the medical practitioner(s), people in the vicinity of the patient, or other parts of the patient's body.

The marker 10' in accordance with this aspect of the disclosure acts as a protective capsule which contains the isotope and prevents it from migrating throughout the body where it might interfere with healthy tissue. Typically, the radioisotope is coated on or contained within a rod or the like which is generally cylindrical and made of low atomic number biocompatible materials such as stainless steel, silver, gold, or titanium which substantially do not absorb X-rays. In accordance with one aspect of the present disclosure, the radioisotope is absorbed on palladium-coated silver beads or spheres and placed inside a titanium or similarly low-Z material capsule. The radioisotope may also be coated on a rod-shaped or similarly-shaped carrier made of similar X-ray transparent (e.g. low Z) material and then placed inside the marker 10', as described above. In one further embodiment of the disclosure, the radioisotope may be adsorbed onto a wire which is then embedded inside the marker capsule 10'. The wire is preferably made of high atomic number material such as gold or tungsten which absorb X-rays.

Exemplary radioisotopes for use in accordance with this aspect of the present disclosure (in association with a cobalt chloride-based contrast agent that facilitates the positive identification of the implanted radioactive seeds under MRI) include but are not limited to cesium-131 ($^{131}Cs$) iodine-135 ($^{135}I$), iodine-125 ($^{125}I$), palladium-103 ($^{103}Pd$), technetium-99 ($^{99}Tc$), xenon-133 ($^{133}Xe$), and yettrium-169 ($^{169}Yt$). In accordance with one aspect of the present disclosure, the marker 10' includes $^{125}I$-labelled titanium seeds which are FDA-approved for the interstitial treatment of prostate cancer.

In accordance with this aspect of the disclosure, the cobalt-chloride-based contrast agents may be used not only as therapeutic agents, but as diagnostic agents as well, and can be multimodality, which means that they can be magnetic (detectable by MRI), radioopaque (detectable by x-ray), fluorescent (detectable by fluorescent techniques) ultrasound detectable, computed tomography detectable, positron emission tomography (PET), and single photon emission tomography (SPECT) detectable. These materials are commercially available, as are the systems for detection and measurements.

The encapsulated contrast agent markers 10' of FIG. 3 and FIG. 4 which include one or more radioactive therapeutic seeds 30 in combination with the contrast agent 20, in accordance with the present disclosure, are preferably designed to possess several important qualities. First, they are relatively small, typically approximately 0.025 inch in diameter and approximately 0.16 inch long so that they may be implanted using minimally invasive instruments and techniques. Second, the radioactive isotope must be enclosed in a biocompatible protective package since the seeds are typically not removed and will remain in the body for many years. Third, each seed may includes a radiopaque (e.g. high Z material) marker so that it can be located at the treatment site with the aid of fluoroscopy. Fourth, the protective package and the radiopaque marker preferably do not cast "shadows" in the irradiation pattern of the isotope. Fifth, the radioisotope should be evenly distributed within the protective package (marker casing 15) so as to avoid any "hot spots" of radiation.

As suggested above, but while not shown, the markers 10' containing one or more therapy seeds 30 such as illustrated in FIGS. 3 and 4 may also contain other components. For example, to assist in tracking their proper placement using standard X-ray imaging techniques, such seeds may contain a radiopaque marker. Markers are typically made of high atomic number (i.e., "high Z") elements or alloys or mixtures containing such elements. Examples of these include platinum, iridium, rhenium, gold, tantalum, lead, bismuth alloys, indium alloys, solder or other alloys with low melting points, tungsten, and silver. Many radiopaque markers are currently being marketed. Examples of suitable radiopaque markers for use with the present disclosure include but are not limited to platinum/iridium markers (International Brachytherapy), gold rods (Bebig GmbH), gold/copper alloy markers (Best Industries), palladium rods (Syncor), tungsten markers (Best Industries), silver rods (Nycomed Amersham), silver spheres (International Isotopes Inc. and Urocor), and silver wires (Oncura). Other radiopaque markers suitable for use herein include radiopaque polymers impregnated with various substances (see, e.g., U.S. Pat. No. 6,077,880).

In accordance with a further aspect of the present disclosure, the markers which act as combined MRI and CT contrast agents described herein, based on cobalt chloride and NAC, may additionally include a number of known CT, radiopaque, and/or fluoroscopic agents. Suitable CT and/or fluoroscopic contrast agents which may be used in accordance with the present disclosure include but are not limited to barium sulfate (accepted for use clinically as a CT contrast agent for X-ray imaging and other diagnosing procedures, and can result in radiopacity; see, A. Sabokbar, et al., J. Bone Joint Surg. Br., Vol. 79, pp. 129-134 (1997)); a mixture of sodium amidotrizoate and meglumine amidotrizoate (such as a mixture of sodium amidotrizoate and meglumine amidotrizoate in a proportion of 10:66 amidotrizoic acid or diatrizoic acid:3,5-bis-acetamido-2,4,6-triiodobenzoic acid); sodium diatrizoate; sodium calciumedetate (also known as calcium EDTA or edentate calcium disodium, and which is advantageously known to be an effective cobalt chelator), and combinations thereof.

C. Variant—Biodegradable Marker with Drug

Figure 5:
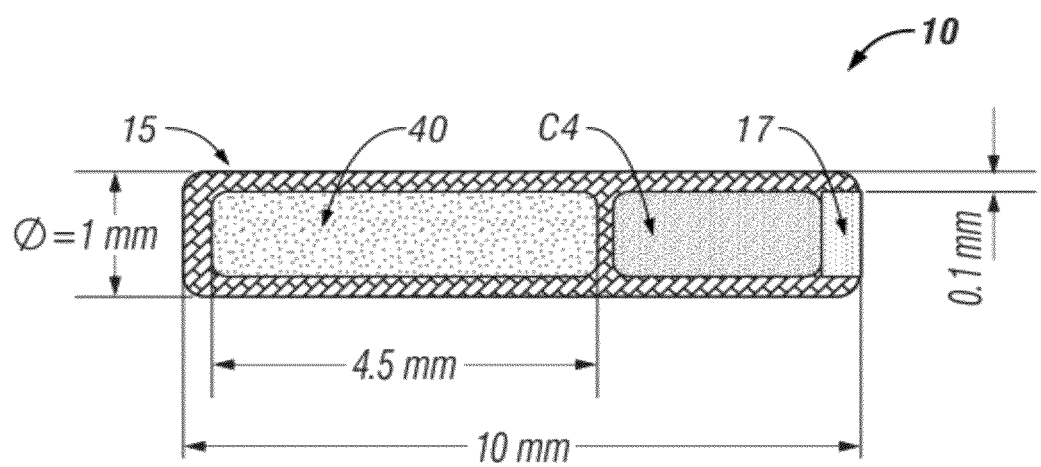
FIG. 5 illustrates an exemplary schematic representation of an imaging marker of the present disclosure in association with a drug, within a single casing.
Figure 6:
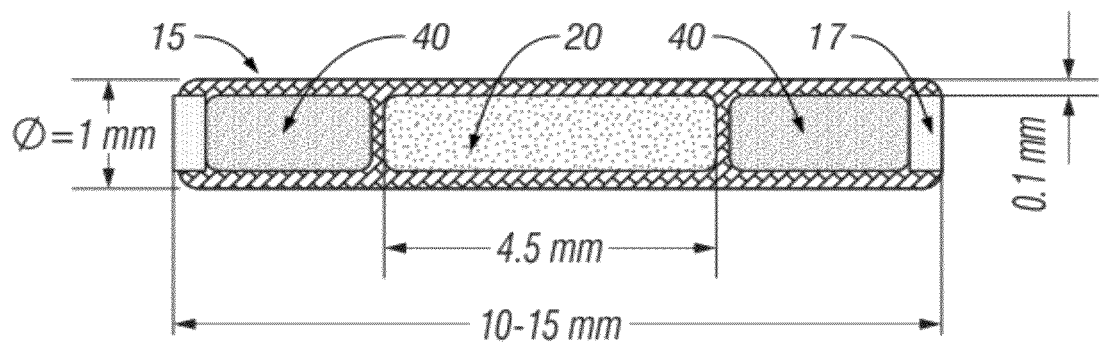
FIG. 6 illustrates a further exemplary schematic representation of an imaging marker of the present disclosure in association with two drug compartments, surrounding the contrast agent.

A further aspect of the present disclosure is illustrated in FIGS. 5 and 6, which illustrate generally a marker 10" comprising a contrast agent 20 in accordance with the present disclosure, in combination with one or more therapeutic agents/drugs 40, both of which are contained within a biodegradable or non-biodegradable casing 15 as described above. As shown in FIG. 5, the marker 10" may include a contrast agent 20 and a therapeutic drug 40 adjacent to each other within casing 15, and separated by a spacer. In this embodiment of the present disclosure, the marker 10" uses only a single polymer tap 17 to retain the contrast agent 20 within its chamber within the marker casing 15. In FIG. 6, an alternative arrangement is shown wherein the marker 10" includes a single individual contrast agent 20 and a therapeutic agent 40 contained within casing 15 on either side of contrast agent 20, with the contrast agent 20 and therapeutic agents 40 each separated by a spacer. In this embodiment of the present disclosure, the marker 10" uses only a polymer tap 17 at each longitudinal end of the marker 10" in order to retain the contrast agent 20 within its chamber within the marker casing.

In both FIG. 5 and FIG. 6, illustrative marker dimensions are shown, such as the therapeutic gent 40 may be about 4.5 m in length, the diameter/thickness of the marker may be in the range from about 0.3 mm to about 1 mm, and the overall length of marker 10" may be in the range of from about 10 to about 15 mm, with a casing wall thickness of about 0.1 mm, without limitation.

Exemplary drugs classes that are preferably to use in accordance with these aspects of the present disclosure include but are not limited to hormone therapy drugs, immune modulators, cytotoxic agents, psa-activated biotoxins, radiation sensitizers, and anti-inflammatory agents.

Drugs

1. Hormone Therapy (Androgen Receptor Blockers)

As suggested above, the markers 10 of the present disclosure may include not only a contrast agent 20 within a casing 15, but may also include one or more drugs. Such drugs suitable for use with the markers and compositions as described herein include hormone therapeutic agents, particularly androgen receptor blockers due to their important role in the treatment of prostate cancer.

Prostate cancer is a leading cause of cancer morbidity and mortality in men, and the androgen receptor (AR) is the primary therapeutic target. In the early stages of prostate cancer, anti-androgen therapy (AAT) is almost universally effective. This typically consists of one or more combinations of GnRH agonists (to suppress pituitary signaling), aromatase inhibitors (to decrease androgen production), and competitive AR antagonists (to block AR directly) such as hydroxy-flutamide (OH—F) or bicalutamide (BiC). This strategy usually works for several years, but over time tumor cells evolve mechanisms for continued growth under these conditions of androgen depletion. Most recurrent, or hormone-refractory prostate cancer (HRPC) is nonetheless dependent on AR-mediated signaling. This can include upregulation of AR protein expression levels, acquisition of mutations within AR that increase its activity in response to alternative hormones (including antagonists), or upregulation of co-activator proteins that augment AR activity. Thus, it is likely that new approaches to block AR activity could significantly extend or increase the effectiveness of AAT. Some recent work in this area implies that novel anti-androgens might have considerable utility in the treatment of both primary and recurrent PCa. Such anti-androgens might not be competitive antagonists that directly bind AR, and could conceivably function via inhibition of downstream events in AR signaling. Accordingly, such focused anti-androgens are suitable for use in the therapy and imaging compositions of the present disclosure.

Androgen receptor (AR) is a steroid hormone receptor that is activated by endogenous androgens, mainly testosterone and 5α-dihydrotestosterone (5α-DHT). AR is also an important drug target, and AR antagonists (antiandrogens) have been widely used for prostate cancer therapy. Antiandrogens currently available on the market are all small molecules that antagonize AR function via binding to the ligand binding domain (LBD). AR peptide antagonist has been proposed as a 'mechanism-based' approach to directly block AR function by interrupting AR-protein interactions from the surface of the receptor. Without targeting the rigid ligand binding pocket within LBD, peptide antagonists allow more flexibility in structure design, and are likely to provide more efficient and complete blockade of AR function as compared to small molecule antagonists. AR interacts with a variety of proteins, and the interaction may be mediated by different functional domains of the receptor. Although varieties of AR-protein interfaces might serve as the target for peptide antagonist, majority of ongoing research is still focusing on peptides that target the LBD, which is mainly due to the abundance of structural information revealed by crystal structures.

The hormone therapy/androgen receptor blocker compounds of the present invention can be used to treat any disease involving folding of the androgen receptor. Patients in need of such treatment often suffer from prostate cancer, including primary and hormone refractory prostate cancer, ovarian cancer, hepatocellular carcinoma, acne vulgaris, endometriosis, acanthosis nigricans, hypertrichosis, breast cancer, precocious puberty, polycystic ovary syndrome, benign prostatic hyperplasia, alopecia (such as androgen-dependent alopecia), hirsutism and hypersexuality/paraphilia.

Exemplary anti-androgen agents (i.e., antagonists against androgen receptor), suitable for use as drug 40 include cyproterone acetate, chlormadinone acetate, flutamide and bicalutamide. Cyproterone acetate is known to inhibit the progress of acne and the development of baldness in teenage patients. Cyproterone acetate is also used for the treatment of virilization and alopecia in female patients. Flutamide and bicalutamide are used as therapeutic agents for prostate cancer, and hydroxyflutamide which is an active form of flutamide has been reported to enhance the transcriptional activity of androgen receptor at a concentration of 10 μmol/L.

On the other hand, an estrogen and androgen receptor antagonist is known as an example of a pure antagonist which serves as an antagonist against nuclear receptors without having agonistic effects, i.e., a substance which completely inhibits the action of the receptors (see, for example, WO98/25916, European Patent Publication No. 0138504, U.S. Pat. No. 4,659,516 and Cancer Research, Vol. 51, 3867 (1991)). WO97/49709 discloses an androgen receptor modulator comprising a non-steroidal tetracyclic compound. Steroid compounds having an aminocarbonylalkyl group at position 7 or an aminocarbonylalkynyl group at position 17 of the steroid carbon skeleton, such as described in International Patent Publication No. WO 91/00732, while steroid compounds having an aromatic ring or an alkyloxy group at position 11 are known from, for example, WO95/17192, which discloses RU486, a modifier for multiple drug resistance. Compounds having various substituents at positions 7 and/or 11 are disclosed in the Japanese Patent Application Nos. Hei 11-274956 and Hei 11-338334. All of these types and classes of compounds may also be used as drug 40 in accordance with aspects of the present disclosure.

2. Immune Modulators

The contrast agents of the present disclosure may also be included with immune regulators, which are those agents which inhibit neutralizing antibodies against one or more viruses.

The selected immune modulator is defined herein as an agent capable of inhibiting the formation by activated B cells of neutralizing antibodies directed against the recombinant viral vector and/or capable of inhibiting cytolytic T lymphocyte (CTL) elimination of the vector. The immune modulator may be selected to interfere with the interactions between the T helper subsets ($T_{H1}$ or $T_{H2}$) and B cells to inhibit neutralizing antibody formation. Alternatively, the immune modulator may be selected to inhibit the interaction between $T_{H1}$ cells and CTLs to reduce the occurrence of CTL elimination of the vector. More specifically, the immune modulator desirably interferes with or blocks the function of the CD4 T cells.

Immune modulators for use in inhibiting neutralizing antibody formation according to this invention may be selected based on the determination of the immunoglobulin subtype of any neutralizing antibody produced in response to the viral vector. The neutralizing antibody that develops in response to administration of a gene therapy viral vector is frequently based on the identity of the virus, the identity of the transgene, what vehicle is being used to deliver the vector and/or the target location or tissue type for viral vector delivery.

For example, $T_h2$ cells are generally responsible for interfering with the efficient transfer of genes administered during gene therapy. This is particularly true when the viral vector is, for example, adenovirus-based. More particularly, the inventors have determined that neutralizing antibodies of the subtypes, $IgG_1$ and IgA, which are dependent upon the interaction between $T_h2$ cells and B cells, appear to be the primary cause of major neutralizing antibodies against adenoviral vectors.

The identity of the neutralizing antibody induced by administering a specific gene therapy recombinant viral vector is readily determined by way of animal trials. For example, administration of adenoviral vectors via the lungs generally induces production of IgA neutralizing antibody, while administration of adenoviral vectors via the blood generally induces $IgG_1$ neutralizing antibody. In these cases, a $T_h2$-dependent immune response interferes with transfer of the adenovirus-based viral vector carrying a therapeutic transgene.

Where the neutralizing antibody induced by viral vector administration is a $T_h2$ mediated antibody, such as IgA or $IgG_1$, the immune modulator selected for use in this method desirably suppresses or prevents the interaction of $T_h2$ cells with B cells. Alternatively, if the induced neutralizing antibody is found to be a $T_h1$ mediated antibody, such as $IgG_{2A}$, the immune modulator desirably suppresses or prevents the interaction of $T_h1$ cells with B cells. Where the reduction of CTL elimination of the viral vectors is desired as well as the blocking of neutralizing antibody formation, the immune modulator is selected for its ability to suppress or block CD4$^+$ $T_h1$ cells to permit prolonged residence of the viral vector in vitro.

The immune modulators suitable for use in the compositions of the present disclosure may comprise soluble or naturally occurring proteins, including cytokines and monoclonal antibodies. The immune modulators may comprise other pharmaceuticals. In addition, the immune modulators according to the invention may be used alone or in combination with one another. For example, cyclophosphamide and the more specific immune modulator anti-CD4 monoclonal antibody may be co-administered. In such a case, cyclophosphamide serves as an agent to block $T_h1$ activation and to stabilize transgene expression beyond the period of transient immune blockade induced by anti-CD4 MAb treatment.

A suitable amount or dosage of the selected immune modulator in accordance with the present disclosure will depend primarily on the identity of the modulator, the amount of the recombinant vector bearing the transgene that is initially administered to the patient, and the method and/or site of delivery of the vector. These factors can be evaluated empirically by one of skill in the art using known procedures. Other secondary factors such as the condition being treated, and the age, weight, general health, and immune status of the patient, may also be considered in determining the dosage of immune modulator to be delivered to the patient in conjunction with a contrast agent and marker therapy system according to this disclosure.

The amount of immune modulator which may be used in the compositions of the present disclosure range from about 0.1 µg to about 50 mg per about $1\times10^7$ pfu/ml virus vector, as appropriate. Generally, for example, a therapeutically effective human dosage of a protein immune modulator, e.g., IL-12 or IFN-γ, is administered in the range of from about 0.5 µg to about 5 mg per about $1\times10^7$ pfu/ml virus vector. Various dosages may be determined by one of skill in the art to balance the therapeutic benefit against any adverse side effects.

3. Cytotoxics

As indicated herein, the contrast agents 20 of the present invention may be employed alone or in combination with each other and/or other suitable therapeutic agents 40 useful in the treatment of a variety of disorders. In accordance with one aspect of the present disclosure, the therapeutic agent 40 includes chemotherapeutic agents, anticancer agents and cytotoxic agents.

Suitable therapeutic agents 40 that are classified as cytotoxic agents are cytotoxic and/or cytolytic. Non-limiting examples include interferon, methotrexate, doxorubicin, daunorubicin, vincristine, vinblastin, mitomycin C, bleomycin, taxol, taxotere, navelbine, adriamycin, amphiphatic amines and the like.

Exemplary classes of anti-cancer agents and cytotoxic agents suitable for use herein include, but are not limited to: alkylating agents, such as nitrogen mustards, alkyl sulfonates, nitrosoureas, ethylenimines, and triazenes; antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids, estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (TAXOL™), docetaxel (TAXOTERE™), combretastatins A, B, C and D and their derivatives, hydrates, and prodrugs (such as combretastatin A-4 phosphate), and epothilones A-F, as well as their analogs, prodrugs, hydrates, solvates, or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators, and monoclonal antibodies. The compounds of the invention may also be used in conjunction with radiation therapy, as appropriate.

Further representative examples of these classes of anticancer and cytotoxic agents include, but are not limited to, mechlorethamine hydrochlordie, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred members of these classes include, but are not limited to paclitaxel, cisplatin, carboplatin, doxorubicin, caminomycin, daunorubicin, aminopterin, methotrexate, methopterin, mitomycin C, ecteinascidin 743, porfiromycin, 5-fluorouracil (5-FU), 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine, and leurosine.

Further examples of anti-cancer and other cytotoxic agents suitable for use in the compositions of the present disclosure also include the epothilone derivatives as found and described in WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253, and WO 00/00485; cyclin dependent kinase inhibitors as found in WO 99/24416; and prenyl-protein transferase inhibitors as found in WO 97/30992 and WO 98/54966.

In additional embodiments, the drug is a humanized anti HER2 monoclonal antibody, RITUXAN™ (rituximab; Genentech; a chimeric anti CD20 monoclonal antibody); OVAREX™ (AltaRex Corporation, MA); PANOREX™ (Glaxo Wellcome, NC; a murine IgG2a antibody); Cetuximab Erbitux (hnclone Systems Inc., NY; an anti-EGFR IgG chimeric antibody); Vitaxin (MedImmune, Inc., MD; Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); and CEAcide (hmnunomedics, NJ; a humanized anti-CEA antibody).

Other suitable antibodies include, but are not limited to, antibodies against the following antigens: CA125, CA 15-3, CA19-9, L6, Lewis Y, Lewis X, alpha-fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, CD40, mucin, P21, MPG, and Neu oncogene product.

In certain embodiments, the therapeutic agent is an immunosuppressive agent. The immunosuppressive agent can be, for example, gancyclovir, etanercept, tacrolimus, cyclosporine, rapamycin, cyclophosphamide, azathioprine, mycophenolate mofetil or methotrexate. Alternatively, the immunosuppressive agent can be, for example, a glucocorticoid (e.g., cortisol or aldosterone) or a glucocorticoid analogue (e.g., prednisone or dexamethasone).

In certain typical embodiments, the immunosuppressive agent is an anti-inflammatory agent, such as arylcarboxylic derivatives, pyrazole-containing derivatives, oxicam derivatives and nicotinic acid derivatives. Classes of anti-inflammatory agents include, for example, cyclooxygenase inhibitors, 5-lipoxygenase inhibitors, and leukotriene receptor antagonists.

Suitable cyclooxygenase inhibitors include meclofenamic acid, mefenamic acid, carprofen, diclofenac, diflunisal, fenbufen, fenoprofen, ibuprofen, indomethacin, ketoprofen, nabumetone, naproxen, sulindac, tenoxicam, tolmetin, and acetylsalicylic acid.

Suitable lipoxygenase inhibitors include redox inhibitors (e.g., catechol butane derivatives, nordihydroguaiaretic acid (NDGA), masoprocol, phenidone, lanopalen, indazolinones, naphazatrom, benzofuranol, alkylhydroxylamine), and non-redox inhibitors (e.g., hydroxythiazoles, methoxyalkylthiazoles, benzopyrans and derivatives thereof, methoxytetrahydropyran, boswellic acids and acetylated derivatives of boswellic acids, and quinolinemethoxyphenylacetic acids substituted with cycloalkyl radicals), and precursors of redox inhibitors.

Other suitable lipoxygenase inhibitors include antioxidants (e.g., phenols, propyl gallate, flavonoids and/or naturally occurring substrates containing flavonoids, hydroxylated derivatives of the flavones, flavonol, dihydroquercetin, luteolin, galangin, orobol, derivatives of chalcone, 4,2',4'-trihydroxychalcone, ortho-aminophenols, N-hydroxyureas, benzofuranols, ebselen and species that increase the activity of the reducing selenoenzymes), iron chelating agents (e.g., hydroxamic acids and derivatives thereof, N-hydroxyureas, 2-benzyl-1-naphthol, catechols, hydroxylamines, carnosol trolox C, catechol, naphthol, sulfasalazine, zyleuton, 5-hydroxyanthranilic acid and 4-(omega-arylalkyl)phenylalkanoic acids), imidazole-containing compounds (e.g., ketoconazole and itraconazole), phenothiazines, and benzopyran derivatives.

Yet other suitable lipoxygenase inhibitors include inhibitors of eicosanoids (e.g., octadecatetraenoic, eicosatetraenoic, docosapentaenoic, eicosahexaenoic and docosahexaenoic acids and esters thereof, PGE1 (prostaglandin E1), PGA2 (prostaglandin A2), viprostol, 15-monohydroxyeicosatetraenoic, 15-monohydroxy-eicosatrienoic and 15-monohydroxyeicosapentaenoic acids, and leukotrienes B5, C5 and D5), compounds interfering with calcium flows, phenothiazines, diphenylbutylamines, verapamil, fuscoside, curcumin, chlorogenic acid, caffeic acid, 5,8,11,14-eicosatetrayenoic acid (ETYA), hydroxyphenylretinamide, lonapalen, esculin, diethylcarbamazine, phenantroline, baicalein, proxicromil, thioethers, diallyl sulfide and di-(1-propenyl) sulfide.

Leukotriene receptor antagonists suitable for use include, but are not limited to, calcitriol, ontazolast, Bayer Bay-x-1005, Ciba-Geigy CGS-25019C, ebselen, Leo Denmark ETH-615, Lilly LY-293111, Ono ONO-4057, Terumo TMK-688, Boehringer Ingleheim BI-RM-270, Lilly LY 213024, Lilly LY 264086, Lilly LY 292728, Ono ONO LB457, Pfizer 105696, Perdue Frederick PF 10042, Rhone-Poulenc Rorer RP 66153, SmithKline Beecham SB-201146, SmithKline Beecham SB-201993, SmithKline Beecham SB-209247, Searle SC-53228, Sumitamo SM 15178, American Home Products WAY 121006, Bayer Bay-o-8276, Warner-Lambert CI-987, Warner-Lambert CI-987BPC-15LY 223982, Lilly LY 233569, Lilly LY-255283, MacroNex MNX-160, Merck and Co. MK-591, Merck and Co. MK-886, Ono ONO-LB-448, Purdue Frederick PF-5901, Rhone-Poulenc Rorer RG 14893, Rhone-Poulenc Rorer RP 66364, Rhone-Poulenc Rorer RP 69698, Shionoogi S-2474, Searle SC-41930, Searle SC-50505, Searle SC-51146, Searle SC-52798, SmithKline Beecham SK&F-104493, Leo Denmark SR-2566, Tanabe T-757 and Teijin TEI-1338.

The above other therapeutic agents, when employed in combination with the compounds of the present invention, may be used, for example, in those amounts indicated in the Physicians' Desk Reference (PDR) or as otherwise determined by one of ordinary skill in the art.

PSA Activated Biotoxins

Another class of drugs which may be used in combination with the contrast agents as described herein include prostate-specific antigen (PSA)-activated biotoxins. Exemplary PSA-activated biotoxins suitable for use with the contrast agents and markers of the present disclosure include, but are not limited to, proaerolysin (PA), and prodrugs of cytotoxic agents, such as PSA-activated doxorubicin prodrug (e.g., a prodrug consisting of doxorubicin (Dox) conjugated to a PSA-specific peptide carrier), or a PSA-activated vinblastine prodrug.

Radiation Sensitizers

Tumor treatment via the use of ionizing radiation can be enhanced by increasing the radiosensitivity of the tumor cells. One method suggested for enhancing radiosensitivity has been the external administration of a compound having a high affinity for electrons, which ideally localizes in the tumor. Proposed radiation sensitizers suitable for use herein include compounds such as halogenated pyrimidines, nitroimidazoles and gadolinium (III) complexes of the pentadentate macrocycle texaphyrin; motexafon gadolinium (MGd, a gadolinium (III) texaphyrin complex) which is currently in Phase III clinical trials for the treatment of brain metastases; (motexafin gadolinium is sometimes referred to as PCI-0120, XCYTRIN™, MGd, or GdTex); and, the related lutetium(III) congener (PCI-0123, LUTRIN™, LuTex)

Particularly useful radiation sensitizers suitable for use as therapeutic agents 40 in accordance with the present disclosure are compounds that preferentially localize in the tumors. For example, it is well known that texaphyrin and porphyrin compounds will preferentially localize in mammalian tumors and have potential radiation sensitization activity. Similarly, other compounds determined to have radiation sensitization activity and that may also preferentially localize in mammalian tumors or such compounds can be derivatized to impart preferential localization in mammalian tumors. For example, such compounds can be derivatized by conventional synthetic chemical techniques to append to a molecule which is known to localize in mammalian tumors. Such molecules include monoclonal antibodies directed to tumor antigens, texaphyrins, porphyrins, peptides such as described in U.S. Pat. No. 5,762,909. Specific techniques for coupling such compounds are disclosed in U.S. Pat. No. 7,579,338, entitled "Methods and Compositions for Treating Atheroma, Tumors and other Neoplastic Tissues".

One preferred compound for use as a radiation sensitizer are porphyrin derivatives and, in particular, iron(III) porphyrin. Such derivatives are known to accumulate in tumor tissue and iron(III) porphyrin has been disclosed as generating hydrogen peroxide from ascorbate and oxygen.

Alternatively, the generation of one or more reactive oxygen species by the radiation sensitizers suitable for use in association with the contrast agents of the present disclosure can be used by itself (or in conjunction with the administration of a reducing metabolite) to therapeutically treat a tumor or atheroma. When used in conjunction with the administration of such reducing metabolites, the radiation sensitizers encompassed by the present invention exclude the cobalt and iron complexes of phthalocyanine and napthalocyanine. In one aspect of the present disclosure, this can be particularly useful when the patient has been exposed to the maximum amount of ionizing radiation which can be tolerated by the patient.

The compounds that may be used herein as radiation sensitizers for cancer treatment may be used singly or in combination with anti-hormonal therapies, or for the inhibition of tumor growth in humans in a regimen with radiation treatment.

Radiation sensitizers may be administered before, or at the same time as, or after administration of the ionizing radiation, preferably before. The radiation sensitizer may be administered as a single dose, as an infusion, or it may be administered as two or more doses separated by an interval of time. Where the radiation sensitizer is administered as two or more doses, the time interval between administrations may be from about one minute to a number of days, preferably from about 5 min to about 1 day, more preferably about 4 to 5 hr. The dosing protocol may be repeated, from one to ten or more times, for example. Dose levels for radiation sensitization using motexafin gadolinium (as a non-limiting example) may range from about 0.05 µmol/kg to about 20 µmol/kg administered in single or multiple doses (e.g. before each fraction of radiation). A lower dosage range is presently preferred for intra-arterial injection or for impregnated stents. In the case of texaphyrins incorporating or conjugated to a radioisotope, the additional administration of radiation as a co-therapeutic agent is optional.

In yet another aspect of the present disclosure, one or more anti-inflammatory agents may be used in association with the therapeutic compositions, methods and systems of the present disclosure in order to reduce inflammatory occurrences in the patients, and increase anti-inflammatory cytokines and aid in the therapeutic treatment of patients with cancer by reducing the inflammation cascade. Generally speaking, any suitable anti-inflammatory therapy (e.g., an anti-inflammatory therapeutic agent) well-known to one of skill in the art can be used in the compositions, methods and systems of the present disclosure. Non-limiting examples of anti-inflammatory agents suitable for use herein include but are not limited to non-steroidal anti-inflammatory drugs (NSAIDs), steroidal anti-inflammatory drugs, beta-agonists, anticholinergic agents, antihistamines (e.g., ethanolamines, ethylenediamines, piperazines, and phenothiazine), and methyl xanthines. Non-limiting examples of NSAIDs include, but are not limited to, aspirin, ibuprofen, salicylates, acetominophen, cuelecoxib (CELEBREX™), diclofenac (VOLTARENT™), etodolac (LODINE™), fenoprofen (NALFON™), indomethacin (INDOCIN™), ketoralac (TORADOL™), oxaprozin (DAYPRO™), nabumetone (RELAFENT™), sulindac (CLINORIL™), tolmentin (TOLECTIN™), rofecoxib (VIOXX™), naproxen (ALEVE™, NAPROSYN™) ketoprofen (ACTRON™) and nabumetone (RELAFEN™), as well as pharmaceutically acceptable derivatives and analogs thereof. Such NSAIDs function by inhibiting a cyclooxygenase enzyme (e.g., COX-1 and/or COX-2). Non-limiting examples of steroidal anti-inflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

D. Multifunctional Marker (for Use in CT and MRI)

In accordance with further aspects of the present disclosure, the MRI markers in accordance with the present disclosure may also include multifunctional markers for other imaging modalities. As can be seen schematically in FIG. 7, a marker 10''' may include a MRI contrast agent 20 and a CT marker 60 or similar modality marker within a biodegradable or non-biodegradable casing or capsule 15. In this embodiment of the present disclosure, the marker 10''' uses only a single polymer tap 17 to retain the CT marker 60 within its chamber within the marker casing 15. In accordance with this aspect of the present disclosure, the CT marker 60, is a marker that is imageable by a CT (computed (axial) tomography) scanner, and the contrast agent marker 20 is imageable by an appropriate magnetic resonance or nuclear imaging system. The CT marker component may also act as a carrier for the MRI agent, in that a solid, porous CT identifiable material, such as ceramic or zirconium oxide ($ZrO_2$) can be used. IN accordance with this aspect, a solution of the MRI agent may be absorbed into the porous cavities with the porous CT identifiable material/CT marker, which may subsequently be contained within a biocompatible casing or housing. While not shown in this figure, it is envisioned that the marker 10''' can also include one or more additional agents within the casing 15 and separated by polymeric spacers as appropriate, wherein the agents are also imagable by a variety entire modality of imaging technologies, including positron emission tomography (PET), single photon emission tomography (SPECT), and fluorescence imaging. Older standard imaging techniques, such as fluoroscopy and ultrasound, may be considered for use with the CT marker 60 as well. Hybrid imaging approaches, such as MRI/CT, MRI/PET, MRI/SPECT, and the like are termed "multimodality imaging" in accordance with the present disclosure, and this hybrid approach is useful in that they enable the study of the same target, with the same imaging agent (or marker, in the present case), on different imaging platforms and at different scales. By way of non-limiting example, in a PET/MRI imaging marker system 10''', the high sensitivity PET could be used to determine areas of focal uptake of a targeted PET/MRI agent within a subject's body, which could then be followed by high resolution MR imaging of that same agent, focusing on the contrast agents of the present disclosure, but with the MR images only being acquired in the localized regions where a PET signal was seen.

Figure 7:
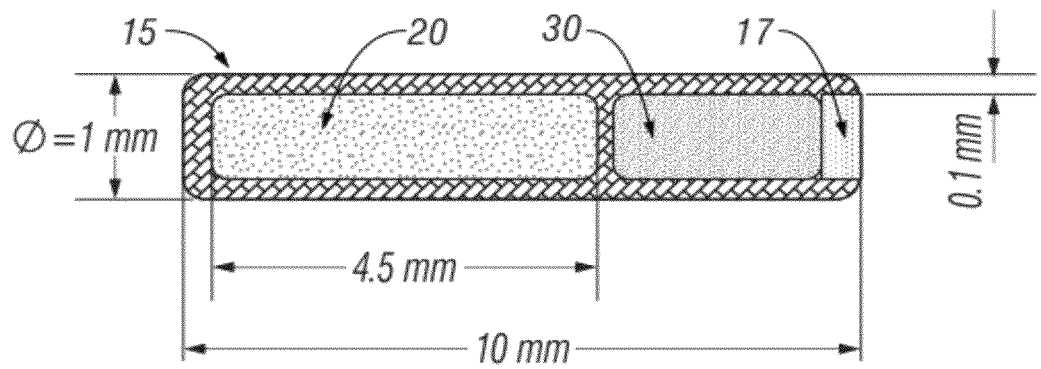
FIG. 7 illustrates a further exemplary schematic representation of an exemplary imaging marker seed of the present disclosure, in association with a contrast agent.

In FIG. 7, illustrative dimensions for marker 10''' are shown, such as the area containing the contrast agent 20 may be about 4.5 mm in length, the area containing the CT marker (or the equivalent tomography modality marker) may be about 2.5 mm in length, the diameter/thickness of the marker may be in the range from about 0.3 mm to about 1 mm, and the overall length of marker 10'' may be in the range of from about 10 to about 15 mm, with a casing wall thickness of about 0.1 mm, without limitation.

The CT markers 60 which may be used in accordance with this aspect of the present disclosure includes but is not limited to gold, silver or similar metals, or simple oxides such as $ZrO_2$ and $Al_2O_3$, including their nanoparticles; $^{111}$In-DTPA-Octreotide (OctreoScan®, OCT); $^{68}$Ga-DOTA-NOC; $^{68}$GA-labeled somatostatin analogs; DOTA-Tyr$^3$ octreotide; $^{123}$I-MIBG; gold (GNPs) or silver nanoparticles; 2-deoxy-d- glucose (2-DG) labeled gold nanoparticles (AuNP-2-DG) (as described by Li, J., et al., *Phys. Med. Biol.*, Vol. 55 (15), pp. 4389-4397 (2010)); polymer-coated bismuth sulfide ($Bi_2S_3$) nanoparticles (see, Rabin, O., et al., *Nat. Mater.*, Vol. 5, pp. 118-122 (2006)); metal complexes using EOB-DTPA as a ligand synthesized with lanthanide metal ions (lanthanum (La), cerium (Ce)], praseodyme (Pr), gadolinium (Gd), dysprosium (Dy), ytterbium (Yb), and lutetium (Lu)) and with nonlanthanides (e.g., lead (Pb) and bismuth (Bi)), as described by Krause, et al. (*Invest. Radiol.*, Vol. 31(8), pp. 502-511 (1996)); mid- to high-Z elements; and fluorescent, paramagnetic gold/silica nanoparticles which are useful for MRI, CT and fluorescence imaging. Also suitable for use herein are maglumine iothalamate (CONRAY® 30) and other related, ionic radiopaque contrast agents.

Marker Production/Manufacture

The markers 10-10''' described herein, particularly those containing at least one contrast agent 20 in accordance with the present disclosure contained within a polymer encapsulation 15, such as a biodegradable polymer micro capillary tube, may be manufactured using manual or automated processes, as well as manufacturing processes that include both manual and automated processes.

A. Manual Production Process

In accordance with one aspect of the present disclosure, the markers of the present invention, when contained within a polymer encapsulation member, such as a biodegradable polymer member, can be manufactured using a manual manufacturing process. The steps of this process are outlined in the flow diagram of FIG. 8, and illustrated generally in FIGS. 9-12. These figures will be described in combination with each other.

Figure 8:
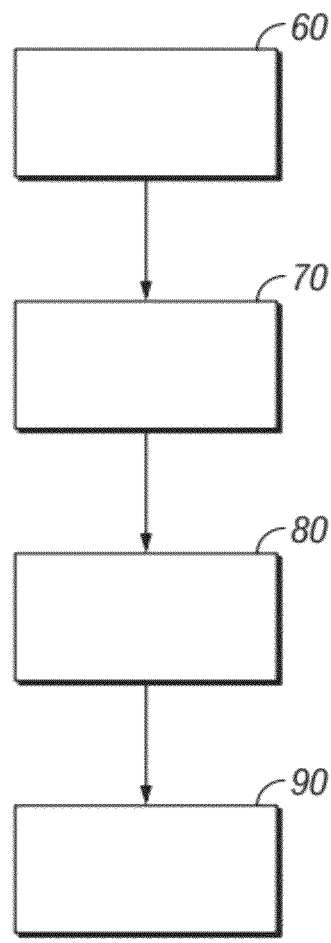
FIG. 8 illustrates a flow chart of an exemplary process of manufacturing markers in association with the present disclosure.

As illustrated in FIG. 8, the steps of manually manufacturing markers of the present disclosure include a first sealing step 60 wherein a first end of the marker tube is hermetically sealed, a cutting step 70 wherein the tube is cut to the desired marker tube length, an injection step 80 wherein a composition, such as the $CoCl_2$—NAC (C4) contrast agent described herein, is injected in the desired amount into the tube, and finally a second sealing step 90, wherein the second end of the tube is hermetically sealed, completing the manufacture process. These general manufacturing steps are illustrated in more detail in FIGS. 9-12.

Figure 9:
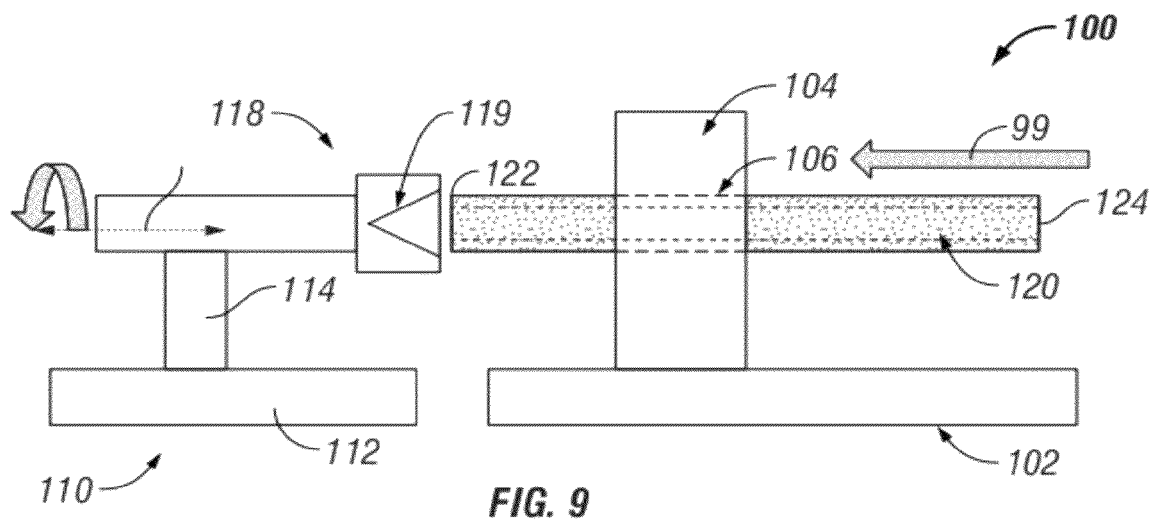
FIG. 9 illustrates a schematic representation of the first step of the process of FIG. 8.

Turning to FIG. 9, the first step 60 of the manual manufacturing process is generally illustrated, and illustrates a general primary support system 100 for use in the sealing of a first end of the associated polymer tube 120. As discussed above, the polymer tube may be made of non-biodegradable materials or biodegradable materials, such as a glycolide/L-lactide micro capillary tube, and is preferably made of a biodegradable material. Such a polymer tube 120 which is used herein may be cylindrical in shape as shown, although other shapes, such as square tubes, hexagonal tubes, and the like are acceptable, and has a proximal end 122 and a distal end 124 spaced laterally apart from each other. Primary support system 100 includes a base support member 102 and a vertical support member 104 mounted in a perpendicular orientation relative to base support member 102. Vertical support member 104 includes a slot or opening 106 formed therein and shaped to receive the tube 120 for sealing, and which may be adjustable vertically as necessary. Support system 100 also includes a sealing assembly 110, which includes a base support member 112, a vertical support member 114 mounted perpendicularly to base 112, and a support arm 116. Support arm 116 is mounted perpendicular to support 114 and substantially parallel to base 112, and is rotatable about horizontal axis α. At one end of support arm 116 is attached a sealing means 118, which preferably includes a shaped sealing cavity 119 which acts to form the shape of the sealed end on tube 120. While sealing cavity 119 is generally illustrated to be angular in shape in FIG. 9, it should be realized that it can be any number of shapes, including round, polygonal (such as for making linkable tubes), or the like, without limitation. Sealing means 118 may be any appropriate means necessary to adequately seal ends of the polymer tube 120, including but not limited to an electrical heater, an ultrasound head, a laser beam, a glue injector, and the like.

With continued reference to FIG. 9, in carrying out the first step of the manual production process, sealing a first end of a polymer tube 120, tube 120 is placed within opening 106 of vertical support member 104, such that one of either the proximal or distal ends, 122 or 124), extends outward in the direction of, and in alignment with, the sealing means 118. In this orientation, distal end 122 should preferably be in the same horizontal plane as the sealing means 118. Sealing means 118 is then engaged, and tube 120 is advanced manually toward the sealing means in the direction of arrow 99 until the distal end 122 enters sealing means 118, whereupon the first end of the tube 120 is sealed.

Figure 10:
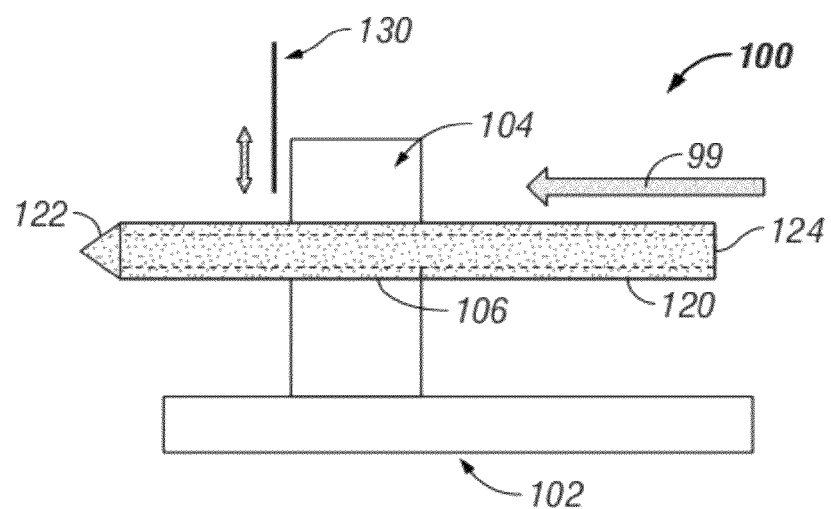
FIG. 10 illustrates a schematic representation of the second step of the process of FIG. 8

Turning now to FIG. 10, the second step of the manual production process, cutting step 70, is generally illustrated. Shown within FIG. 10 is tube 120 having one sealed end 122 (here, at the distal end 120), still retained with slot 106. The tube 120 is then advanced forward in the direction of arrow 99, and a cutter 130, which may be permanently or removably mounted to vertical support 104, is depressed downward so as to cut the tube 120 to its desired length, forming shortened polymer marker tube 120'. Exemplary lengths for these markers are from about 1 mm to about 20 mm, from about 3 mm to about 15 mm, and/or from about 5 mm to about 7 mm, as well as lengths falling within these ranges. The markers may also have an inner diameter (ID) ranging from about 0.4 mm to about 0.6 mm, and an outer diameter ranging from about 0.5 mm to about 1 mm, such as from about 0.6 mm to about 0.8 mm, inclusive.

Figure 11:
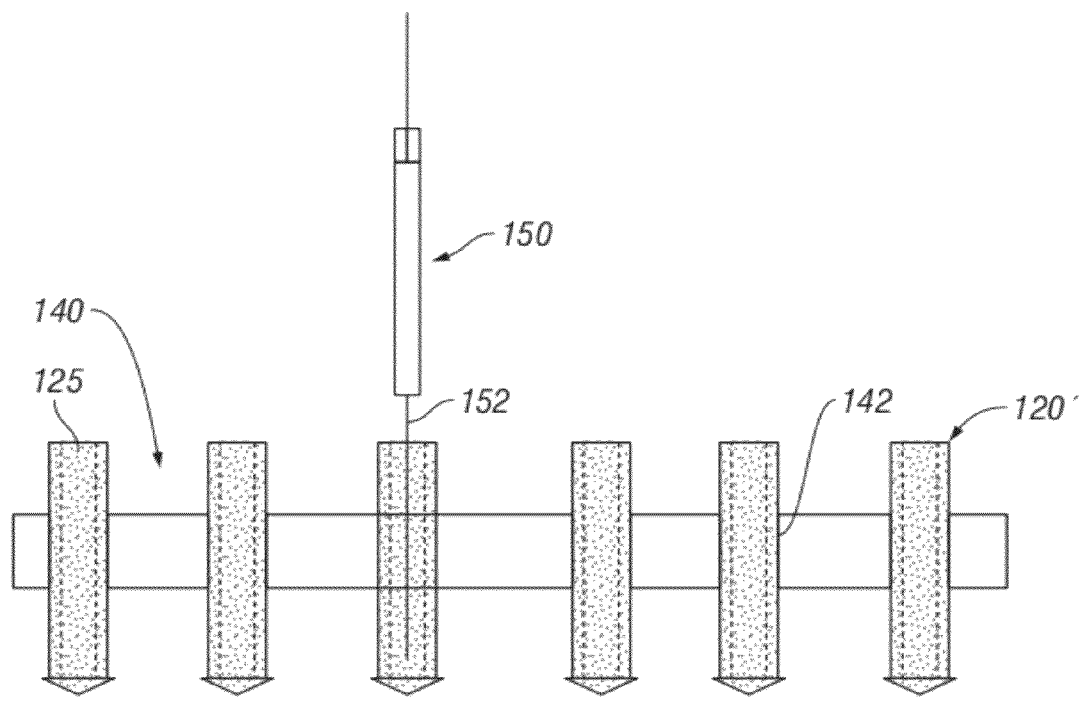
FIG. 11 illustrates a schematic representation of the third step of the process of FIG. 8.

In FIG. 11, the injection step 80 of the manual production process is schematically illustrated. Following the sealing of one end 122 of tube 120 and then cutting the tube to its desired length, the shortened polymer tube 120' is transferred to a horizontal support plate 140 with the open, un-sealed end 125 facing upwards. Horizontal plate 140 includes a plurality of openings 142 extending through the member formed therein. Openings 142 are preferably shaped so as to retain tubes 120' within plate 140, and may or may not allow the sealed end 122 to extend through the plate. Once the shortened tubes 120' have been placed in plate 140, contrast agent in the desired amount (e.g., about 9 μl), alone or in combination with other agents as described herein, is injected into the interior of tube 120' via a needle 152 attached to a high-pressure syringe 150. Once the contrast agent composition has been injected into the tube 120', the tube is ready for the final manufacturing process step—sealing the second end.

Figure 12:
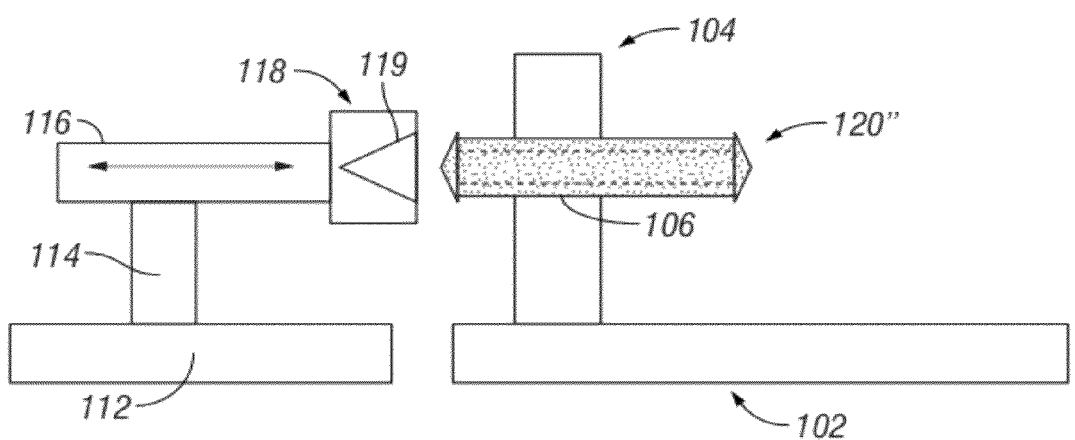
FIG. 12 illustrates a schematic representation of the fourth step of the process of FIG. 8.

With reference to FIG. 12, following the injection of the contrast agent (e.g., $CoCl_2$—NAC (C4)) into the shortened tube 120', the details of the second and final sealing step 90 is generally shown. The tube 120' is fit into slot 106 in the vertical support 104 of the sealing system 100 with unsealed end 125 oriented in substantially the same horizontal plane as the sealing means 118, and the sealing means 118 is advanced toward the unsealed end. Upon engaging with the unsealed end 125 of tube 120', the sealing means 118 seals the second end of the polymer tube, forming the final, sealed marker 120'' containing the contrast agent.

B. Automated Production Process

Figure 13:
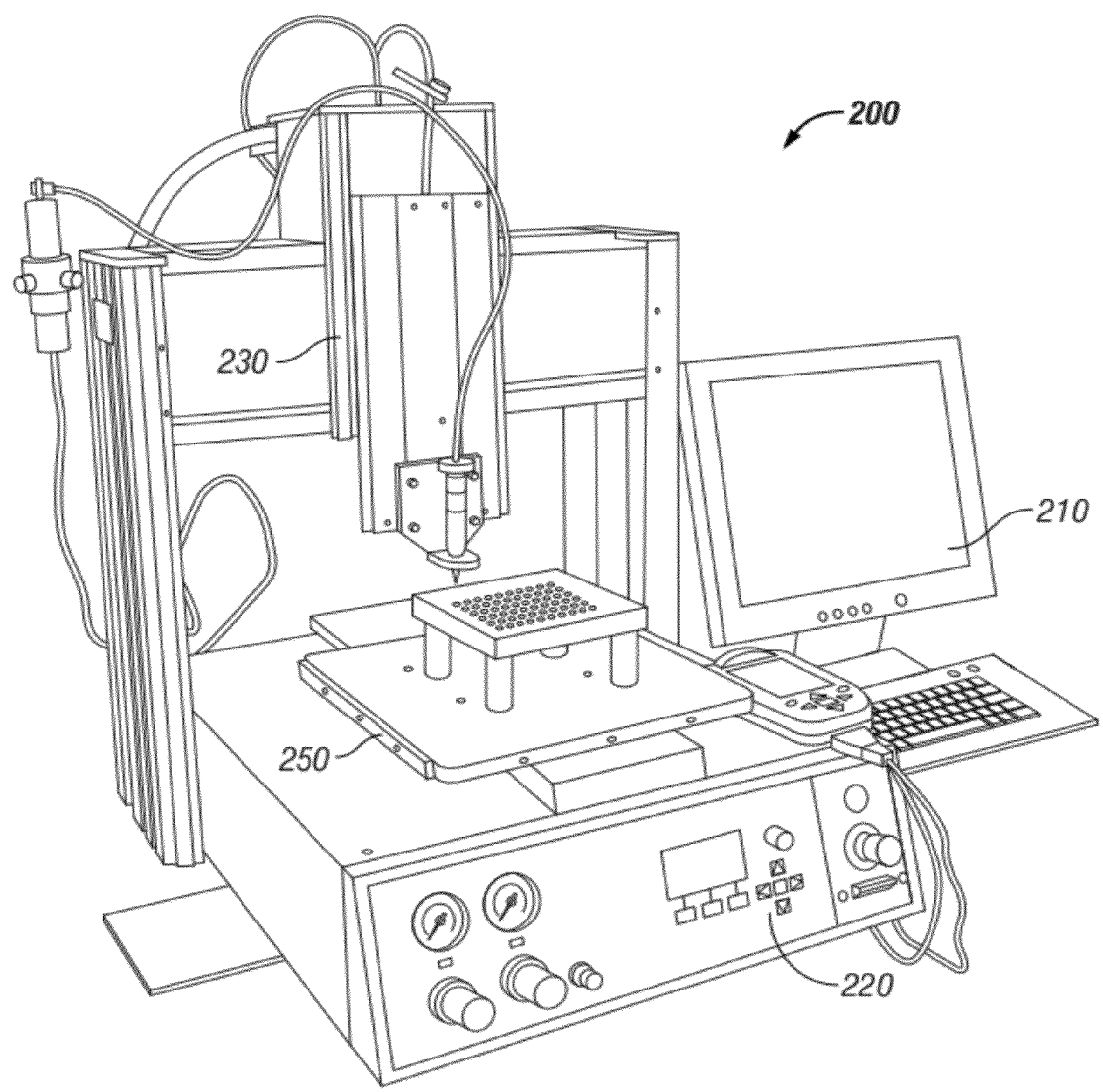
FIG. 13 illustrates an exemplary automated dispensing system (ADS) for use in the automated manufacture of markers in association with the present disclosure.
Figure 14:
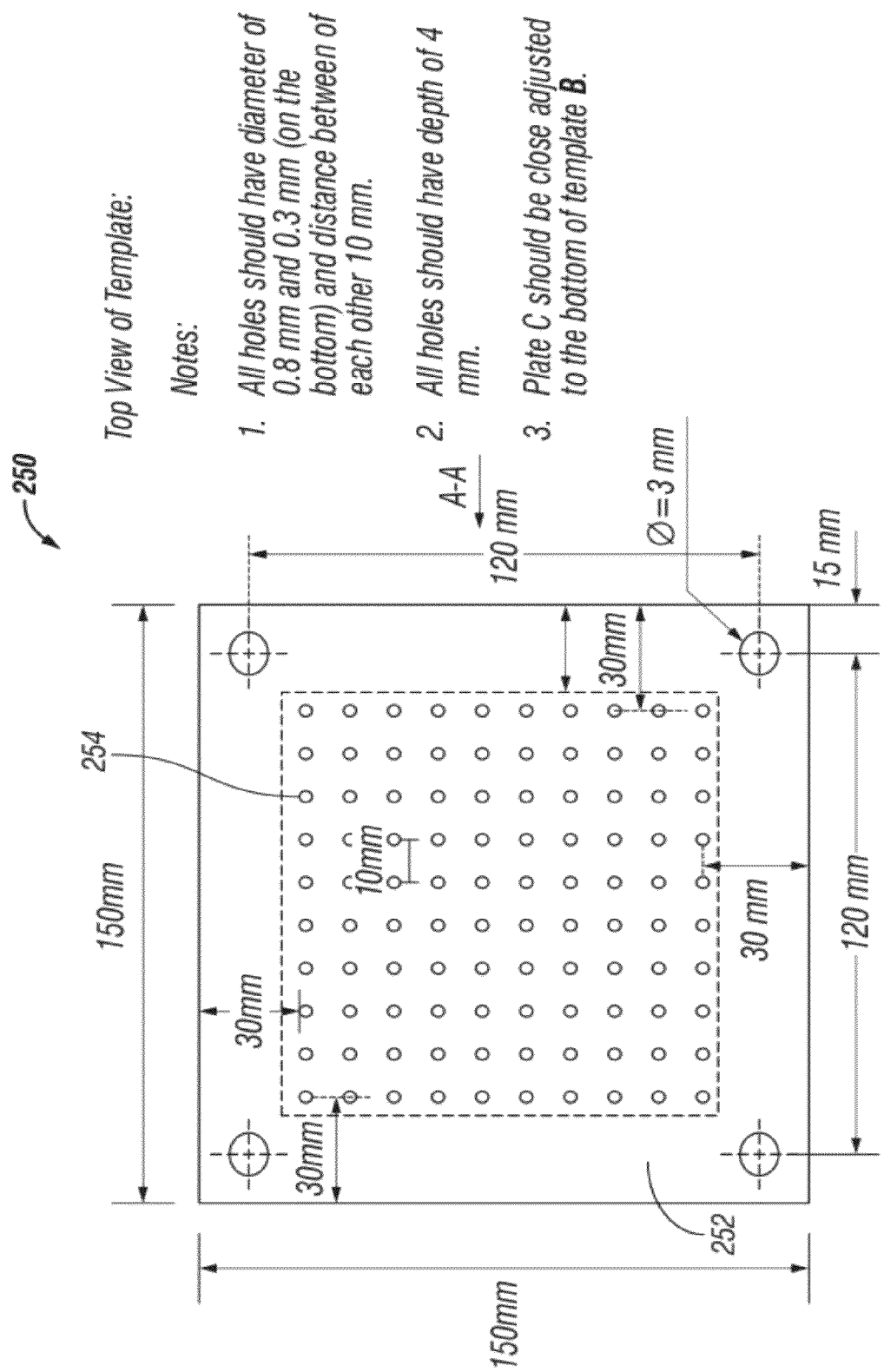
FIG. 14 illustrates a top view of the block/template for use in automated manufacture of markers, in association with the automated dispensing system of FIG. 13.
Figure 15:
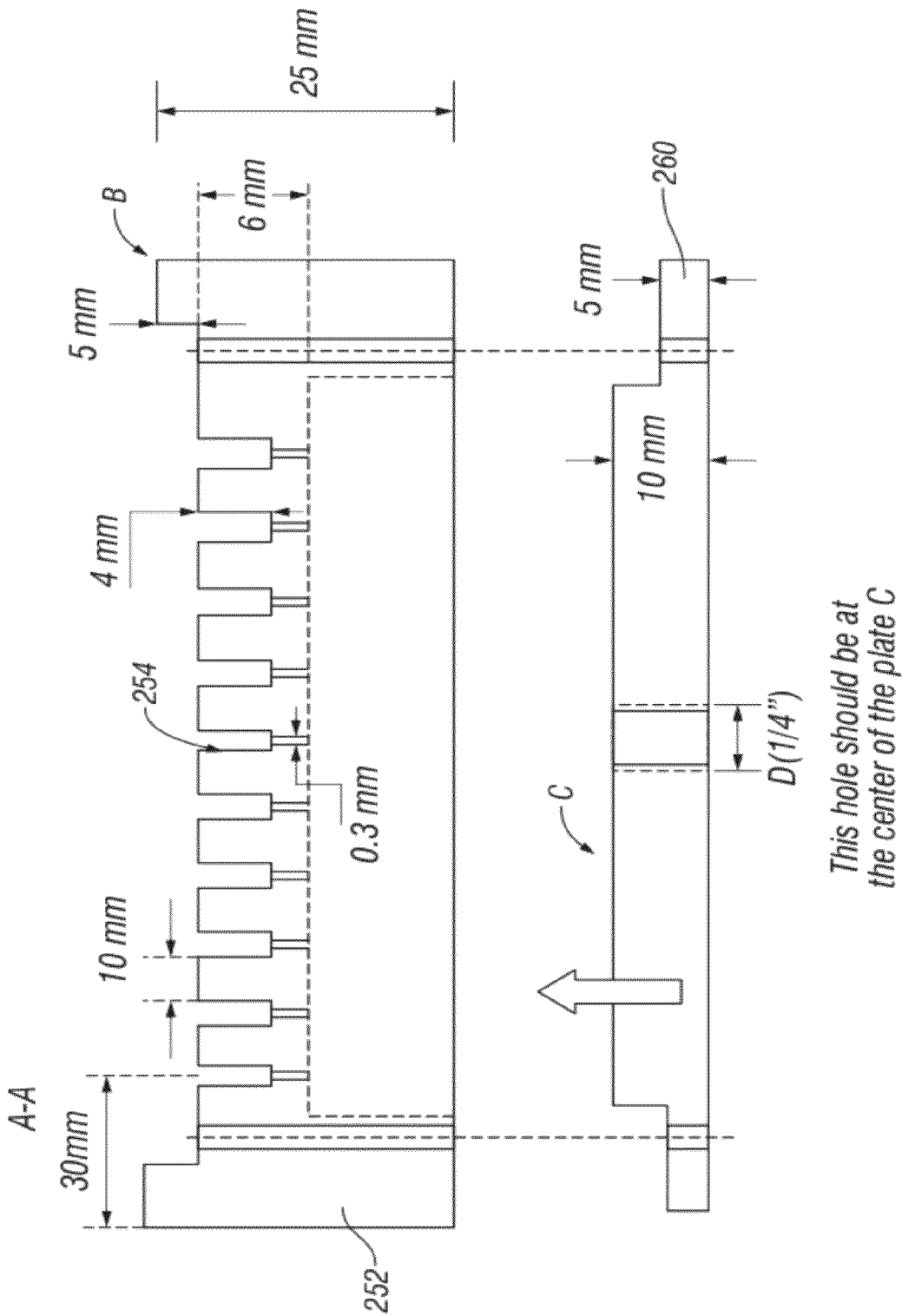
FIG. 15 illustrates a cross-sectional view of the block/template of FIG. 14, taken along line A-A.

The markers described herein, particularly those within a polymer encapsulation 20, such as a biodegradable polymer micro capillary tube, may also be manufactured using an automated processes or system. FIG. 13 illustrates a perspective view of an exemplary high-throughput, automated contrast agent dispensing and manufacturing system 200. FIG. 14 illustrates a top view of an exemplary template for use in the automated dispensing and production process. FIG. 15 illustrates a cross-sectional view of the template of FIG. 14, taken along line A-A. These figures will be discussed in connection with each other.

FIG. 13 illustrates a perspective view of an exemplary automated manufacturing system in accordance with the present disclosure. A high throughput marker manufacturing system 200 comprises a computer 210, a computer controlled controller 220 for programmable control of the automated process, a multi-well plate 250 fit to the top of the controller for retaining the marker capsules during manufacture, and a robotic dispenser device 230 (such as an EFD-325 TT Automated Dispensing Robot System) with support arms and a transport path coupled to the support arms, wherein the robotic dispenser device has aspiration/dispensation heads operatively coupled to the robot.

FIG. 14 is a top view of the multi-well plate 252 which sits atop controller 220, and which includes a plurality of holes 254 formed therein. Holes 254 may be an any appropriate size so as to fit the markers to be automatically manufactured, such as for example (and without limitation), a diameter of about 0.8 mm and a smaller, bottom diameter of about 0.3 mm. FIG. 15 is a cross-sectional view of the plate 252 taken along line A-A, and showing how the system fits together. As seen therein, template 252 sits atop mounting plate 260, which is itself mounted via center opening D to the base of the computer controller 220. Attachment may be via threaded screws, pins, or other similar elongated attachment means which will allow template 252 to be mounted on top of plate 260 and aligned with the robotic system so as to form a seal. The seal between the template 252, mounting plate 260, and controller 220 because in accordance with the processes of this aspect of the disclosure, a vacuum seal is preferably formed on the bottom of the plate 260 so as to prevent tubes from coming out of the holes during manufacture. In an example automated manufacturing process, polymer microtubes are places in the template 252, and one end is sealed; the contrast agent and or any other agents as described herein are dispensed into the polymer tube in an appropriate amount using a high-speed syringe; a microfilament cap of the same material as the polymer casing is inserted into the open end of the tube; and, the second end is sealed using an appropriate sealing method, such as heating, ultrasonic welding, or the like. Important within this automated manufacturing step are preventing the contamination of the markers, preventing loss of solution due to evaporation (which in turn can create undesirable bubbles within the markers), and monitoring for leaking of cobalt-based contrast agent with ICP, to ensure that no cobalt has been released from the marker prior to use in a subject. The exemplary aluminum platform template (block 252 in FIG. 14) has a size of about 150 mm×150 mm (without limitation), and can be used for the precise placement and dispensing of contrast agent solution into the sealed polymer tube with the multi-axis dispensing robots EFD syringe barrel and the associated valving systems.

Block template 252 is preferably made out of an suitable non-metallic, MRI environment compatible material, such as a variety of polymeric materials, glass, carbon fibers, or the like. In accordance with one preferred aspect of the present disclosure, the block template 252 may be made of polyethylene, polypropylene, or fluoropolymers such as polytetrafluoroethylene (TEFLON®). In accordance with further aspects of the present disclosure, contrast agent cobalt- (or other transition metal) markers in accordance with the present disclosure may be placed on or within the upper corners of the block itself in order to provide stereotactic guidance for the needle of the syringe, and for subsequent treatment localization.

Packing of the Product

In accordance with further aspects of the present disclosure, a packaging for the markers manufactured according to the above-described steps may be prepared, wherein the packaging can be sterilized. Sterilization of the packaging may be an added step to the manufacturing processes described above, wherein sterilization may be by the use of ethylene oxide, gamma irradiation, electron beams, hydrogen peroxide, steam, or other known sterilization methods, as well as combinations thereof.

A further object of this disclosure is to furnish a packaging material for the markers which, after sterilization, fulfils most of or all the following physical requirements: 1) the material is preferably (but not necessarily) transparent, 2) the material must provide a good barrier against water; 3) the material must provide a good barrier against gasses (for example, oxygen and carbon dioxide); 4) the material must provide a good barrier against preservatives (for example, phenol and meta-cresol); 5) the material must provide a good barrier against odors (for example preservatives); 6) the material must be resistant against environmental stress cracking (for example, oils, perfumes); 7) the material must be resistant against flex-crack; 8) the material must have good sealing properties (for example, by welding); and 9) the material must not relax significantly during storage and use.

A further object of this disclosure is to furnish a packaging material for the markers detailed herein which, after sterilization, fulfils most of or all the following chemical requirements: 1) the material must not emit substances to the contrast agent, isotope, and/or drug which can affect the health and safety of the patient (referred to generally as "leachables"); 2) the material must have a very low level of extractables; and 3) the material must be compatible with the contrast agent, contrast agent/isotope, or contrast agent/drug formulation.

Needles/Catheters

In further accordance with aspects of the present disclosure, the contrast agents described herein may be used in needles, cannulas and catheters for use in treatment delivery applications, such as the placement of brachytherapy sources, MRI markers, and the like. These concepts are generally illustrated in FIGS. 16-18.

Figures 16A, 16B:
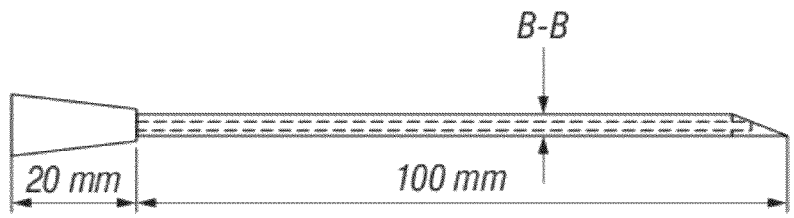
FIG. 16A illustrates an exemplary schematic of a biocompatible polymeric needle cannula in accordance with the present disclosure.
FIG. 16B illustrates a cross-sectional view of the cannula of FIG. 16A, taken along line B-B.
Figure 17:
FIG. 17 illustrates an exemplary schematic of a biocompatible polymeric needle stylet with an MRI marker, in accordance with the present disclosure.

FIGS. 16 and 17 illustrate a schematic diagram of an exemplary biocompatible, polymeric needle cannula and stylet system 300 in accordance with the present disclosure. FIGS. 16 and 17 will be described in combination. The needle cannula system 300 includes a hollow-bore needle 302 and a biocompatible polymeric needle stylet 310, as shown in FIG. 17. The needle cannula system 300 includes a hollow-bore needle 302 having proximal and distal ends 301 and 303, respectively, and a central bore 308 extending therethrough. In accordance with certain aspects of the present disclosure, the needle 302 may be marked in selected increments of length, e.g., 1-cm or 1-mm increments, for use in aiding in the placement of the needle cannula system 300 within a subject, using MRI visualization techniques. A Luer lock type fitting, or the equivalent, 304 is attached to the proximal end 301 of the needle, spaced apart from the distal end 303. The fitting 304 allows the needle system 300 to be joined to a compatible fitting on a syringe barrel. Distal end 303 of the needle is preferably tapered such that it may more readily enter the biological body targeted by the system. FIG. 16B is a cross-section of the needle system 350 taken along line A-A, and shows further exemplary features of this aspect of the disclosure. For example, the needle may be of a variety of sizes, including but not limited to 12 gauge, 16 gauge, 18 gauge, 20 gauge, and the like, as appropriate. In the example illustrated in FIG. 16B, the needle may have an outer diameter (O.D.) of about 1.27 mm, and an inner diameter (I.D.) of about 0.84 mm. The needle 302 is preferably made of a biocompatible, polymeric material, such as PEEK (polyether ether ketone), as described in accordance with the casing 15 for the MRI markers of the present disclosure discussed above. As shown in FIG. 17, the system 300 also includes a biocompatible polymeric needle stylet 310, which includes needle 312, a sized proximal end 314, and a marker 316 containing an imaging marker in accordance with the present disclosure as the opposite, distal end 318. Needle 312 is sized to fit within the bore 308 of needle 302 when stylet 310 is inserted into the needle cannula.

The polymeric needle cannula/stylet system 300 may be used for treatment delivery (i.e., placement of brachytherapy sources, MRI markers, and the like), or for extraction processes (such as for performing biopsies, removing radioactive sources from a subject, and the like), and for therapeutic methods associated with the treatment of cancer. The system 300, comprising the biocompatible, polymeric catheter needle cannula and stylet 310 provide an enhanced visualization of the tip (303) of the needle when it is used with MRI equipment.

Figures 18A, 18B:
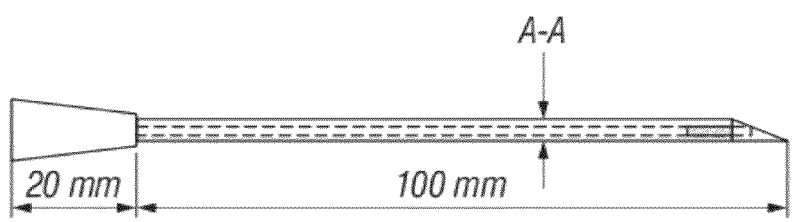
FIG. 18A illustrates an exemplary schematic of an MRI-compatible needle in accordance with the present disclosure.
FIG. 18B illustrates a cross-sectional view of the MRI-compatible needle of FIG. 18A, taken along line C-C.
Figure 18C:
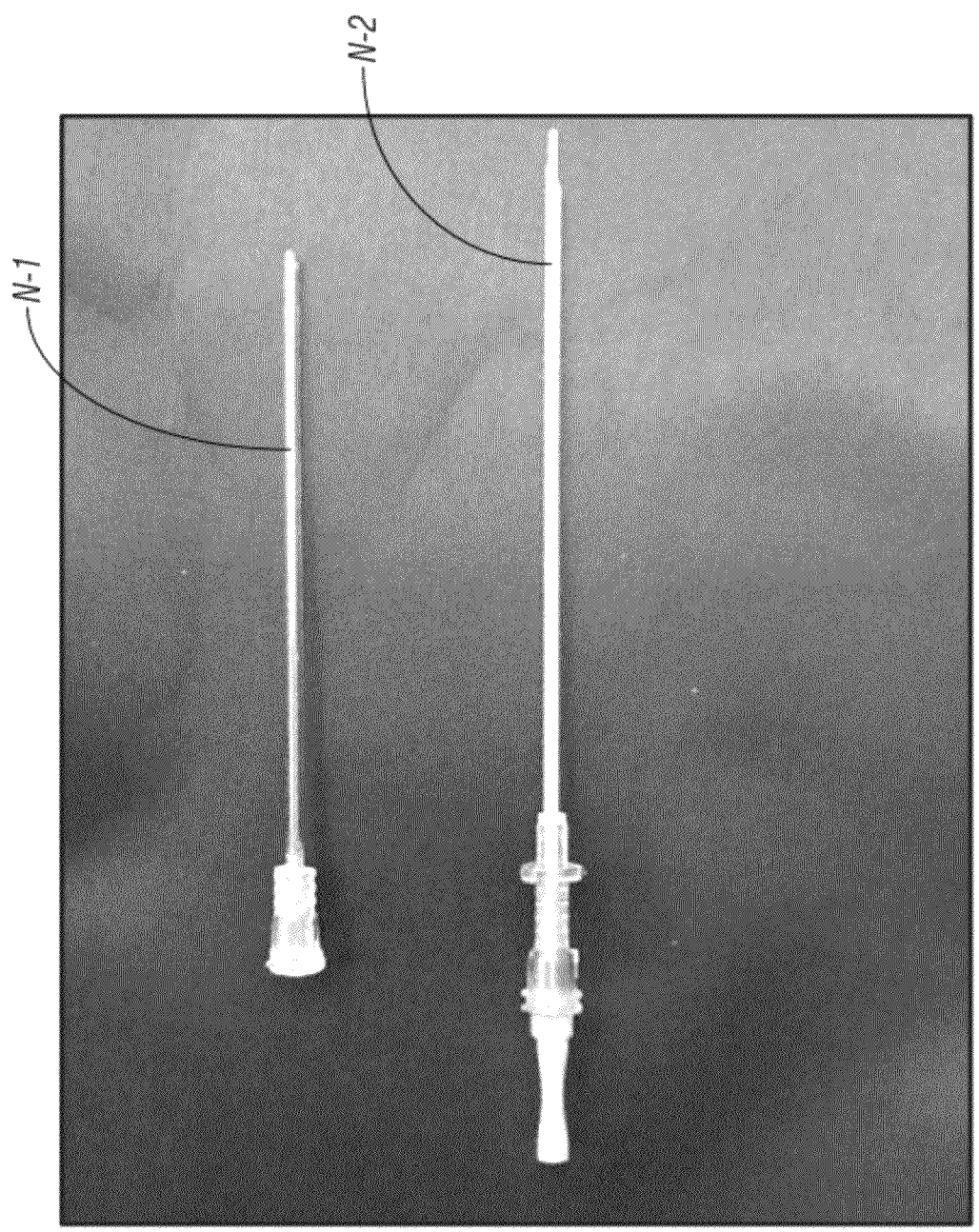
FIG. 18C illustrates exemplary biocompatible polymer needles, N-1 and N-2, suitable for MRI/CT/US image-guided delivery and extraction systems in accordance with the present disclosure.

FIG. 18A illustrates a schematic diagram of an exemplary MRI-compatible needle system 350 in accordance with the present disclosure. The needle system 350 includes a hollow-bore needle 352 having proximal and distal ends 351 and 353, respectively, and a central bore 358 extending therethrough. A Luer-lock type fitting, or the equivalent, 356 is attached to the proximal end 351 of the needle, spaced apart from the distal end 353. The fitting 356 allows the needle system 350 to be joined to a compatible fitting on a syringe barrel. Distal end 353 of the needle is preferably tapered such that it may more readily enter the biological body targeted by the system. An MRI contrast marker 354 in accordance with the present disclosure is included within the bore of the needle 352, at the distal end. In this manner, the marker may be injected into the tissue to mark the location of the treatment (such as brachytherapy seed or therapeutic agent placement within a subject), or to allow biopsy upon imaging. FIG. 18B is a cross-section of the needle system 350 taken along line A-A, and shows further exemplary features of this aspect of the disclosure. For example, the needle may be of a variety of sizes, including but not limited to 12 gauge, 16 gauge, 18 gauge, 20 gauge, and the like, as appropriate. In the example illustrated in FIG. 18B, the needle may have an outer diameter (O.D.) of about 1.27 mm, and an inner diameter (I.D.) of about 0.84 mm. Preferably, the size of the needle 352 used within this system will be appropriate such that the size of the inner diameter is approximately the same as the outer diameter of the imaging marker 354 to be loaded into the distal end of the needle.

Therapeutic Use

The contrast agents, imaging markers, and seeds described herein may be used in the treatment of a variety of cancers, and in particular may be used in conjunction with the treatment, monitoring, and/or therapy associated with prostate cancer, such as in the use of the C4 contrast agent in combination with a marker and a drug in brachytherapy procedures.

Additionally, the present disclosure also envisions the use of the imaging marker described herein in association with real time MRI-guided delivery systems, including polymer needles which are MRI compatible, polymer needles which have a contrast agent, such as the $CoCl_2$—NAC contrast agent or similar contrast agents as described herein embedded at the tip and/or at specific locations within a polymer needle for such MRI guided delivery applications. Similarly, the present disclosure also envisions the design and use of MRI-compatible brachytherapy delivery and extraction systems, including polymer seed and/or strand grasping means, in association with a polymer needle having a contrast agent of the present disclosure contained therein. In association with this aspect of the present disclosure, such a brachytherapy seed delivery device or system could include a device wherein the tip of the grasper is embedded with a cobalt-based contrast agent as described herein, for real-time MRI visualization during seed placement in a patient during treatment.

The ability to accurately co-register PET and TRUS images can be validated by constructing and imaging a custom PET-TRUS prostate phantom. Methods on ultrasound phantom construction are described in literature [See W. D. D'Souza, E. L. Madsen, O. Unal, K. V. Vigen, G. R. Frank, et al., "Tissue mimicking materials for a multi-imaging modality prostate phantom," Med. Phys., vol. 28, pp. 688-700, 2001; K. J. M. Surry, H. J. B. Austin, A. Fenster and T. M. Peters, "Poly(vinyl alcohol) cryogel phantoms for use in ultrasound and MR imaging," Phys Med Biol, vol. 49, pp. 5529-5546, 2004; and E. L. Madsen, M. A. Hobson, S. Hairong, T. Varghese and G. R. Frank, "Tissue-mimicking agar/gelatin material for use in heterogeneous elastography phantoms," Phys. Med. Biol., vol. 50, pp. 5597-5618, 2005] with the exception of any discussion of the manufacturing of PET-ultrasound phantoms. The custom PET-TRUS prostate phantom has structures that simulate the acoustical properties for TRUS imaging and 511 keV activity concentrations for PET imaging. In one embodiment, the PET-TRUS phantom can be made of agar-gelatin-based tissue mimicking materials (TMMs) that are mixed with radioactive water solutions. The TMMs can be made compatible with MR imaging through the correct choice of materials. Since most commercial PET scanners now have CT capability, the phantom can also be made CT compatible (e.g., by adding concentrations of iodine contrast agent or barium sulfate to the radioactive water solutions).

A PET-TRUS (TRUS referring to trans-rectal ultrasound (US)), or PET-US phantom can be constructed using short-lived radioactivity, such as $^{18}F$ (110 minutes half-life). Short-lived radioactivity is readily available from in-house cyclotrons or commercial companies that deliver $^{18}F$-fluorodeoxyglucose. If long term repeated use of the phantom is desired, then the phantom needs to be constructed with a long-lived radioactivity, such as $^{68}Ge$ radioactivity (271 days half-life).

In one embodiment of the present disclosure, a PET-TRUS prostate phantom with a simple geometry is used for validation, as shown in FIGS. 21A-21F. In one embodiment, a multi-modality prostate phantom comprising a rigid container comprising a structure simulating an inner cylindrical prostate region within an outer rectangular pelvic region is prepared. The phantom is comprised of a cylinder or spherical prostate with approximately 511 keV radioactivity concentrated uniformly, and an outer background pelvis with a different uniform concentration of 511 keV radioactivity. For example, the 511 keV activity density could be three times higher in the prostate compared to the pelvis.

The phantom can be constructed with ultrasound agar-gelatin-based tissue-mimicking materials (TMMs) with different ultrasound scatter properties for the prostate and pelvis, using a tissue-mimicking mixture. Similar agar-gelatin mixtures have been shown to have long-term stability at room temperature for at least one year by Madsen, et al. [E. L. Madsen, M. A. Hobson, S. Hairong, T. Varghese and G. R. Frank, "Tissue-mimicking agar/gelatin material for use in heterogeneous elastography phantoms," Phys. Med. Biol., vol. 50, pp. 5597-5618 (2005)]. In one embodiment, the structure simulating an inner cylindrical or spherical prostate region within an outer rectangular pelvic region is comprised of tissue mimicking mixtures of agar, gelatin, $CuCl_2$-$2H_2O$, EDTA-tetra Na Hydrate, NaCl, HCHO, anti-bacterial and/or anti-fungal preservative, glass beads, $BaSO_4$, and deionized radioactive water [See, J. S. Huber, Q. Peng, and W. W. Moses, "Multi-Modality Phantom Development," IEEE Nuclear Science Symposium Conference Record 2007, vol. 4, pp. 2944-2948, (Edited by B. Yu), Honolulu, Hi. (2007)].

The simple phantom can be produced in two stages. First, the outer pelvis is filled, creating an inclusion with a petrolatum-coated rod in the center. This rod is then removed, and the inner prostate is filled with a TMM with different acoustical properties and activity concentration. Similarly, a second rod can be used to create an inclusion for the probe or needle in accordance with this disclosure to allow for TRUS imaging. In a preferred embodiment, a membrane-sealed hole is created in the radioactive pelvis gel for the probe or needle.

Figure 21A:
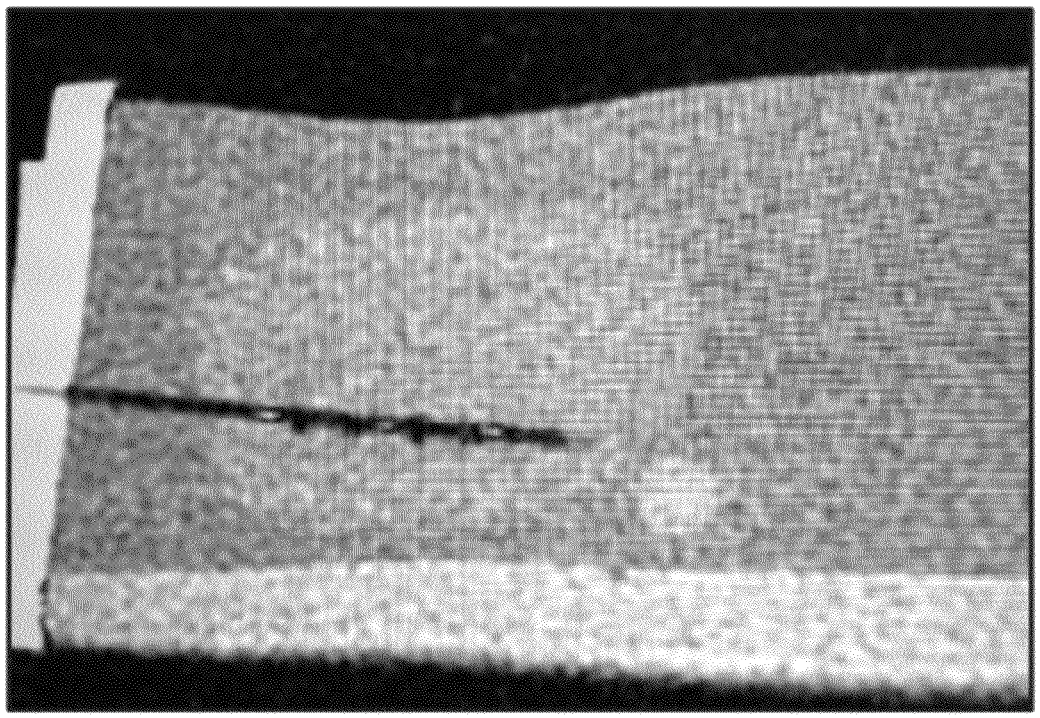
FIG. 21A illustrates a polymer needle, such as needle N-1 or N2 of FIG. 18C, containing MRI/CT/US markers in accordance with the present disclosure being implanted in a tissue-mimicking prostate phantom under MRI guidance.
Figure 21B:
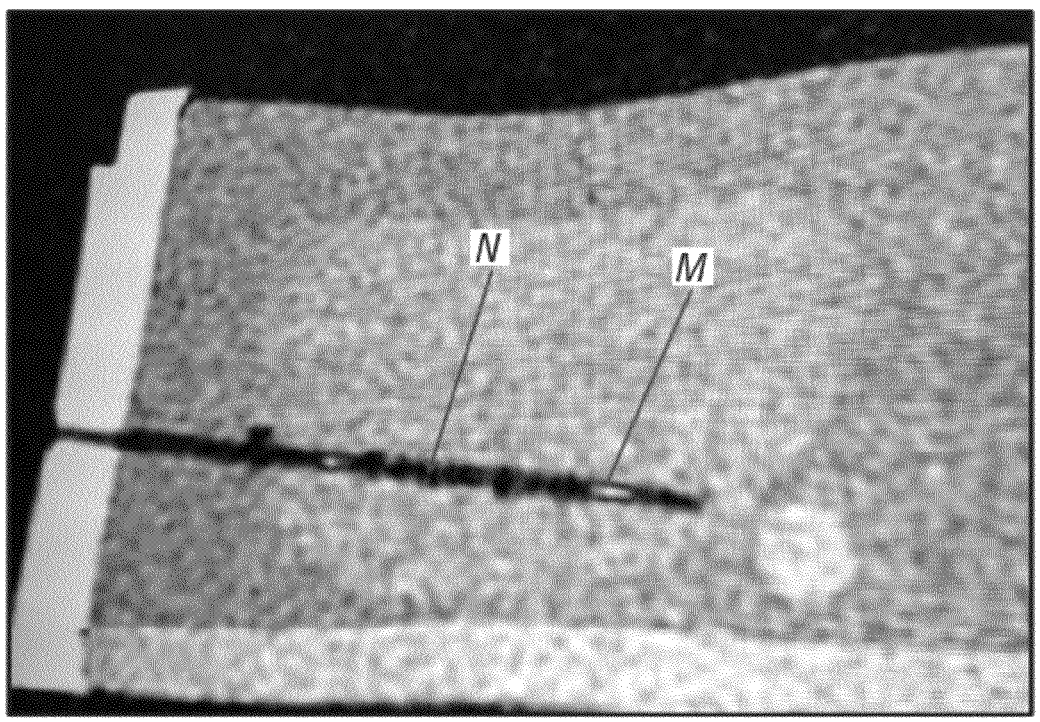
FIG. 21B illustrates an MRI/CT/US marker in accordance with the present disclosure in a tissue mimicking prostate phantom, the marker being visible as a white spot within the polymer needle.
Figure 21C:
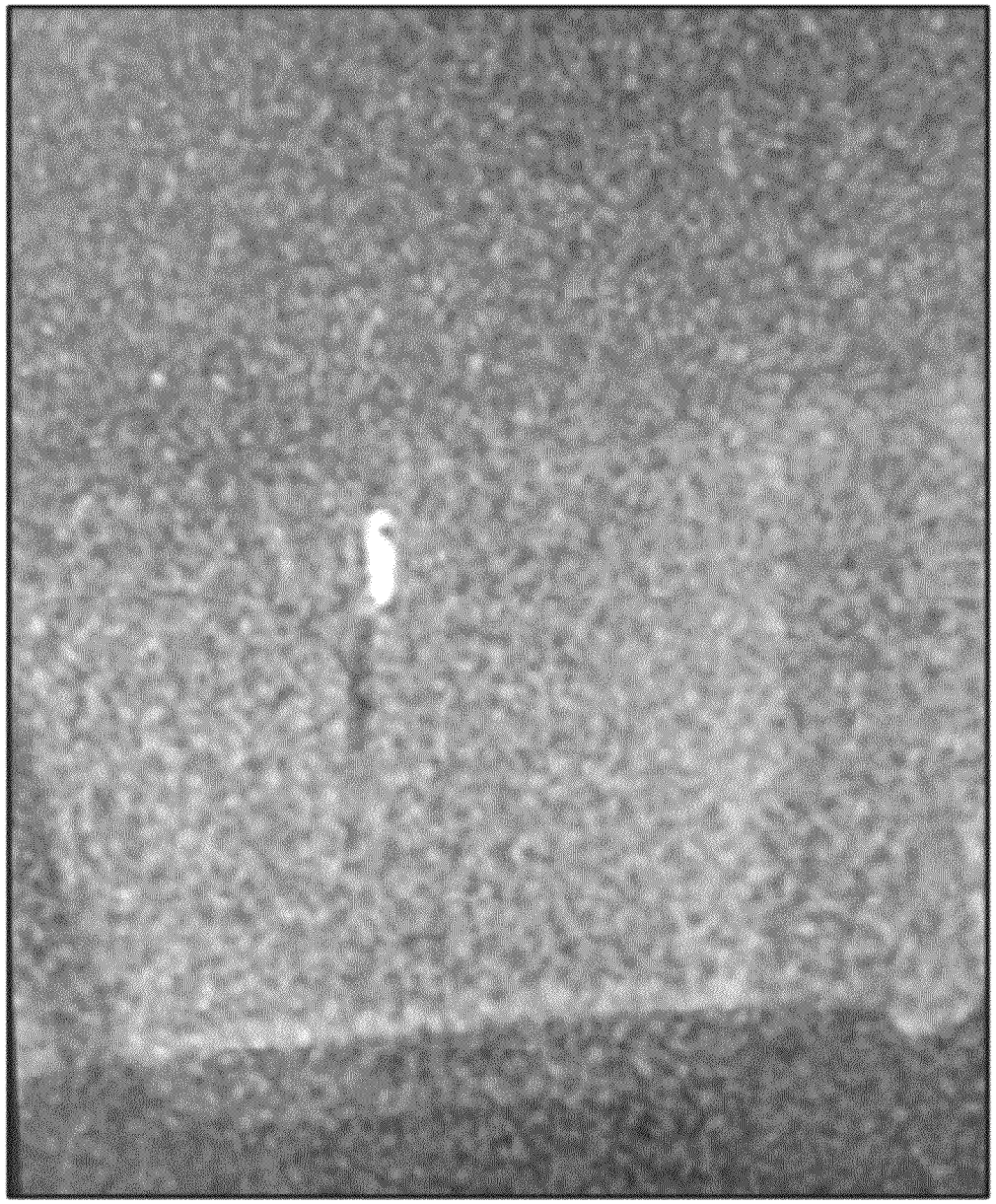
FIG. 21C illustrates an exemplary MRI/CT/US maker with a zirconium core in accordance with the present disclosure, visible in a 3T MRI system, using T1W (standard T1 weighted scan) imaging sequences.
Figure 21E:
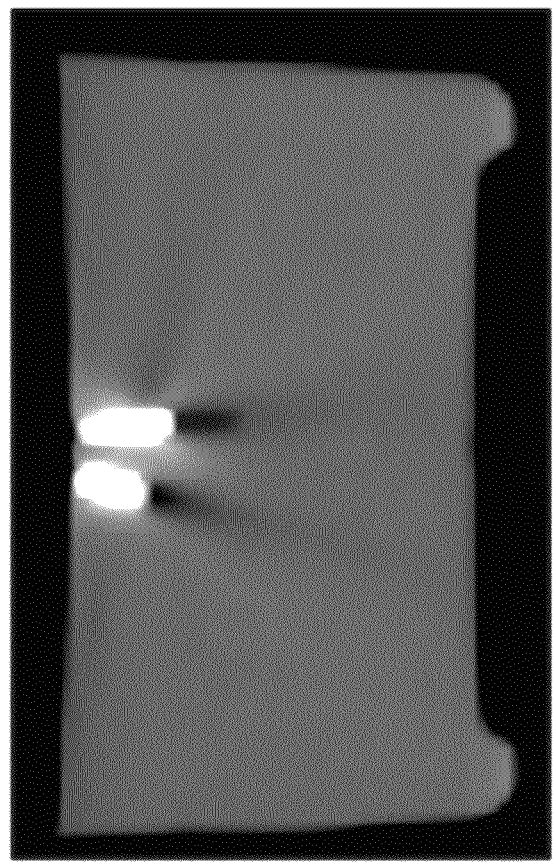
FIG. 21E illustrates an enhanced visual CT image of the marker of FIG. 21D having a zirconium core.
Figure 21D:
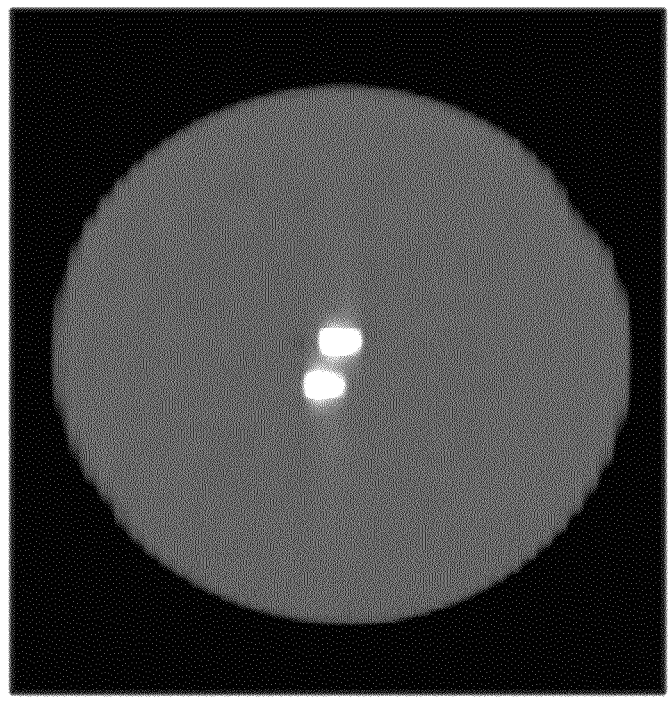
FIG. 21D illustrates a visual CT image of an MRI/CT/US marker in accordance with the present disclosure, having a zirconium ($ZrO_2$) core.
Figure 21F:
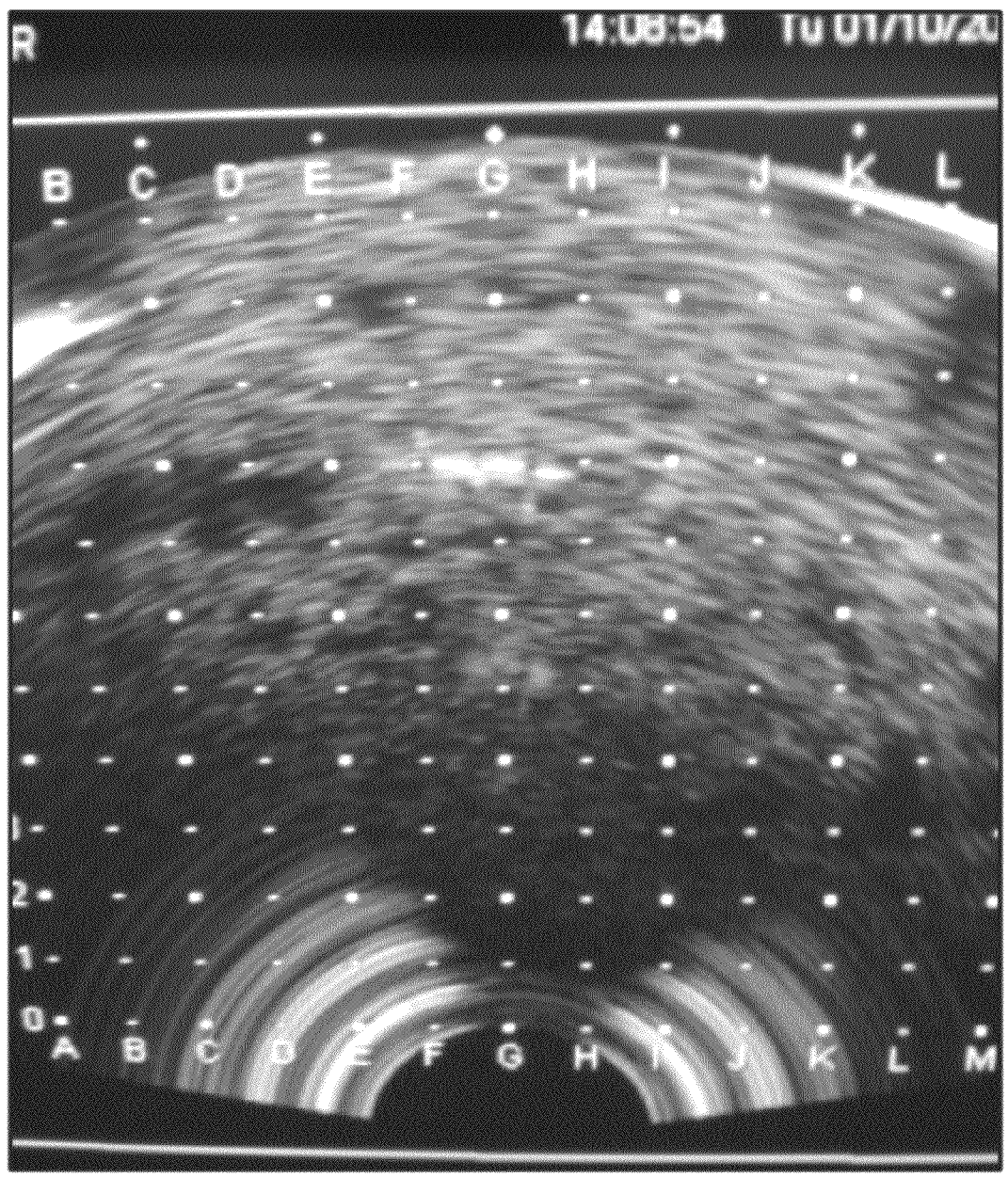
FIG. 21F illustrates an ultrasound (US) image of an MRI/CT/US marker of in accordance with the present disclosure, having a zirconium ($ZrO_2$) core.

In a preferred embodiment, a prostate phantom with realistic anatomy can be used for validation. For instance, the phantom having structures simulating the prostate, rectal wall and urethra in a background gel with an opening for the probe or needle containing the imaging agent, as shown in FIG. 21A can be prepared. If this prostate phantom is only used to validate image co-registration, the phantom does not have to exactly mimic tissue or anatomy of the pelvis region. It can be constructed using a variety of tissue mimicking materials, such as the one described above and shown in the Figures.

In another embodiment, tissue mimicking materials (TMMs) could be used other than agar-gelatin mixtures. Typical TMMs include agar, ZERDINE®, urethanes, epoxies, liquids and natural materials. There are three TMMs commercially available—ZERDINE® from CIRS Inc., condensed-milk-based gel from Gammax RMI, and urethane-rubber-based material from ATS Labs, all of which are suitable for use in preparing prostate phantoms for use in verifying the concepts of the present disclosure. Alternative phantom construction using radioactive water in condensed milk-agar-based mixtures has also been described in the literature [W. D. D'Souza, E. L. Madsen, O. Unal, K. V. Vigen, G. R. Frank, et al., "Tissue Mimicking Materials For a Multi-imaging Modality Prostate Phantom," *Med. Phys.*, vol. 28, pp. 688-700 (2001)], as well as the use of PVA (polyvinyl alcohol) cryogels [K. J. M. Surry, H. J. B. Austin, A. Fenster and T. M. Peters, "Poly(vinyl alcohol) Cryogel Phantoms For Use in Ultrasound and MR Imaging," *Phys Med Biol*, vol. 49, pp. 5529-5546 (2004)] can be used. The urethra could also be simulated by filling a tube with ultrasound gel with some air bubbles.

The following examples are included to demonstrate preferred embodiments of the invention. It should be appreciated by those of skill in the art that the techniques disclosed in the examples which follow represent techniques discovered by the inventor(s) to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLES

Example 1

Preparation of the C4 Contrast Agent

Cobalt chloride hexahydrate ($CoCl_2$-$6H_2O$ (mw=237.9 g/mol, available from Acros)) and NAC (N-Acetyl-L-Cysteine, $HSCH_2CH(NHCOCH_3)CO_2H$ (mw=163.19 g/mol, available from Sigma)) was dissolved in water, resulting in the formation of cobalt-dichloride-N-acetyl cysteine ($CoCl_2$—NAC), referred to herein as the Co—NAC contrast agent. All chemicals were purchased from commercial sources and were used without any further purification. For toxicity testing, two different Co—NAC solutions with low (1 wt. %) concentration of cobalt chloride and with high (10%) concentration were prepared. In both cases, the concentration of NAC in the solution was 2 wt. %. The Co—NAC solution with low cobalt chloride concentration was prepared by dissolving 100 mg (0.42 mmol) of $CoCl_2$-$6H_2O$ and 200 mg (1.22 mmol) of NAC in 9.7 mL distillated water. The solution with high cobalt chloride concentration was prepared by dissolving 1000 mg (4.2 mmol) of $CoCl_2$-$6H_2O$ and 200 mg (1.22 mmol) of NAC in 8.8 mL distilled water. In both cases, the solutions were sonicated at the room temperature for 15 minutes to completely dissolve the components. To avoid any contaminations and bacteria grow, the fresh Co—NAC solutions were prepared every morning for 6 days and immediately delivered for toxicity testing (see, Example 2 below).

The synthesis of the Co—NAC complexes was verified by MS and LC/MS, which indicated (FIG. 1B, FIG. 1C) that cobalt formed a complex with either one or two NAC molecules. To verify the structure, a 50 μL $CoCl_2$ solution (2 wt. %) was mixed with 50 μL of 0.462 M NAC solution, resulting in a 1 wt. % $CoCl_2$ solution with 3 more moles of N-acetyl-cysteine compared to the cobalt (II) chloride. A full scan MS spectrum of this mixture is shown in FIG. 1B in 90% $H_2O$/10% ACN at a concentration of 1 mg/mL. The peak at 220.0 in FIG. 1B corresponds to a cobalt complex with one NAC molecule, $[Co(NAC)_1]^+$; the peak at 384 corresponds to a cobalt complex with two NAC molecules, $[Co(NAC)_2]^+$. FIG. 1C illustrates the MS confirmation spectrums of the Co—NAC complex by CID fragmentation and daughter ion scan. The top scan represents the daughter MS scan of $[Co(NAC)_2]^+$, while the bottom scan shows the daughter MS scan of $[Co(NAC)_1]^+$. The daughter spectrum of $[Co(NAC)_2]^+$ produced a 220.8 m/z peak, which corresponds to $[Co(NAC)_1]^+$. Also, both $[Co(NAC)_1]^+$ and $[Co(NAC)_2]^+$ produced common daughter peaks at 142.8 and 176.7 m/z.

FIG. 1D illustrates an LC/MS/MS chromatogram of the Co—NAC solution, indicating that both $[Co(NAC)_1]^+$ and $[Co(NAC)_2]^+$ complexes are present in the solution, in situ.

Example 2

Toxicity Studies of the Cobalt Contrast Agent

A toxicity and pharmacokinetic study of intraprostatically-administered cobalt dichloride-N-acetyl cysteine ($CoCl_2$—NAC) was conducted in a rat model by the Pharmaceutical Development Center in the Department of Veterinary Medicine and Surgery (DVMS) facilities, U.T.M.D. Anderson Cancer Center, (Houston, Tex.). $CoCl_2$—NAC is a novel MRI marker for prostate brachytherapy under development for use in localization of implanted radioactive seeds under MRI. The encapsulated imaging marker (also referred to as Co—NAC-ECAM) has recently demonstrated efficacy in an in-vivo canine model. The purpose of this study was to evaluate the distribution and potential toxicity of Co—NAC systemic exposure secondary to potential leakage from in-situ rupture of the Co—NAC-ECAMs in a male rat model.

METHODS: The volume of $CoCl_2$—NAC injected (9 µl) was predetermined on the assumption of 80-120 seeds leaking into the human prostate following implantation and scaling to a 150 gram male rat model. Cobalt disposition in plasma and tissues and organ toxicity were evaluated. For the pharmacokinetic arm, 60 male rats (20/group) were assigned to two dose groups and a vehicle control group and administered 1% (low concentration) and 10% (high concentration) $CoCl_2$—NAC or vehicle control as an injection into the prostate. Following dosing, one cohort of 5 animals from each dose-level was sacrificed at 5, 30, and 60 minutes and 6 hours following the end of drug administration. Specific tissues (spleen, heart, brain, prostate, lung, kidney, liver, gut) from all animals were harvested, blotted, and weighed. An additional 3 animals were administered the high concentration and were maintained individually in metabolic cages. Urine and feces were collected at the end of 60 min, 6 and 24 hr intervals on the day prior to dosing and post dosing the following day. All samples were analyzed for total cobalt content by inductively-coupled plasma (ICP) analysis. For the toxicity arm, 30 male rats (10/group) were assigned to two dose groups and a vehicle control group and administered 1% and 10% $CoCl_2$—NAC or vehicle control injected into the prostate. Groups of animals were sacrificed and necropsied on Study Days 1 (24 hrs) and 14 and blood and tissues collected for evaluation of clinical pathology and organ toxicity.

RESULTS: No test article-related morbidity or mortality was observed in the study. Pharmacokinetics: In the high dose group (10%) mean peak peri-prostatic concentrations of 163 ug/g tissue occurred at 5 min but were not quantifiable by 60 minutes in 4 of 5 animals. Cobalt was measurable in the prostatic tissue only in 2 of 5 animals at the 5 min time point in the low dose group (1%). Plasma samples revealed no measurable cobalt in the control or low dose group and only transiently in the high dose group from 5 to 60 minutes with a mean peak concentration of 1.40 µg/ml. No cobalt was measurable in kidney tissue in the control and low dose groups, but was measurable through 6 hours in the high dose group where mean trough concentrations were 1.37 µg/g. In the control group mean cobalt liver concentrations were low (0.03 to 0.06 µg/g tissue from 5 min to 6 hours) compared to those observed in the high dose group (Group III) where mean concentrations ranged from 2.14 µg/g tissue at 5 minutes, peaked at 30 minutes (3.42 µg/g tissue) and declined in a kinetic manner to 1.54 µg/g tissue at 6 hours. Urine and feces sampled the day prior to cobalt administration revealed no significant detectable levels of cobalt, only one animal had a detectable level in feces collected from 6-24 hrs (0.46 µg/g). Following injection of 10% $CoCl_2$—NAC the next day, cobalt was detected in the urine within 60 min with mean peak concentrations in urine of 11.6 µg/ml at 6 hrs. Feces were not available for collection at 60 min and 6 hrs following injection (likely due to the surgery or anesthesia) but mean concentration in feces collected from 6-24 hrs was 3.28 µg/g indicating a fecal elimination 8-fold greater post-dose compared to normal turnover.

These data demonstrate the dual route of elimination of this conjugate (renal and hepatic) which was expected given the published data concerning this molecule.

Toxicity: In the toxicology arm a total of 5 animals died on study. Three of these were in the control group, one from the low-dose and one from the high-dose treated groups. All were associated with surgery or anesthesia. All other animals survived to their scheduled terminations. No test article-related adverse clinical signs were observed.

No toxicologically-important dose-related alterations in group means of the hematological or clinical chemistry parameters were observed. The only changes noted in the serum chemistry of treated animals was an elevation in ALT and AST associated with hemolysis of blood samples or muscle injury as a result of muscle injury/trauma during surgery. Gross pathology only revealed inflammatory reactions due to injury as a result of the intraprostatic injections, surgery, or inadequate wound healing. Microscopic examination revealed no histopathologic lesions related to $CoCl_2$—NAC administration at any of the tested dose levels used in this study thereby setting the NOAEL at the highest dose tested.

CONCLUSION: Under the conditions of this study and based on clinical pathology, organ weights, and gross and microscopic pathology investigations, the no-observed-adverse-effect-level (NOAEL) for this compound is 10% $CoCl_2$—NAC solution, using a single intra-prostatic administration, the highest dose tested. Even at this exposure level, calculated to be 10 to 100 times greater than could be experienced in human clinical studies, plasma drug concentrations were low and of short duration, and peri-prostatic tissues were cleared of $CoCl_2$—NAC rapidly. Concentrations 2-fold higher in the kidney and liver vs. blood were observed in the high exposure group indicating, as hypothesized, renal and hepatic routes of elimination for this compound. These data coupled with the previous MRI data indicate that $CoCl_2$—NAC will be safe and effective when used at far lower exposure levels in human clinical trials.

Example 3

Use of a Marker in a Canine Prostate for Imaging Purposes

Marker

To identify potential imaging markers, numerous agents were investigated—both commercially available and synthesized in the laboratory—with paramagnetic and superparamagnetic properties. The paramagnetic contrast agents included Omniscan (Gadodiamide), L-PG-Bz-DPTA-Gd, and cobalt (II) chloride-NAC compounds with different concentrations. The supraparamagnetic contrast agents included Feridex IV, colloidal nanoparticle solutions of $Fe_3O_4$, $CoFe_2O_4$, Mn—Zn, and Ni—Zn-ferrites. The MRI contrast agent based on the $Co^{2+}$ ions was prepared by using anhydrous cobalt (II) chloride and N-acetyl-cysteine reactants, as outlined above. Reagents were purchased from Sigma Aldrich, Acros Organics, or an equivalent source and used as received without further purification. The ratio among the reactants was set in the following stoichiometry: $(CoCl_2)_1(NAC)_3$. The reactants were dissolved in deionized water and stirred at 60° C. Crystals of the synthesized compound were grown from the mixed aqueous solution of $CoCl_2$—NAC by slow water evaporation. The synthesis yielded crystals of compound shown in FIG. 1A. Then, the crystals were dissolved in deionized water with amount of 0.3-10 wt. % and stirred at 60° C.

Construction of Titanium-Acrylic and Titanium-Glass Seed Strands

Initially, the titanium and acrylic seeds were custom designed to have an outer and inner diameter of 3 mm and 1.5 mm and an outer length and inner hollow length of 4.5 mm and 3.5 mm, respectively. After injection of the cobalt-chloride complex contrast ($CoCl_2$—NAC) agent into the manufactured seeds, MRI was performed on the seeds and strand-like combinations. For the canine prostate experiments, standard nonradioactive titanium seeds were incorporated into a synthesized strand, with acrylic and glass tubes cut with an outer diameter of 0.8 mm and length of 5.5 mm, injected with the $CoCl_2$—NAC agent (2 mL), and closed on the ends with two polymer taps.

Phantom and Ex Vivo Prostate

All studies involving animals or animal tissues were performed under an Institutional Animal Care and Use Committee-approved protocol. For this experiment, after completion of another investigator's in vivo experiments, a canine prostate was excised at necropsy, placed in normal saline, and fixed in agarose gel (10% by weight, Type-A, Sigma-Aldrich, St. Louis, Mo.). The ECAMs were subsequently inserted into the prostate and imaged using MRI. Similarly, the ECAMs were inserted into an in-house-manufactured agarose phantom for direct visualization. The signal intensities of the agarose and prostatic tissue were similar on T1 weighted MRI, allowing substantial preliminary assessment of the relative contrast of the ECAMs without a tissue-based phantom. 1.5-T MRI T1-weighted sequences for imaging marker experiments.

All studies were performed on a 1.5-T clinical MRI scanner (Excite HD, GE Healthcare Technologies, Waukesha, Wis.) equipped with a high-performance gradient hardware package (Cardiac Resonance Module) and multichannel, fast-receiver hardware. The maximal achievable slew rate was 120 mT/m/s, maximal amplitude was 23 mT/m, and receiver bandwidth was 500 kHz. For relaxation measurements, the samples were placed in a room temperature water bath and imaged using a quadrature knee coil. T1-weighted measurements used an inversion recovery spin-echo technique (repetition time [TR]/excitation time [TE], 5,000 ms/10 ms; inversion time, 50-4,000 ms). The T2-weighted measurements used a spin echo sequence (TR, 5,000 ms; TE, 20-1,000 ms). T2*-weighted measurements used a multi-echo, fast, gradient echo acquisition (TR, 600 ms; TE, 2-57 ms, with an echo spacing of 3.3 ms). All imaging data were analyzed using in-house software written in MATLAB (MathWorks, Natick, Mass.). The MRI sequences used for the ex vivo experiments have previously been described (see, Shetty, A. M., et al., Journal of Magnetic Resonance Imaging, Vol. 26, pp. 1672-1677 (2007)) and used a high-resolution, three-dimensional, spoiled gradient recalled echo acquisition (TR/TE, 15.6 ms/2.5 ms; flip angle, 60°; voxel size, 0.4×0.4×0.8 mm, receiver bandwidth, 488.3 Hz/pixel). The large flip angle was used to accentuate the signal from the ECAMs (with lower T1-weighted relaxation times) against the background. The high bandwidth and short echo time were chosen to minimize susceptibility artifacts in the region of the titanium markers.

Results

Of the various agents tested, the Co—NAC agent (having both $[Co(NAC)_1]^+$ and $[Co(NAC)_2]^+$ stoichiometry) demonstrated the highest signal on a conventional three-dimensional T1-weighted spoiled gradient recalled acquisition in phantom. Acrylic and glass hollow seeds containing 0.5-5 µL of the Co—NAC aqueous solution (0.3-10 wt. %) were well visualized in a phantom using 1.5-T MRI. Relaxivity measurements were obtained using the slope of the weighted least-squares regression of the relaxation rate versus concentration. Measurement of the spin-lattice relaxivity ($r_1$) at 1.5 T resulted in 0.093±0.022 $mM^{-1}$ $s^{-1}$ (Pearson's $R^2$=0.99), and measurement of the spin-spin relaxivity ($r_2$) was 0.105±0.01 $mM^{-1}$ $s^{-1}$ (Pearson's $R^2$=0.99). The ratio of the relaxivities were >1 (r2/r1=1.21±0.29), which is consistent with T1-weighted positive contrast agents.

Co—NAC Agent Inside Titanium and Acrylic Seeds

Figure 19:
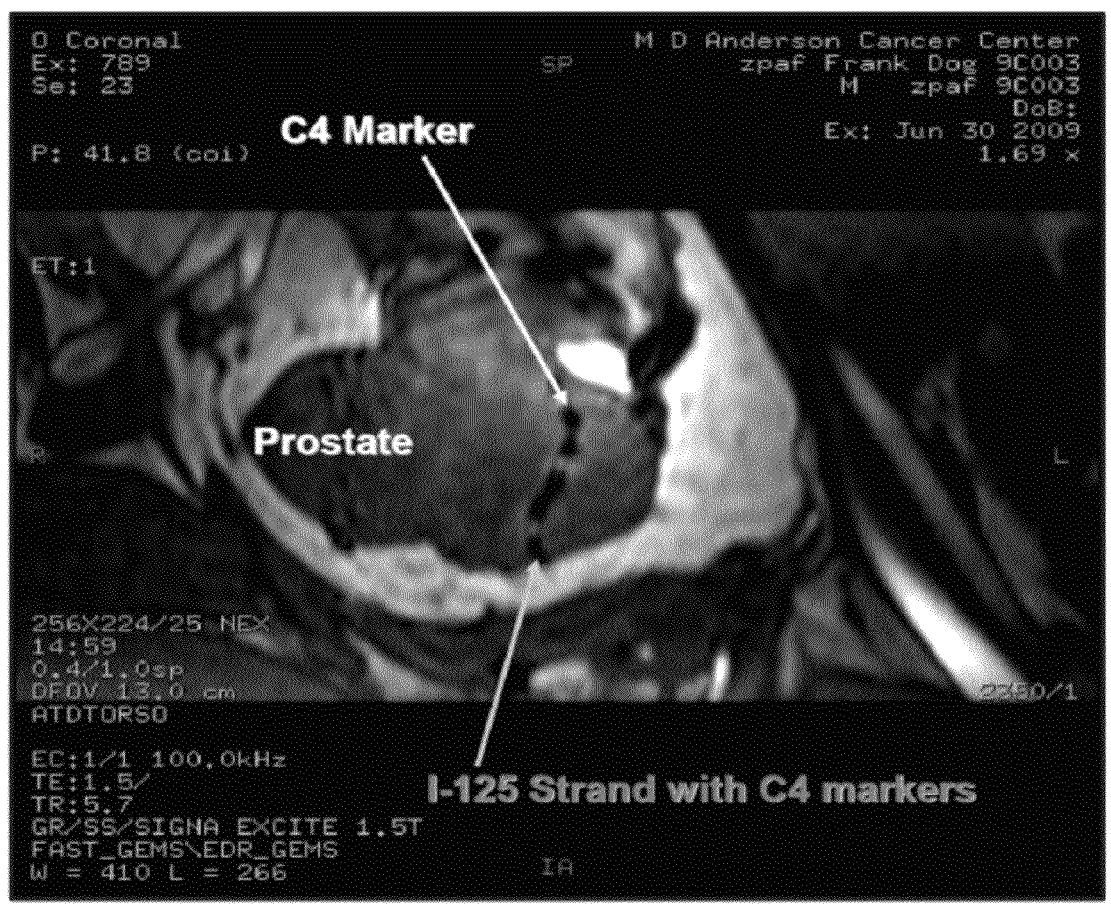
FIG. 19 illustrates a MRI image of an imaging marker and I-125 strand that includes a plurality of imaging markers within a canine prostate.

The Co—NAC contrast agent was able to generate increased signal on T1-weighted MRI using concentrations of 0.5-10% inside polymer seeds in phantom. The Co—NAC agent could not be visualized inside the titanium seed. The Co—NAC agent had positive T1-weighted contrast at lower concentrations in plastic seeds and was able to positively identify the location of the nonradioactive titanium seeds in phantom (see, FIG. 19).

Figure 20:
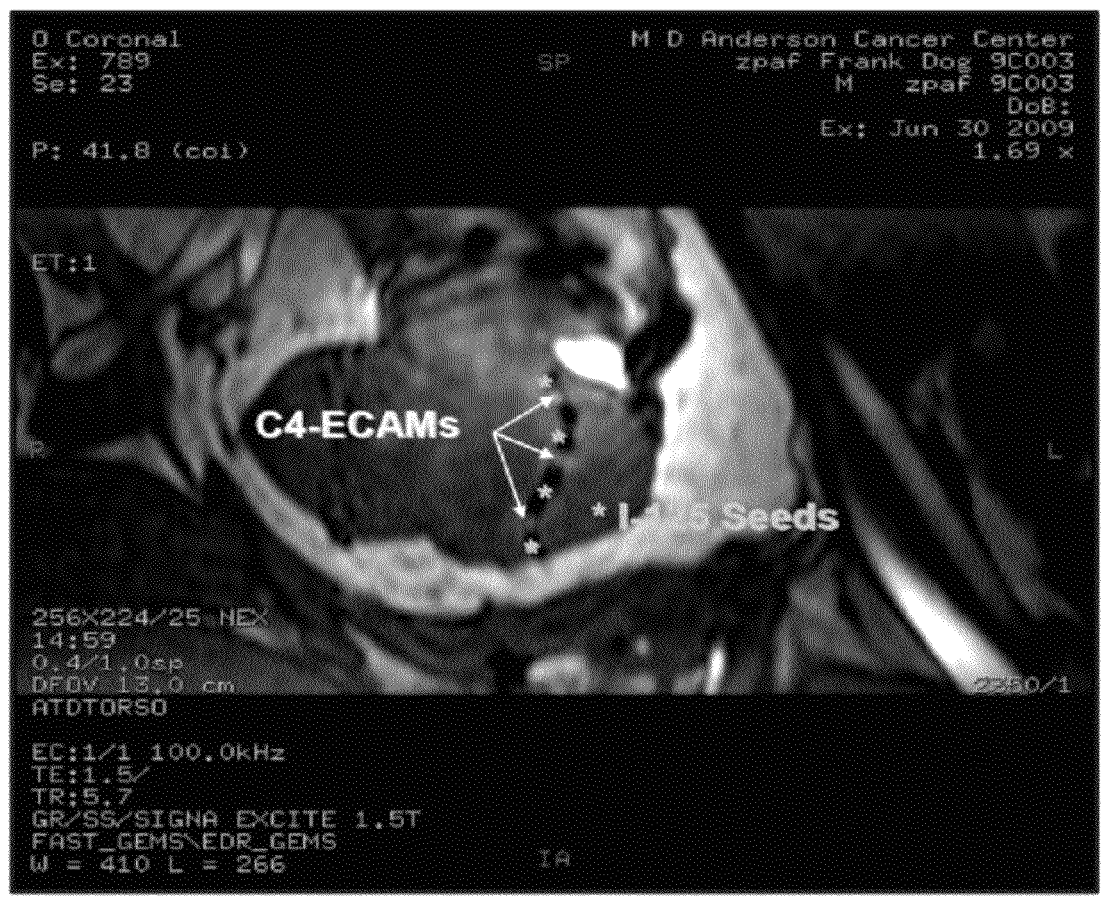
FIG. 20 illustrates contrast agent-ECAMs in accordance with the present disclosure, in place within the prostate of a canine.

Identification of titanium seeds in canine prostate The various combinations of [acrylic/glass]-titanium-[acrylic/glass] and titanium-[acrylic/glass]-titanium rows of seeds were visualized in the canine prostate within an agarose phantom, and the calculations were verified the distance from the ECAM to the center of the titanium seeds (FIG. 20).

Ideally, the contrast agent 20 compound is biocompatible and not harmful to the human body. In the Toxicological Profile for Cobalt published by the U.S. Department of Health and Human Services in 2004, cobalt is noted to be an essential element for daily consumption and required for Vitamin $B_{12}$. In the event the capsule of the imaging marker 10 is compromised, it is an aspect of the present disclosure that there will be no cobalt induced toxicity to the patient.

The instant MRI-based approach to prostate brachytherapy with a contrast marker 10 permits immediate post-operative MRI dosimetric evaluation of the quality of the implant. MRI-based dosimetry can be performed at any center in the country with access to an MRI. If the dose delivered to the prostate cancer is less than adequate, the patient may be taken back to the operating room and additional therapy seeds 40/therapy strand 30 implanted to treat the cancer effectively. In the future, MRI-guided prostate brachytherapy with a contrast marker 10 would facilitate intraoperative dosimetric evaluation to the prostate cancer and surrounding critical organ structures. Optimizing dose intraoperatively with MRI will ensure that each patient receives the highest quality implant and may result in higher cure rates, decreased side-effects, and an improvement in patients' quality of life.

The contrast marker 10 described herein may also permit accurate localization of the radioactive therapy seeds 30 with MRI both during the prostate brachytherapy implant and on subsequent follow-up. Additionally the data obtained by MRI will provide objective analysis to establish national standards of quality for brachytherapy implants. Once the MRI-visible contrast marker 10 is developed, MRI-based prostate brachytherapy dosimetry will be able to accurately define the dose of radiation delivered to the prostate and surrounding critical organ structures. With accurate dose determination, cancer cure rates will increase and side-effects will decrease translating into an improvement in quality of life. The MRI visible contrast marker 10 will permit translatable consistent high-quality prostate brachytherapy implants using MRI-based dosimetry. Therefore, MRI-based prostate brachytherapy dosimetry will immediately replace CT-based dosimetry and permit the establishment of national standards of quality for prostate brachytherapy.

Example of in vitro Evaluation.

Contrast markers 10 can be implanted into a prostate phantom to test the imaging performance of a contrast marker 10, and optimize MRI-based dosimetric evaluation of the prostate and surrounding critical organ structures in vitro. To test the performance of the contrast marker 10 with respect to facilitating MRI-based dosimetric evaluation of a tumor-bearing canine prostate and critical organ structures in vivo a pilot study of MRI perfusion, diffusion, and spectroscopy with the contrast marker 10 can be conducted. One can determine, in a large-animal in vivo model of cancer, whether the contrast marker 10 permits the use of functional MRI to enhance the delivery and dosimetric evaluation of prostate brachytherapy.

To test the performance of the contrast marker 10 with respect to facilitating MRI-based dosimetric evaluation of the prostate and critical organ structures in a prostate, the strand 30 containing non-radioactive titanium seeds (functioning as spacer elements 45) are preloaded along with contrast markers 10 and the strand 30 implanted into the prostate phantom. Optimization of MRI-based dosimetry of the prostate and surrounding critical organ structures can be performed. Dosimetry can be evaluated using an arbitrary fixed activity and prostate dose prescription for dosimetric calculations.

In order to conduct preliminary testing of the system, one can use a disposable prostate phantom (Model M53F, Computerized Imaging Reference System, Inc., Norfolk, Va.), shown in FIG. 21. The phantom contains a liquid medium surrounding a ZERDINE® water-based polymer gel prostate and a penetrable "perineum" for catheter insertion. Though intended for ultrasound imaging, the phantom components are CT and MR-compatible and are easily visualized on CT and MR images. The positional grid template routinely used in clinical prostate brachytherapy can be affixed to the front of the phantom for positional measurements. The strand containing the imaging seeds with contrast markers in accordance with the present disclosure will be positioned accurately within this grid at any one of the grid locations.

An ultrasound Endo-PII probe (Model G20, Sonoline, Siemens Medical Systems, Mount View, Calif.) can be inserted into the rectal opening in the phantom and ultrasound images can be captured every 5 mm within the phantom. Images are typically taken from the base to the apex of the prostate. The output screen has an electronic grid superimposed on all the images to simulate the locations of the needle i.e. the strand 30 insertions. These captured images can then be transferred to the prostate brachytherapy treatment planning system Variseed 7.2. (Varian Medical Systems, Charlottesville, Va.). The organ structures within the phantom can be contoured. Multiple treatment-plans can be generated based on various predetermined geometries of the therapy seeds 35. Based on an assumed activity of each therapy seed 35 to be 1 mCi, dose distributions and dose volume histograms (DVH's) can be computed.

Based on the simulated treatment plans, the imaging markers with contrast agents of the present disclosure can be physically placed in the phantom at locations determined on a given treatment plan. The phantom can be placed into a standard head coil and inserted into the bore of a 1.5T and 3T superconducting MRI scanner (Signa, GE Medical Systems, Waukesha, Wis.). A series of images can be acquired using clinical MRI sequencing protocols. The acquired multiple image sets can be transferred to a Radiation Oncology DICOM storage server Evercore (TeraMedica, Milwaukee, Wis.) from where they can be imported into Variseed 7.2. The prostate and organ structures within the phantom can be contoured from the acquired images. Following the identification of contrast markers, the location of the therapy seeds can be determined and dose computed for each treatment plan.

To illustrate the ability to identify therapy seeds using contrast markers 10, non-radioactive seeds without contrast markers 10 can be implanted into a separate prostate phantom. The seeds can be implanted into identical coordinates as the phantom with contrast markers 10. MR imaging data sets of the phantoms with and without contrast markers 10 can then be qualitatively compared.

In order to illustrate the superiority of MR-based dosimetry using contrast markers 10 over CT-based dosimetry, qualitative comparisons between MR- and CT-based dosimetry can be performed. Using a GE multi-slice CT scanner (GE Medical Systems, Pewaukee, Wis.), a CT data set of the identical phantom can be obtained. Following transfer of the CT data sets to Variseed 7.2, the prostate and critical organ structures can be contoured to generate CT-based dosimetry. A qualitative comparison of MR-based dosimetry to CT-based dosimetry can be performed.

While specific embodiments of the invention have been shown and described in detail to illustrate the application of the principles of the invention, it will be understood that the invention may be embodied otherwise without departing from such principles. For example, these MRI markers can be used for additional applications, including but not limited to stents (including drug-eluting stents, so as to know when a drug has been depleted from such a stent), drains, filters, balloons for minimally invasive procedures, as fiducial markers for monitoring breast cancer during treatment so as to show the progress of the therapy, catheters for both low dose rate (LDR), pulse dose rate (PDR) and high-dose rate (HDR) radiation therapy, applicators for the treatment of gynecologic malignancies, catheters for the treatment of breast and head and neck malignancies, fiducial markers for image guided radiation therapy, MR-guided monitoring probes of thermal therapies (i.e. laser-induced, RF-induced, and cryo-mediated procedures), biopsy needles, intravascular contrast agent for MRI-guided vascular interventions, guidewires, intraprostatic contrast agent.

Other and further embodiments utilizing one or more aspects of the inventions described above can be devised without departing from the spirit of Applicant's invention. For example, the cobalt-NAC contrast agent described herein may include a combination of NAC and a chelating agent not specifically listed herein, but which would be chemically viable to one of skill in the art. Further, the various methods and embodiments of the therapeutic methods and applications described herein can be included in combination with each other to produce variations of the disclosed methods and embodiments. Discussion of singular elements can include plural elements and vice-versa.

The order of steps can occur in a variety of sequences unless otherwise specifically limited. The various steps described herein can be combined with other steps, interlineated with the stated steps, and/or split into multiple steps. Similarly, elements have been described functionally and can be embodied as separate components or can be combined into components having multiple functions.

The inventions have been described in the context of preferred and other embodiments and not every embodiment of the invention has been described. Obvious modifications and alterations to the described embodiments are available to those of ordinary skill in the art. The disclosed and undisclosed embodiments are not intended to limit or restrict the scope or applicability of the invention conceived of by the Applicants, but rather, in conformity with the patent laws, Applicants intend to fully protect all such modifications and improvements that come within the scope or range of equivalent of the following claims.

What is claimed is:

1. An imaging system comprising:
a contrast agent comprises a compound of formula (I)

[Co(Cl)$_m$(NAC)$_n$]  (I)

wherein m is the integer 0, 1, or 2, and n is the integer 1 or 2 and
NAC is N-acetyl-L-cysteine and further comprising a biocompatible and non-biodegradable encapsulating outer structure.

2. The imaging system of claim 1, wherein the contrast agent is a compound of formula (II)

[CoCl$_2$(NAC)$_n$]  (II)

wherein n is the integer 1 or 2, and NAC is N-acetyl-L-cysteine.

3. The contrast agent in claim 2, wherein the concentration of CoCl$_2$ (cobalt chloride) in water ranges from about 0.1 wt. % to about 10 wt. %, and the concentration of NAC (N-acetyl-L-cysteine) in water ranges from about 0.1 wt. % to about 20 wt. %.

4. The imaging system of claim 1, further comprising a radiopaque material selected from the group consisting of zirconium oxide, aluminum oxide, barium sulphate, sodium amidotrizoate, meglumine amidotrizoate, sodium diatrizoate, sodium calciumedetate, Iodixanol, or triphenyl bismuth, alone or in combination thereof.

5. The imaging system of claim 4, wherein the radiopaque material is a carrier for the contrast agent.

6. The imaging system of claim 4, wherein the radiopaque material is a solid, porous CT identifiable material, and the contrast agent is an MRI agent in a solution form absorbing into porous cavities of the radiopaque material.

7. The imaging system of claim 1, wherein NAC is N-acetyl-cysteine in either the L-form or D-form of structure (I)

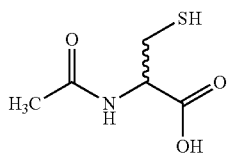

wherein the wavy line is a bond or a point of chemical attachment.

8. The imaging system of claim 1, wherein NAC is N-acetyl-cysteine in a form of rotomer, conformer, solvate, hydrate, or one of derivatives thereof.

9. The imaging system of claim 1, wherein NAC is N-acetyl-cysteine in a form of a pharmaceutically acceptable salt, solvate, or ester thereof.

10. An imaging system comprising:
a biocompatible and non-biodegradable encapsulating outer structure; and
a contrast agent comprises a compound of formula (I)

[Co(Cl)$_m$(NAC)$_n$]  (I)

wherein m is the integer 0, 1, or 2, and n is the integer 1 or 2 and NAC is N-acetyl-L-cysteine and further comprising a radiopaque material selected from the group consisting of zirconium oxide, aluminum oxide, barium sulphate, sodium amidotrizoate, meglumine amidotrizoate, sodium diatrizoate, sodium calciumedetate, Iodixanol, or triphenyl bismuth, alone or in combination thereof.

11. The imaging system of claim 10, wherein the radiopaque material is a carrier for the contrast agent.

12. The imaging system of claim 10, wherein the radiopaque material is a solid, porous CT identifiable material, and the contrast agent is an MRI agent in a solution form absorbing into porous cavities of the radiopaque material.

13. The imaging system of claim 10, wherein NAC is N-acetyl-cysteine in either the L-form or D-form of structure (I)

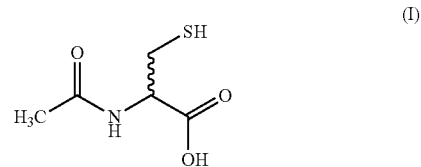

wherein the wavy line is a bond or a point of chemical attachment.

14. The imaging system of claim 10, wherein NAC is N-acetyl-cysteine in a form of rotomer, conformer, solvate, hydrate, or one of derivatives thereof.

15. The imaging system of claim 10, wherein NAC is N-acetyl-cysteine in a form of a pharmaceutically acceptable salt, solvate, or ester thereof.

16. The imaging system of claim 10, wherein the contrast agent comprises a compound of formula (II)

[CoCl$_2$(NAC)$_n$]  (II)

wherein n is the integer 1 or 2.

17. The contrast agent in claim 13, wherein the concentration of CoCl$_2$ (cobalt chloride) in water ranges from about 0.1 wt. % to about 10 wt. %, and the concentration of NAC (N-acetyl-L-cysteine) in water ranges from about 0.1 wt. % to about 20 wt. %.

18. An imaging system comprising:
a biocompatible and non-biodegradable encapsulating outer structure;
a contrast agent comprises a compound of formula (II)

[CoCl$_2$(NAC)$_n$]  (II)

wherein n is the integer 1 or 2, and
the concentration of CoCl$_2$ (cobalt chloride) in water ranges from about 0.1 wt. % to about 10 wt. %, and the concentration of NAC (N-acetyl-L-cysteine) in water ranges from about 0.1 wt. % to about 20 wt. %; and
a radiopaque material comprising zirconium oxide;
wherein the radiopaque material as a carrier for the contrast agent, is a solid, porous CT identifiable material, and the contrast agent is an MRI agent in a solution form absorbing into porous cavities of the radiopaque material.

* * * * *